US012002567B2

(12) United States Patent
Holland et al.

(10) Patent No.: US 12,002,567 B2
(45) Date of Patent: Jun. 4, 2024

(54) SYSTEM AND METHOD FOR LASER TREATMENT OF OCULAR TISSUE BASED ON PATIENT BIOMETRIC DATA AND APPARATUS AND METHOD FOR DETERMINING LASER ENERGY BASED ON AN ANATOMICAL MODEL

(71) Applicant: ViaLase, Inc., Aliso Viejo, CA (US)

(72) Inventors: Guy Holland, San Juan Capistrano, CA (US); Tibor Juhasz, San Clemente, CA (US); Wesley W. Lummis, Rancho Santa Margarita, CA (US); Eric R. Mikula, Aliso Viejo, CA (US); Ferenc Raksi, Mission Viejo, CA (US); Manu Sharma, Ladera Ranch, CA (US); Hadi Srass, Yorba Linda, CA (US); Carlos G. Suarez, Tustin, CA (US)

(73) Assignee: ViaLase, Inc., Aliso Viejo, CA (US)

( * ) Notice: Subject to any disclaimer, the term of this patent is extended or adjusted under 35 U.S.C. 154(b) by 123 days.

(21) Appl. No.: 17/537,382

(22) Filed: Nov. 29, 2021

(65) Prior Publication Data
US 2023/0165719 A1    Jun. 1, 2023

(51) Int. Cl.
*G16H 20/40* (2018.01)
*A61F 9/008* (2006.01)

(52) U.S. Cl.
CPC ......... *G16H 20/40* (2018.01); *A61F 9/00825* (2013.01); *A61F 9/0084* (2013.01);
(Continued)

(58) Field of Classification Search
CPC ........ A61F 9/00825; A61F 2009/00878; A61F 9/00781
See application file for complete search history.

(56) References Cited

U.S. PATENT DOCUMENTS

| 4,423,931 A | 1/1984 | Shapiro |
| 5,123,902 A | 6/1992 | Müller et al. |

(Continued)

FOREIGN PATENT DOCUMENTS

| CN | 104382689 B | 9/2016 |
| CN | 113662507 A | 11/2021 |

(Continued)

OTHER PUBLICATIONS

Slobodzian et al. "Apples to Apples: Which Camera Technologies Work Best for Beam Profiling Applications, Part 2: Baseline Methods and Mode Effects." Ophir Photonics Group. (2015).

(Continued)

*Primary Examiner* — Yingchuan Zhang
*Assistant Examiner* — Jessica L Mullins
(74) *Attorney, Agent, or Firm* — LOZA & LOZA, LLP; David S. Sarisky

(57) ABSTRACT

A look-up table for use in determining an energy parameter for photodisrupting ocular tissue with a laser is generated by determining a plurality of individual spot size distributions, wherein each of the plurality of individual spot size distributions is based on a different set of simulated data and includes an expected spot size of a laser focus at each of a plurality of locations within a modeled target volume of ocular tissue. The plurality of individual spot size distributions are combined to obtain a final spot size distribution that includes a final expected spot size of the laser focus at the plurality of locations of the focus within the modeled target volume of ocular tissue. An energy value is assigned to the plurality of locations of the focus within the modeled target volume of ocular tissue based on the final expected spot size at that location.

11 Claims, 41 Drawing Sheets
(1 of 41 Drawing Sheet(s) Filed in Color)

(52) U.S. Cl.
CPC ............... *A61F 2009/00851* (2013.01); *A61F 2009/00865* (2013.01); *A61F 2009/00872* (2013.01); *A61F 2009/00878* (2013.01)

(56) References Cited

U.S. PATENT DOCUMENTS

| | | | |
|---|---|---|---|
| 5,549,596 A | 8/1996 | Latina | |
| 6,004,314 A | 12/1999 | Wei et al. | |
| 6,059,772 A | 5/2000 | Hsia et al. | |
| 6,251,103 B1 | 6/2001 | Berlin | |
| 6,482,199 B1 | 11/2002 | Neev | |
| 6,682,523 B2 | 1/2004 | Shadduck | |
| 6,989,007 B2 | 1/2006 | Shadduck | |
| 7,131,968 B2 | 11/2006 | Bendett et al. | |
| 7,192,412 B1 | 3/2007 | Zhou et al. | |
| 7,282,046 B2 | 10/2007 | Simon | |
| 7,351,241 B2 | 4/2008 | Bendett et al. | |
| 7,771,417 B2 | 8/2010 | Telfair et al. | |
| 8,011,504 B1 | 9/2011 | Farberov | |
| 8,171,937 B2 | 5/2012 | Bendett et al. | |
| 8,230,866 B2 | 7/2012 | Hauger et al. | |
| 8,394,084 B2 | 3/2013 | Palankar et al. | |
| 8,523,926 B2 | 9/2013 | Neev | |
| 8,540,659 B2 | 9/2013 | Berlin | |
| 8,568,393 B2 | 10/2013 | Palanker | |
| 8,585,686 B2 | 11/2013 | Bergt et al. | |
| 8,679,089 B2 | 3/2014 | Berlin | |
| 8,687,866 B2 | 4/2014 | Marziliano et al. | |
| 8,709,001 B2 | 4/2014 | Blumenkranz et al. | |
| 8,845,624 B2 | 9/2014 | Raksi et al. | |
| 8,920,407 B2 | 12/2014 | Raksi et al. | |
| 9,033,963 B2 | 5/2015 | Vera et al. | |
| 9,044,303 B2 | 6/2015 | Kurtz et al. | |
| 9,101,448 B2 | 8/2015 | Blumenkranz et al. | |
| 9,259,153 B2 | 2/2016 | Goto | |
| 9,259,354 B2 | 2/2016 | Horvath et al. | |
| 9,265,411 B2 | 2/2016 | Chen et al. | |
| 9,271,870 B2 | 3/2016 | Palanker et al. | |
| 9,301,878 B2 | 4/2016 | Raksi et al. | |
| 9,320,650 B2 | 4/2016 | Bendett et al. | |
| 9,441,946 B2 | 9/2016 | Massow et al. | |
| 9,456,925 B2 | 10/2016 | Kurtz et al. | |
| 9,474,648 B2 | 10/2016 | Palanker et al. | |
| 9,498,295 B2 | 11/2016 | Palanker | |
| 9,517,006 B2 | 12/2016 | Izatt et al. | |
| 9,554,702 B2 | 1/2017 | Papac et al. | |
| 9,560,963 B2 | 2/2017 | Buckland et al. | |
| 9,603,741 B2 | 3/2017 | Berlin | |
| 9,603,744 B2 | 3/2017 | Hailmann et al. | |
| 9,629,750 B2 | 4/2017 | Dambacher et al. | |
| 9,642,746 B2 | 5/2017 | Berlin | |
| 9,681,985 B2 | 6/2017 | Andersen et al. | |
| 9,724,238 B2 | 8/2017 | Heitel | |
| 9,750,640 B2 | 9/2017 | Palanker et al. | |
| 9,820,883 B2 | 11/2017 | Berlin | |
| 9,833,357 B2 | 12/2017 | Berlin | |
| 9,844,464 B2 | 12/2017 | Bendett et al. | |
| 9,936,868 B2 | 4/2018 | Izatt et al. | |
| 10,064,757 B2 | 9/2018 | Berlin | |
| 10,073,515 B2 | 9/2018 | Awdeh | |
| 10,159,600 B2 | 12/2018 | Horvath et al. | |
| 10,159,601 B2 | 12/2018 | Berlin | |
| 10,165,941 B2 | 1/2019 | Walsh et al. | |
| 10,179,066 B2 | 1/2019 | Badawi et al. | |
| 10,195,078 B2 | 2/2019 | Horvath et al. | |
| 10,195,079 B2 | 2/2019 | Horvath et al. | |
| 10,195,080 B2 | 2/2019 | Berlin | |
| 10,238,281 B2 | 3/2019 | Isogai et al. | |
| 10,238,541 B2 | 3/2019 | Yee et al. | |
| 10,292,868 B2 | 5/2019 | Chew et al. | |
| 10,335,314 B2 | 7/2019 | Berlin | |
| 10,335,315 B2 | 7/2019 | Goldshleger et al. | |
| 10,360,683 B2 | 7/2019 | Iwase et al. | |
| 10,362,935 B2 | 7/2019 | Dastmalchi et al. | |
| 10,362,936 B2 | 7/2019 | Buckland et al. | |
| 10,363,169 B2 | 7/2019 | Belkin et al. | |
| 10,363,172 B2 | 7/2019 | Kawai et al. | |
| 10,383,689 B2 | 8/2019 | Berlin | |
| 10,390,883 B2 | 8/2019 | Deladurantaye et al. | |
| 10,398,306 B2 | 9/2019 | Liu | |
| 10,406,034 B2 | 9/2019 | Siegele | |
| 10,426,548 B2 | 10/2019 | Tearney et al. | |
| 10,454,237 B2 | 10/2019 | Yu et al. | |
| 10,456,030 B2 | 10/2019 | Buckland et al. | |
| 10,456,209 B2 | 10/2019 | Peyman | |
| 10,478,060 B2 | 11/2019 | Kubota | |
| 10,493,274 B2 | 12/2019 | Irazoqui et al. | |
| 10,499,809 B2 | 12/2019 | Kalina, Jr. et al. | |
| 10,500,094 B2 | 12/2019 | Buzawa et al. | |
| 10,517,760 B2 | 12/2019 | Berlin | |
| 10,524,822 B2 | 1/2020 | Aljuri et al. | |
| 10,537,476 B2 | 1/2020 | Ha et al. | |
| 10,542,883 B2 | 1/2020 | Gooi et al. | |
| 10,543,122 B2 | 1/2020 | Kahook | |
| 10,543,123 B2 | 1/2020 | Neev | |
| 10,568,763 B2 | 2/2020 | Vera et al. | |
| 10,588,694 B1 | 3/2020 | Neev | |
| 10,596,036 B2 | 3/2020 | Pinchuk | |
| 10,603,214 B2 | 3/2020 | Bigler et al. | |
| 10,603,216 B2 | 3/2020 | Kurtz et al. | |
| 10,653,557 B2 | 5/2020 | Rill et al. | |
| 10,674,906 B2 | 6/2020 | Kalina, Jr. et al. | |
| 10,687,978 B2 | 6/2020 | Berlin | |
| 10,702,416 B2 | 7/2020 | Belkin et al. | |
| 10,744,033 B2 | 8/2020 | Baerveldt et al. | |
| 10,744,034 B2 | 8/2020 | Homer | |
| 10,758,418 B2 | 9/2020 | Vold et al. | |
| 10,765,559 B2 | 9/2020 | Berlin | |
| 10,779,988 B2 | 9/2020 | Fu et al. | |
| 10,799,113 B2 | 10/2020 | Vadakke Matham et al. | |
| 10,821,023 B2 | 11/2020 | Raksi | |
| 10,821,024 B2 | 11/2020 | Raksi | |
| 10,888,461 B2 | 1/2021 | Orthaber et al. | |
| 10,898,381 B2 | 1/2021 | Bendett et al. | |
| 11,019,996 B2 | 6/2021 | Kalina, Jr. et al. | |
| 11,019,997 B2 | 6/2021 | Kalina, Jr. et al. | |
| 11,026,860 B2 | 6/2021 | Andersen et al. | |
| 11,039,958 B2 | 6/2021 | Berlin | |
| 11,110,006 B2 | 9/2021 | Raksi | |
| 11,147,708 B2 | 10/2021 | Horvath et al. | |
| 11,166,630 B2 | 11/2021 | Frisken et al. | |
| 11,173,067 B2 | 11/2021 | Raksi | |
| 11,246,754 B2 | 2/2022 | Holland et al. | |
| 11,316,318 B2 | 4/2022 | Yu et al. | |
| 11,376,160 B2 | 7/2022 | Romano et al. | |
| 11,382,794 B2 | 7/2022 | Sacks et al. | |
| 11,395,765 B2 | 7/2022 | Goldshleger et al. | |
| 11,399,981 B2 | 8/2022 | Fu et al. | |
| 11,612,315 B2 | 3/2023 | Delong et al. | |
| 2002/0013572 A1 | 1/2002 | Berlin | |
| 2004/0070761 A1 | 4/2004 | Horvath et al. | |
| 2006/0200113 A1 | 9/2006 | Haffner et al. | |
| 2008/0058781 A1 | 3/2008 | Langeweyde et al. | |
| 2009/0012507 A1 | 1/2009 | Culbertson et al. | |
| 2009/0118718 A1 | 5/2009 | Raksi et al. | |
| 2009/0149840 A1 | 6/2009 | Kurtz | |
| 2009/0149841 A1 | 6/2009 | Kurtz | |
| 2009/0157062 A1 | 6/2009 | Hauger et al. | |
| 2009/0185191 A1 | 7/2009 | Boppart et al. | |
| 2010/0130966 A1 | 5/2010 | Brownell | |
| 2011/0092965 A1 | 4/2011 | Slatkine et al. | |
| 2011/0172649 A1 | 7/2011 | Schuele et al. | |
| 2011/0202046 A1 | 8/2011 | Angeley et al. | |
| 2011/0213664 A1 | 9/2011 | Osterhout et al. | |
| 2011/0214082 A1 | 9/2011 | Osterhout et al. | |
| 2012/0075168 A1 | 3/2012 | Osterhout et al. | |
| 2012/0257167 A1 | 10/2012 | Gille et al. | |
| 2012/0259321 A1 | 10/2012 | Vera et al. | |
| 2012/0283557 A1 | 11/2012 | Berlin | |
| 2012/0303007 A1 | 11/2012 | Loesel et al. | |
| 2013/0085484 A1 | 4/2013 | Van Valen et al. | |
| 2013/0103011 A1 | 4/2013 | Grant et al. | |
| 2013/0197634 A1 | 8/2013 | Palanker et al. | |
| 2013/0237972 A1 | 9/2013 | Raksi | |

(56) References Cited

U.S. PATENT DOCUMENTS

| | | |
|---|---|---|
| 2013/0289450 A1 | 10/2013 | Homer |
| 2014/0128853 A1* | 5/2014 | Angeley ............ A61F 9/00827 606/4 |
| 2014/0142599 A1 | 5/2014 | Jeglorz et al. |
| 2014/0216468 A1 | 8/2014 | Goldshleger et al. |
| 2014/0236066 A1 | 8/2014 | Horvath et al. |
| 2014/0288485 A1 | 9/2014 | Berlin |
| 2014/0354951 A1 | 12/2014 | Izatt et al. |
| 2015/0077528 A1 | 3/2015 | Awdeh |
| 2015/0080783 A1 | 3/2015 | Berlin |
| 2015/0157505 A1 | 6/2015 | Neev |
| 2015/0202083 A1 | 7/2015 | Takeda et al. |
| 2015/0297408 A1 | 10/2015 | Dolzan et al. |
| 2015/0305939 A1 | 10/2015 | Vera et al. |
| 2015/0305940 A1 | 10/2015 | Vera et al. |
| 2015/0313759 A1 | 11/2015 | Vera et al. |
| 2015/0335477 A1 | 11/2015 | Schuele et al. |
| 2015/0359426 A1 | 12/2015 | Buckland et al. |
| 2016/0095751 A1 | 4/2016 | Berlin |
| 2016/0095752 A1 | 4/2016 | Srinivasan et al. |
| 2016/0213512 A1 | 7/2016 | Palanker et al. |
| 2016/0367403 A1 | 12/2016 | Siewert et al. |
| 2017/0020732 A1 | 1/2017 | Berlin |
| 2017/0027437 A1 | 2/2017 | Neal et al. |
| 2017/0042736 A9 | 2/2017 | Berlin |
| 2017/0119579 A9 | 5/2017 | Berlin |
| 2017/0127938 A1 | 5/2017 | Izatt et al. |
| 2017/0202708 A1 | 7/2017 | Berlin |
| 2017/0326003 A1 | 11/2017 | Schuele et al. |
| 2018/0028355 A1 | 2/2018 | Raksi |
| 2018/0207029 A1 | 7/2018 | Herekar et al. |
| 2018/0221205 A1 | 8/2018 | Berlin |
| 2018/0235462 A1 | 8/2018 | Gooi et al. |
| 2018/0360310 A1 | 12/2018 | Berlin |
| 2018/0360655 A1 | 12/2018 | Berlin |
| 2019/0021908 A1 | 1/2019 | Scott |
| 2019/0083313 A1 | 3/2019 | Berlin |
| 2019/0083314 A1 | 3/2019 | Berlin |
| 2019/0117459 A1 | 4/2019 | Berlin |
| 2019/0151146 A1 | 5/2019 | Kim |
| 2019/0240070 A1 | 8/2019 | Schmid et al. |
| 2019/0357768 A1 | 11/2019 | Shareef |
| 2020/0016000 A1 | 1/2020 | Raksi |
| 2020/0016002 A1 | 1/2020 | Raksi |
| 2020/0078216 A1 | 3/2020 | Raksi |
| 2020/0078217 A1 | 3/2020 | Raksi |
| 2020/0078218 A1 | 3/2020 | Holland et al. |
| 2020/0352785 A1 | 11/2020 | Holland et al. |
| 2020/0390605 A1 | 12/2020 | Raksi |
| 2021/0022921 A1 | 1/2021 | Berlin |
| 2021/0052416 A1 | 2/2021 | Herekar et al. |
| 2021/0186752 A1 | 6/2021 | Juhasz et al. |
| 2021/0220176 A1 | 7/2021 | Holland et al. |
| 2021/0235986 A1 | 8/2021 | Juhasz et al. |
| 2021/0298945 A1 | 9/2021 | Juhasz et al. |
| 2021/0307964 A1 | 10/2021 | Holland et al. |
| 2021/0315455 A1 | 10/2021 | Delong et al. |

FOREIGN PATENT DOCUMENTS

| | | |
|---|---|---|
| EP | 1080706 A1 | 3/2001 |
| EP | 1208792 A1 | 5/2002 |
| EP | 1017308 B1 | 6/2003 |
| EP | 2384727 A1 | 11/2011 |
| JP | S58187911 A | 11/1983 |
| JP | H06319765 A | 11/1994 |
| JP | 2001070337 A | 3/2001 |
| JP | 2005508704 A | 4/2005 |
| JP | 2015163193 A | 9/2015 |
| JP | 2016504964 A | 2/2016 |
| JP | 2016105827 A | 6/2016 |
| JP | 2016193033 A | 11/2016 |
| JP | 2019000742 A | 1/2019 |
| WO | 2010060443 A1 | 6/2010 |
| WO | 2013188885 A1 | 12/2013 |
| WO | 2017031570 A1 | 3/2017 |
| WO | 2018049246 A1 | 3/2018 |
| WO | 2019060756 A1 | 3/2019 |
| WO | 2019173759 A1 | 9/2019 |
| WO | 2020018242 A1 | 1/2020 |
| WO | 2022026239 A1 | 2/2022 |

OTHER PUBLICATIONS

Grant, "Tonographic method for measuring the facility and rate of aqueous flow in human eyes" . Arch. Ophthalmol. 44(2), pp. 204-214 (1950).

Jones et al., "New methods of measuring the rate of aqueous flow in man with fluorescein" . Experimental Eye Research, vol. 5:3, pp. 208-220 (Jul. 1966).

Rosenquist et al., "Ouflow resistance of enucleated human eyes at two different perfusion pressures and different extents of trabeculotomy" . Current Eye Research, vol. 8:12, pp. 1233-1240 (1989).

Brubaker, "Goldmann's equation and clinical measures of aqueous dynamics" . Experimental Eye Research, vol. 78, Issue 3, pp. 633-637 (2004).

Johnstone, "The aqueous outflow system as a mechanical pump: evidence from examination of tissue and aqueous movement in human and non-human primates" . J Glaucoma, vol. 13:5, pp. 421-438 (Oct. 2004).

Hann et al. "Anatomic changes in schlemm's canal and collector channels in normal and primary open-angle glaucoma eyes using low and high perfusion pressures" . Glaucoma, vol. 55:9 (Sep. 2014).

Kagemann et al. "Characterisation of Schlemm's canal cross-sectional area." Br J Ophthalmol 2014, 98 (Suppl. II) (Mar. 3, 2014).

McNabb et al. "Complete 360 circumferential gonioscopic optical coherence tomography imaging of the iridocorneal angle." Biomedical Optics Express vol. 6, Issue 4, pp. 1376-1391 (2015).

Xin et al. "OCT study of mechanical properties associated with Trabecular meshwork and collector channel motion in human eyes." PLoS One. 2016; 11(9): e0162048. doi: 10.1371/journal.pone. 0162048 (Sep. 6, 2016).

Junker et al. "Intraoperative optical coherence tomography and ab interno trabecular meshwork surgery with the trabectome." Clin Ophthalmol. 11: 17551760 (Sep. 28, 2017).

Xin et al. "Aqueous outflow regulation: optical coherence tomography implicates pressure-dependent tissue motion." Experimental Eye Research, vol. 158, pp. 171-186 (May 2017).

Dubbelman et al. "The shape of the anterior and posterior surface of the aging human cornea." Vision Research 46 (2006) 993-1001. (Jun. 2015).

PCT/US2022/049587. Int'l Search Report & Written Opinion (dated Mar. 17, 2023).

Lumibird; "Optimis™ Fusion Next Generation SLY/YAG Laser"; Quantel Medical; Cournon d'Auvergne, France; 2020; 6 pgs.

* cited by examiner

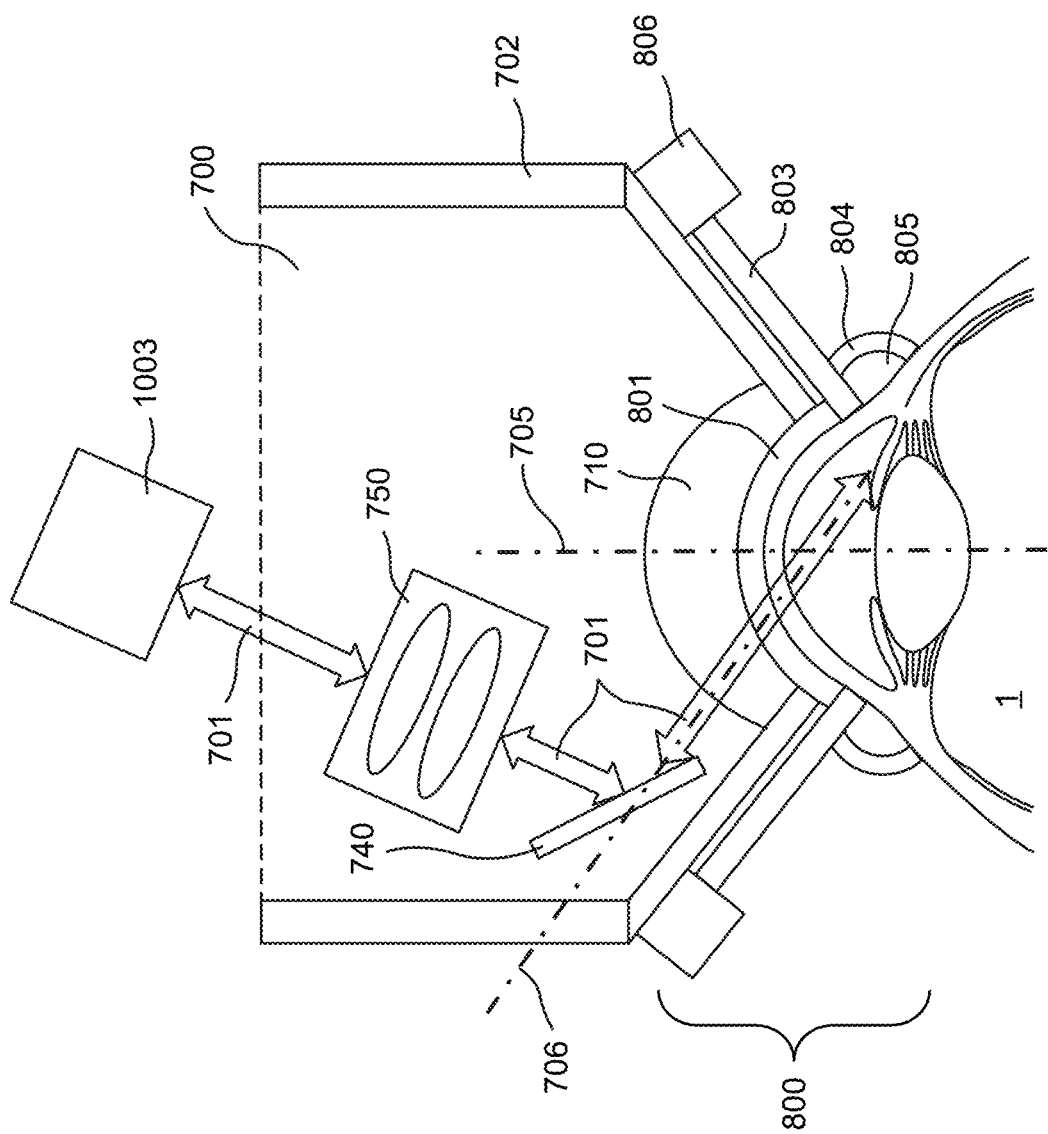

FIG. 29a-1
Legend:
— Natural Anterior
—·— Natural Posterior
--- Docked Anterior
— Docked Posterior
······ Posterior Fit
Note: Posterior Fit curves match Docked Posterior curves
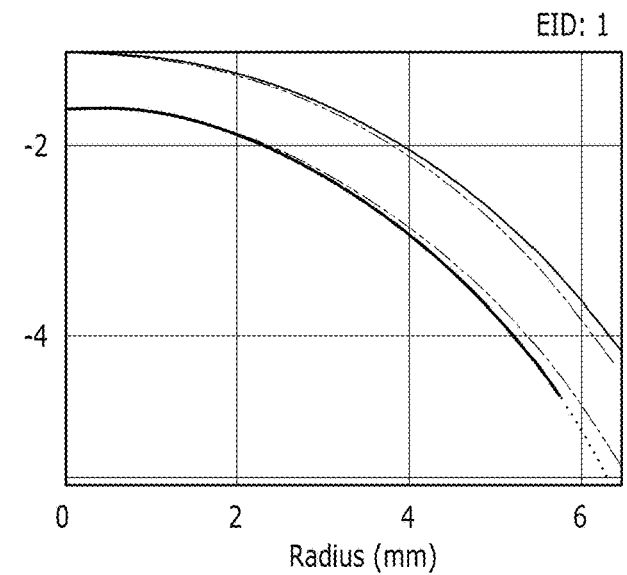
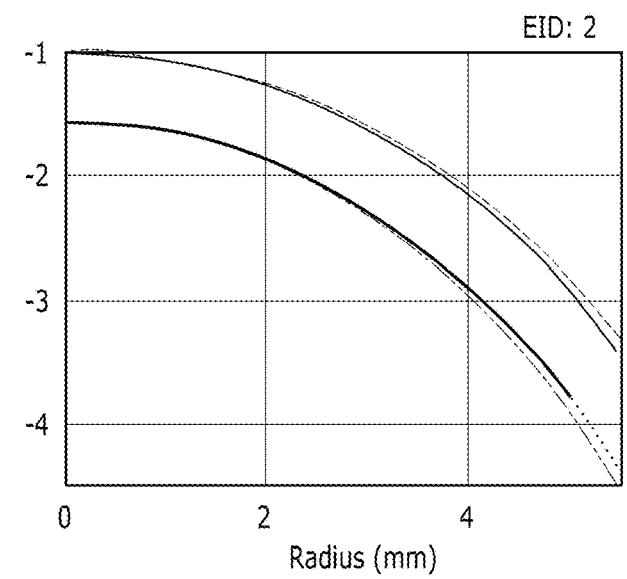
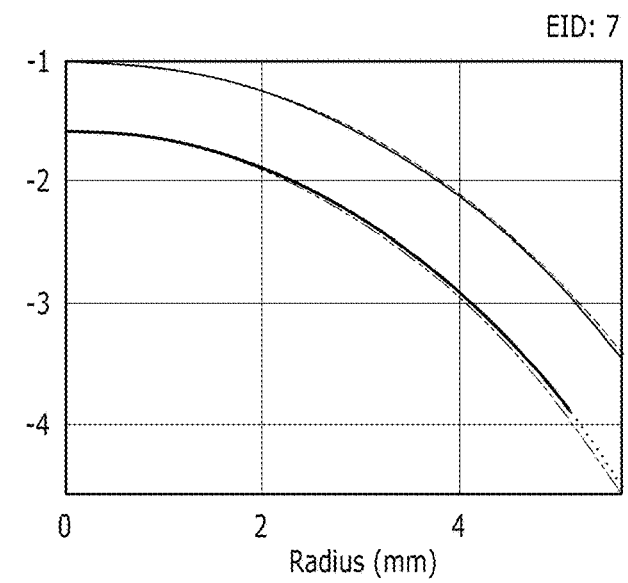

FIG. 29a-3
— Natural Anterior
—·— Natural Posterior
------ Docked Anterior
— Docked Posterior
········ Posterior Fit
Note: Posterior Fit curves match Docked Posterior curves
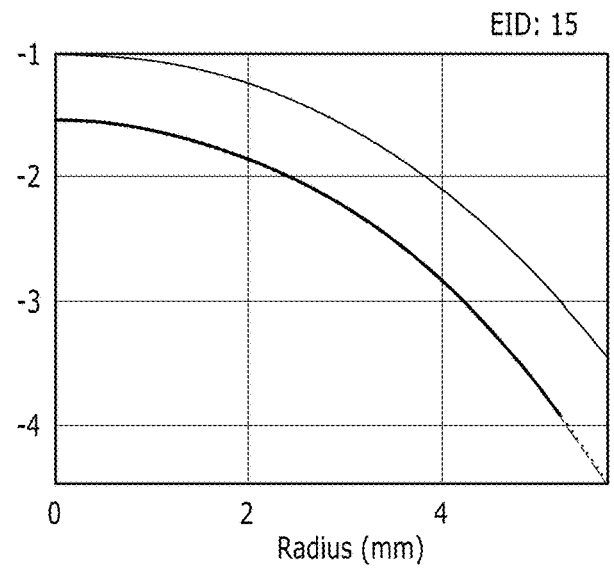
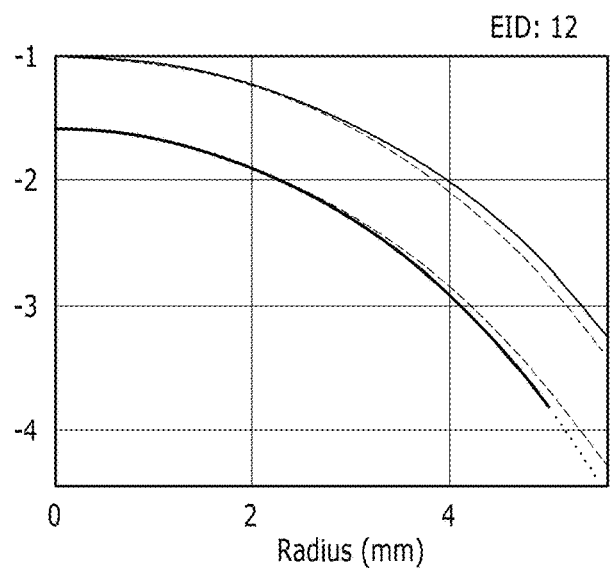
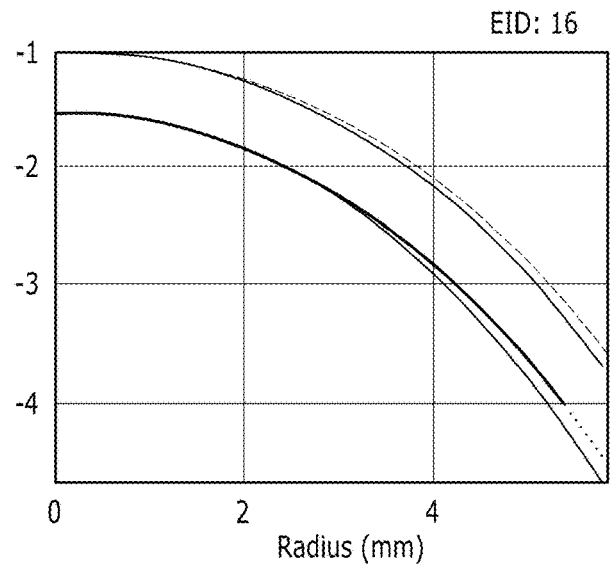

SYSTEM AND METHOD FOR LASER TREATMENT OF OCULAR TISSUE BASED ON PATIENT BIOMETRIC DATA AND APPARATUS AND METHOD FOR DETERMINING LASER ENERGY BASED ON AN ANATOMICAL MODEL

TECHNICAL FIELD

The present disclosure relates generally to the field of medical devices and treatment of diseases in ophthalmology including glaucoma, and more particularly to systems, and methods for laser treatment based on patient biometric data, and apparatuses and methods for determining laser energy based on an anatomical model.

BACKGROUND

Before describing the different types of glaucoma and current diagnosis and treatments options, a brief overview of the anatomy of the eye is provided.

Anatomy of the Eye

With reference to FIGS. 1-3, the outer tissue layer of the eye 1 includes a sclera 2 that provides the structure of the eye's shape. In front of the sclera 2 is a cornea 3 that is comprised of transparent layers of tissue that allow light to enter the interior of the eye. Inside the eye 1 is a crystalline lens 4 that is connected to the eye by fiber zonules 5, which are connected to the ciliary body 6. Between the crystalline lens 4 and the cornea 3 is an anterior chamber 7 that contains a flowing clear liquid called aqueous humor 8. Encircling the perimeter of the crystalline lens 4 is an iris 9 which forms a pupil around the approximate center of the crystalline lens. As shown in FIG. 2, a posterior chamber 23 is an annular volume behind the iris 9 and bounded by the ciliary body 6, fiber zonules 5, and the crystalline lens 4. The vitreous humor 10 is located between the crystalline lens 4 and the retina 11. Light entering the eye is optically focused through the cornea 3 and crystalline lens.

With reference to FIG. 2, the corneoscleral junction of the eye is the portion of the anterior chamber 7 at the intersection of the iris 9, the sclera 2, and the cornea 3. The anatomy of the eye 1 at the corneoscleral junction includes a trabecular meshwork 12. The trabecular meshwork 12 is a fibrous network of tissue that encircles the iris 9 within the eye 1. In simplified, general terms the tissues of the corneoscleral junction are arranged as follows: the iris 9 meets the ciliary body 6, the ciliary body meets with the underside of the scleral spur 14, the top of the scleral spur serves as an attachment point for the bottom of the trabecular meshwork 12. The ciliary body is present mainly in the posterior chamber, but also extends into the very corner of the anterior chamber 7. The network of tissue layers that make up the trabecular meshwork 12 are porous and thus present a pathway for the egress of aqueous humor 8 flowing from the anterior chamber 7. This pathway may be referred to herein as an aqueous humor outflow pathway, an aqueous outflow pathway, or simply an outflow pathway.

Referring to FIG. 3, the pathway formed by the pores in the trabecular meshwork 12 connect to a set of thin, porous tissue layers called the uveal 15, the corneoscleral meshwork 16, and the juxtacanalicular tissue 17. The juxtacanalicular tissue 17, in turn, abuts a structure called Schlemm's canal 18. The Schlemm's canal 18 carries a mixture of aqueous humor 8 and blood from the surrounding tissue to drain into the venous system though a system of collector channels 19. As shown in FIG. 2, the vascular layer of the eye, referred to as the choroid 20, is next to the sclera 2. A space, called the suprachoroidal space 21, may be present between the choroid 20 and the sclera 2. The general region near the periphery of the wedge between the cornea 3 and the iris 9, running circumferentially is called the irido-corneal angle 13. The irido-corneal angle 13 may also be referred to as the corneal angle of the eye or simply the angle of the eye. The ocular tissues illustrated in FIG. 3 are all considered to be within the irido-corneal angle 13.

With reference to FIG. 4, two possible outflow pathways for the movement of aqueous humor 8 include a trabecular outflow pathway 40 and a uveoscleral outflow pathway 42. With additional reference to FIG. 2, aqueous humor 8, which is produced by the ciliary body 6, flows from the posterior chamber 23 through the pupil into the anterior chamber 7, and then exits the eye through one or more of the two different outflow pathways 40, 42. Approximately 90% of the aqueous humor 8 leaves via the trabecular outflow pathway 40 by passing through the trabecular meshwork 12, into the Schlemm's canal 18 and through one or more plexus of collector channels 19 before draining through a drain path 41 into the venous system. Any remaining aqueous humor 8 leaves primarily through the uveoscleral outflow pathway 42. The uveoscleral outflow pathway 42 passes through the ciliary body 6 face and iris root into the suprachoroidal space 21 (shown in FIG. 2). Aqueous humor 8 drains from the suprachoroidal space 21, from which it can be drained through the sclera 2.

The intra-ocular pressure of the eye depends on the aqueous humor 8 outflow through the trabecular outflow pathway 40 and the resistance to outflow of aqueous humor through the trabecular outflow pathway. The intra-ocular pressure of the eye is largely independent of the aqueous humor 8 outflow through the uveoscleral outflow pathway 42. Resistance to the outflow of aqueous humor 8 through the trabecular outflow pathway 40 may lead to elevated intra-ocular pressure of the eye, which is a widely recognized risk factor for glaucoma. Resistance through the trabecular outflow pathway 40 may increase due to a collapsed or malfunctioning Schlemm's canal 18 and trabecular meshwork 12.

Referring to FIG. 5, as an optical system, the eye 1 is represented by an optical model described by idealized centered and rotationally symmetrical surfaces, entrance and exit pupils, and six cardinal points: object and image space focal points, first and second principal planes, and first and second nodal points. Angular directions relative to the human eye are often defined with respect to an optical axis 24, a visual axis 26, a pupillary axis 28 and a line of sight 29 of the eye. The optical axis 24 is the symmetry axis, the line connecting the vertices of the idealized surfaces of the eye. The visual axis 26 connects the foveal center 22 with the first and second nodal points to the object. The line of sight 29 connects the fovea through the exit and entrance pupils to the object. The pupillary axis 28 is normal to the anterior surface of the cornea 3 and is directed to the center of the entrance pupil. These axes of the eye differ from one another only by a few degrees and fall within a range of what is generally referred to as the direction of view.

Glaucoma

Glaucoma is a group of diseases that can harm the optic nerve and cause vision loss or blindness. It is the leading cause of irreversible blindness. Approximately 80 million people are estimated to have glaucoma worldwide and of these, approximately 6.7 million are bilaterally blind. More than 2.7 million Americans over age 40 have glaucoma. Symptoms start with loss of peripheral vision and can progress to blindness.

There are two forms of glaucoma, one is referred to as closed-angle glaucoma, the other as open-angled glaucoma. With reference to FIGS. 1-4, in closed-angle glaucoma, the iris 9 in a collapsed anterior chamber 7 may obstruct and close off the flow of aqueous humor 8. In open-angle glaucoma, which is the more common form of glaucoma, the permeability of ocular tissue may be affected by irregularities in the juxtacanalicular tissue 17 and inner wall of Schlemm's canal 18a, and blockage of tissue in the irido-corneal angle 13 along the trabecular outflow pathway 40.

As previously stated, elevated intra-ocular pressure (IOP) of the eye, which damages the optic nerve, is a widely recognized risk factor for glaucoma. However, not every person with increased eye pressure will develop glaucoma, and glaucoma can develop without increased eye pressure. Nonetheless, it is desirable to reduce elevated IOP of the eye to reduce the risk of glaucoma.

Methods of diagnosing conditions of the eye of a patient with glaucoma include visual acuity tests and visual field tests, dilated eye exams, tonometry, i.e. measuring the intra-ocular pressure of the eye, and pachymetry, i.e. measuring the thickness of the cornea. Deterioration of vision starts with the narrowing of the visual field and progresses to total blindness. Imaging methods include slit lamp examination, observation of the irido-corneal angle with a gonioscopic lens and optical coherence tomography (OCT) imaging of the anterior chamber and the retina.

Once diagnosed, some clinically proven treatments are available to control or lower the intra-ocular pressure of the eye to slow or stop the progress of glaucoma. The most common treatments include: 1) medications, such as eye drops or pills, 2) laser surgery, and 3) traditional surgery. Treatment usually begins with medication. However, the efficacy of medication is often hindered by patient non-compliance. When medication does not work for a patient, laser surgery is typically the next treatment to be tried. Traditional surgery is invasive, more high risk than medication and laser surgery, and has a limited time window of effectiveness. Traditional surgery is thus usually reserved as a last option for patients whose eye pressure cannot be controlled with medication or laser surgery.

Laser Surgery

With reference to FIG. 2, laser surgery for glaucoma targets the trabecular meshwork 12 to decrease aqueous humor 8 flow resistance. Common laser treatments include Argon Laser Trabeculoplasty (ALT), Selective Laser Trabeculoplasty (SLT) and Excimer Laser Trabeculostomy (ELT).

ALT was the first laser trabeculoplasty procedure. During the procedure, an argon laser of 514 nm wavelength is applied to the trabecular meshwork 12 around 180 degrees of the circumference of the irido-corneal angle 13. The argon laser induces a thermal interaction with the ocular tissue that produces openings in the trabecular meshwork 12. ALT, however, causes scarring of the ocular tissue, followed by inflammatory responses and tissue healing that may ultimately close the opening through the trabecular meshwork 12 formed by the ALT treatment, thus reducing the efficacy of the treatment. Furthermore, because of this scarring, ALT therapy is typically not repeatable.

SLT is designed to lower the scarring effect by selectively targeting pigments in the trabecular meshwork 12 and reducing the amount of heat delivered to surrounding ocular tissue. During the procedure, a solid-state laser of 532 nm wavelength is applied to the trabecular meshwork 12 between 180 to 360 degrees around the circumference of the irido-corneal angle 13 to remove the pigmented cells lining the trabeculae which comprise the trabecular meshwork. The collagen ultrastructure of the trabecular meshwork is preserved during SLT. 12. SLT treatment can be repeated, but subsequent treatments have lower effects on IOP reduction.

ELT uses a 308 nm wavelength ultraviolet (UV) excimer laser and non-thermal interaction with ocular tissue to treat the trabecular meshwork 12 and inner wall of Schlemm's canal 18a in a manner that does not invoke a healing response. Therefore, the IOP lowering effect lasts longer. However, because the UV light of the laser cannot penetrate deep into the eye, the laser light is delivered to the trabecular meshwork 12 via an optical fiber inserted into the eye 1 through an opening and the fiber is brought into contact with the trabecular meshwork. The procedure is highly invasive and is generally practiced simultaneously with cataract procedures when the eye is already surgically open. Like ALT and SLT, ELT also lacks control over the amount of IOP reduction.

The use of femtosecond lasers for surgery of the trabecular meshwork in the treatment of glaucoma is new. Femtosecond laser pulses treat tissue by a process called photodisruption in which tissue at the focus of a beam is disrupted to elemental gas. The intent of treating the tissue in this manner is to create an aperture through which the intraocular pressure can be reduced. The "cutting efficiency" is a function of laser fluence, which is the ratio of energy per pulse to the area over which the energy is delivered, spot size. Once the laser fluence exceeds a breakdown threshold value, the tissue within a volume specified by the laser focus spot size is disrupted. If the laser fluence is less than the breakdown threshold, the focused laser does not affect the tissue. It is generally accepted that the breakdown threshold for ocular tissue is approximately 0.8 to 1.2 $J/cm^2$.

Femtosecond lasers treat the trabecular meshwork by focusing a beam of femtosecond laser pulse from the cornea, through the anterior chamber, and into a spot on the irido-corneal angle. The size (diameter) of the spot changes depending upon the amount of optical aberrations introduced into the beam trajectory as it enters, and passes through, the eye to the trabecular meshwork. The location of the trabecular meshwork varies across the patient population due to anatomical differences in corneal anterior and posterior shape, corneal thickness, and corneal diameter. There is a unique beam trajectory for each patient and leading to a unique set of optical aberrations. Therefore, there is a spot size variation across the patient population—and for a fixed energy—a different fluence, resulting in varying cutting efficiency.

Due to this spot size variation and resulting variation in cutting efficiency, what is needed are systems, apparatuses, and method for laser surgery treatment of glaucoma that provide homogeneous cutting efficiency across the patient population.

SUMMARY

The present disclosure relates to a method of photodisrupting a target volume of ocular tissue with a laser. The target volume of ocular tissue is associated with an eye of a patient. The method includes placing a focus of a laser at an initial location within the target volume of ocular tissue; and applying photodisruptive energy by the laser at the initial location in accordance with an energy parameter that is based on the initial location of the focus within the target volume of ocular tissue.

The present disclosure also relates to a system for photodisrupting a target volume of ocular tissue with a laser. The target volume of ocular tissue is associated with an eye of a patient. The system includes a first optical subsystem, a second optical subsystem, and a control system coupled to the first optical subsystem and the second optical subsystem. The first optical subsystem includes one or more optical components configured to be coupled to the eye. The second optical subsystem includes a laser source configured to output a laser beam, and a plurality of components configured to one or more of focus, scan, and direct the laser beam through the one or more optical components, toward the target volume of ocular tissue. The control system is configured to control the focusing and the scanning of the laser beam to: place a focus of the laser beam at an initial location within the target volume of ocular tissue, and apply photodisruptive energy by the laser beam at the initial location in accordance with an energy parameter that is based on the initial location of the focus within the target volume of ocular tissue.

The present disclosure also relates to a method of generating a look-up table for use in determining an energy parameter for photodisrupting ocular tissue with a laser. The method includes determining a plurality of individual spot size distributions, wherein each of the plurality of individual spot size distributions is based on a different set of simulated data and includes an expected spot size of a focus of a laser beam at each of a plurality of locations within a modeled target volume of ocular tissue. The method also includes combining the plurality of individual spot size distributions to obtain a final spot size distribution that includes a final expected spot size of the focus at the plurality of locations of the focus within the modeled target volume of ocular tissue. The method further includes assigning an energy value to the plurality of locations of the focus within the modeled target volume of ocular tissue based on the final expected spot size at that location.

The present disclosure also relates to an apparatus for generating a look-up table for use in determining an energy parameter for photodisrupting ocular tissue with a laser. The apparatus includes a memory and a processing unit coupled to the memory. The processing unit is configured to determine a plurality of individual spot size distributions, wherein each of the plurality of individual spot size distributions is based on a different set of simulated data and includes an expected spot size of a focus of a laser beam at each of a plurality of locations within a modeled target volume of ocular tissue. The processing unit is further configured to combine the plurality of individual spot size distributions to obtain a final spot size distribution that includes a final expected spot size of the focus at the plurality of locations of the focus within the modeled target volume of ocular tissue. The processor is also configured to assign an energy value to the plurality of locations of the focus within the modeled target volume of ocular tissue based on the final expected spot size at that location.

It is understood that other aspects of apparatuses and methods will become apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

Various aspects of systems, apparatuses, and methods will now be presented in the detailed description by way of example, and not by way of limitation, with reference to the accompanying drawings, wherein:

FIGS. 9a and 9b are schematic illustrations of the focusing objective head of the integrated surgical system of FIG. 7 coupled to (FIG. 9a) and decoupled from (FIG. 9b) the patient interface of the integrated surgical system of FIG. 7.

FIG. 29a-1 through 29a-3 is a set of graphs, each graph illustrating a natural anterior and posterior corneal curves, deformed (or docked) anterior and posterior corneal curves and a fitted deformed posterior corneal curve generated by the look up table generator based on simulated data. Note that the posterior fitted curves essentially match the deformed posterior curves.

DETAILED DESCRIPTION

Disclosed herein are systems, apparatuses, and methods for safely and effectively reducing intra-ocular pressure (IOP) in the eye to either treat or reduce the risk of glaucoma. The systems, apparatuses, and methods enable access to the irido-corneal angle of the eye and integrate laser surgery techniques with high resolution imaging to precisely diagnose, locate, and treat abnormal ocular tissue conditions within the irido-corneal angle that may be causing elevated IOP.

An integrated surgical system disclosed herein is configured to reduce intraocular pressure in an eye having a cornea, an anterior chamber, and an irido-corneal angle comprising an aqueous humor outflow pathway formed of a trabecular meshwork, a Schlemm's canal, and one or more collector channels branching from the Schlemm's canal. The integrated surgical system includes a first optical subsystem and a second optical subsystem. The first optical subsystem includes a window configured to be coupled to the cornea and an exit lens configured to be coupled to the window. The second optical subsystem includes an optical coherence tomography (OCT) imaging apparatus configured to output an OCT beam, a laser source configured to output a laser beam, and a plurality of components, e.g., lenses and mirrors, configured to condition, combine, or direct the OCT beam and the laser beam toward the first optical subsystem.

The integrated surgical system also includes a control system coupled to the OCT imaging apparatus, the laser source, and the second optical subsystem. The controller is configured to instruct the OCT imaging apparatus to output an OCT beam and the laser source to output a laser beam, for delivery through the cornea, and the anterior chamber into the irido-corneal angle. In one configuration, the control system controls the second optical subsystem, so the OCT beam and the laser beam are directed into the first optical subsystem along a second optical axis that is offset from the first optical axis and that extends into the irido-corneal angle along an angled beam path 30.

Figure 2:
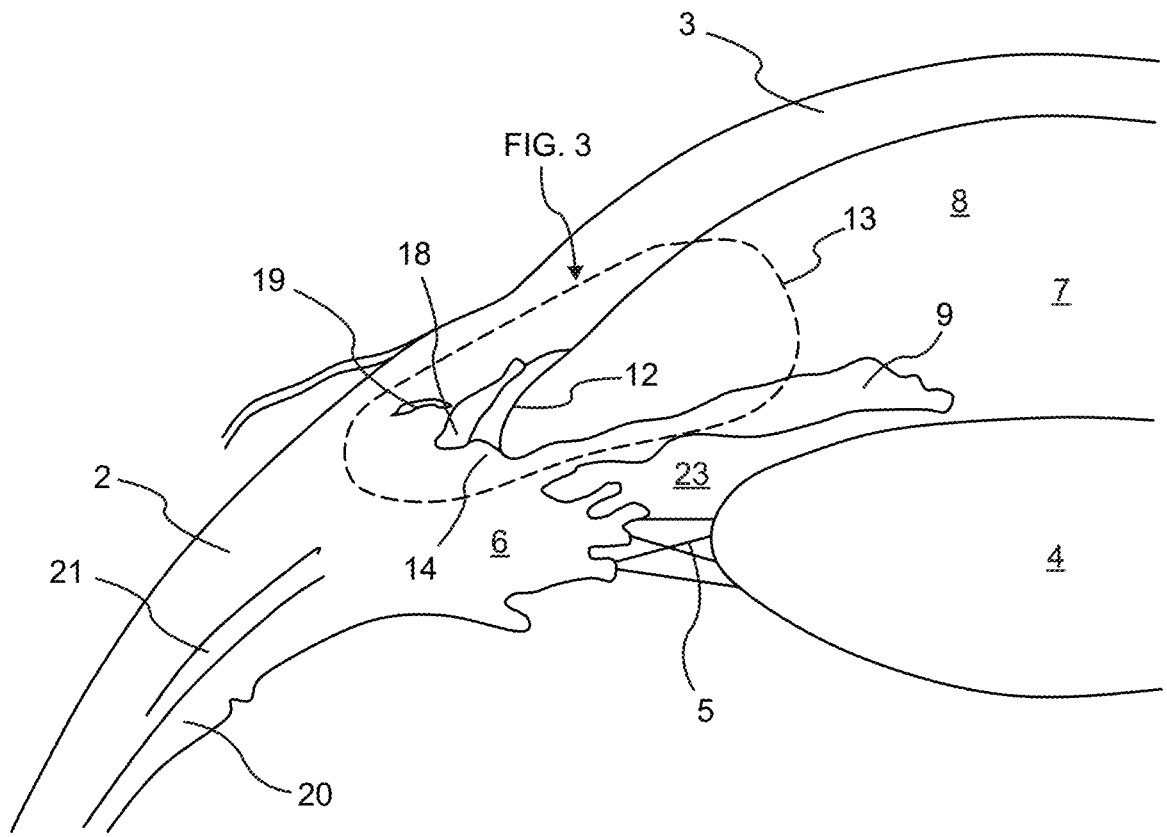
FIG. 2 is a sectional schematic illustration of the irido-corneal angle of the eye of FIG. 1.

Directing each of an OCT beam and a laser beam along the same second optical axis into the irido-corneal angle of the eye is beneficial in that it enables direct application of the result of the evaluation of the condition into the treatment plan and surgery with precision in one clinical setting. Furthermore, combining OCT imaging and laser treatment allows targeting the ocular tissue with precision not available with any existing surgical systems and methods. Surgical precision afforded by the integrated surgical system allows for the affecting of only the targeted tissue of microscopic size and leaves the surrounding tissue intact. The microscopic size scale of the affected ocular tissue to be treated in the irido-corneal angle of the eye ranges from a few micrometers to a few hundred micrometers. For example, with reference to FIGS. 2 and 3, the cross-sectional size of the normal Schlemm's canal 18 is an oval shape of a few tens of micrometers by a few hundred micrometers. The diameter of collector channels 19 and veins is a few tens of micrometers. The thickness of the juxtacanalicular tissue 17 is a few micrometers, the thickness of the trabecular meshwork 12 is around a hundred micrometers.

The control system of the integrated surgical system is further configured to instruct the laser source to modify a volume of ocular tissue within the outflow pathway to reduce a pathway resistance present in one or more of the trabecular meshwork, the Schlemm's canal, and the one or more collector channels by applying the laser beam to ocular tissue defining the volume to thereby cause photo-disruptive interaction with the ocular tissue to reduce the pathway resistance or create a new outflow pathway.

The laser source may be a femtosecond laser or a picosecond laser. Such lasers provide non-thermal photo-disruption interaction with ocular tissue to avoid thermal damage to surrounding tissue. Further, unlike other surgical methods, with femtosecond laser treatment opening surface incisions penetrating the eye can be avoided, enabling a non-invasive treatment. Instead of performing the treatment in a sterile surgical room, the non-invasive treatment can be performed in a non-sterile outpatient facility.

The integrated surgical system may also include an optical coherence tomography (OCT) imaging apparatus for imaging the target volume of ocular tissue. An additional imaging component may be included to provide direct visual observation of the irido-corneal angle along an angle of visual observation. For example, a microscope or imaging camera may be included to assist the surgeon in the process of docking the eye to the patient interface or an immobilizing device, locating ocular tissues in the eye and observing the progress of the surgery. The angle of visual observation can also be along the angled beam path 30 to the irido-corneal angle 13 through the cornea 3 and the anterior chamber 7.

Images from the OCT imaging apparatus and the additional imaging component providing visual observation, e.g. microscope, are combined on a display device such as a computer monitor. Different images can be registered and overlaid on a single window, enhanced, processed, differentiated by false color for easier understanding. Certain features are computationally recognized by a computer processor, image recognition and segmentation algorithm can be enhanced, highlighted, marked for display. The geometry of the treatment plan can also be combined and registered with imaging information on the display device and marked up with geometrical, numerical and textual information. The same display can also be used for user input of numerical, textual and geometrical nature for selecting, highlighting and marking features, inputting location information for surgical targeting by keyboard, mouse, cursor, touchscreen, audio or other user interface devices.

OCT Imaging

The main imaging component of the integrated surgical system disclosed herein is an OCT imaging apparatus. OCT technology may be used to diagnose, locate and guide laser surgery directed to the irido-corneal angle of the eye. For example, with reference to FIGS. 1-3, OCT imaging may be used to determine the structural and geometrical conditions of the anterior chamber 7, to assess possible obstruction of the trabecular outflow pathway 40 and to determine the accessibility of the ocular tissue for treatment. As previously described, the iris 9 in a collapsed anterior chamber 7 may obstruct and close off the flow of aqueous humor 8, resulting in closed-angle glaucoma. In open-angle glaucoma, where the macroscopic geometry of the angle is normal, the permeability of ocular tissue may be affected, by blockage of tissue along the trabecular outflow pathway 40 or by the collapse of the Schlemm's canal 18 or collector channels 19.

OCT imaging can provide the necessary spatial resolution, tissue penetration and contrast to resolve microscopic details of ocular tissue. When scanned, OCT imaging can provide two-dimensional (2D) cross-sectional images of the ocular tissue. As another aspect of the integrated surgical system, 2D cross-sectional images may be processed and analyzed to determine the size, shape and location of structures in the eye for surgical targeting. It is also possible to reconstruct three-dimensional (3D) images from a multitude of 2D cross-sectional images but often it is not necessary. Acquiring, analyzing and displaying 2D images is faster and can still provide all information necessary for precise surgical targeting.

OCT is an imaging modality capable of providing high resolution images of materials and tissue. Imaging is based on reconstructing spatial information of the sample from spectral information of scattered light from within the sample. Spectral information is extracted by using an interferometric method to compare the spectrum of light entering the sample with the spectrum of light scattered from the sample. Spectral information along the direction that light is propagating within the sample is then converted to spatial information along the same axis via the Fourier transform. Information lateral to the OCT beam propagation is usually collected by scanning the beam laterally and repeated axial probing during the scan. 2D and 3D images of the samples can be acquired this way. Image acquisition is faster when the interferometer is not mechanically scanned in a time domain OCT, but interference from a broad spectrum of light is recorded simultaneously. This implementation is called a spectral domain OCT. Faster image acquisition may also be obtained by scanning the wavelength of light rapidly from a wavelength scanning laser in an arrangement called a swept-source OCT.

The axial spatial resolution limit of the OCT is inversely proportional to the bandwidth of the probing light used. Both spectral domain and swept source OCTs are capable of axial spatial resolution below 5 micrometers (m) with sufficiently broad bandwidth of 100 nanometers (nm) or more. In the spectral domain OCT, the spectral interference pattern is recorded simultaneously on a multichannel detector, such as a charge coupled device (CCD) or complementary metal oxide semiconductor (CMOS) camera, while in the swept source OCT the interference pattern is recorded in sequential time steps with a fast optical detector and electronic digitizer. There is some acquisition speed advantage of the swept source OCT but both types of systems are evolving and improving rapidly, and resolution and speed is sufficient for purposes of the integrated surgical system disclosed herein. Stand-alone OCT systems and OEM components are now commercially available from multiple vendors, such as Optovue Inc., Fremont, CA, Topcon Medical Systems, Oakland, NJ, Carl Zeiss Meditec AG, Germany, Nidek, Aichi, Japan, Thorlabs, Newton, NJ, Santec, Aichi, Japan, Axsun, Billercia, MA, and other vendors.

Femtosecond Laser Source

The preferred surgical component of the integrated surgical system disclosed herein is a femtosecond laser. A femtosecond laser provides highly localized, non-thermal photo-disruptive laser-tissue interaction with minimal collateral damage to surrounding ocular tissue. Photo-disruptive interaction of the laser is utilized in optically transparent tissue. The principal mechanism of laser energy deposition into the ocular tissue is not by absorption but by a highly nonlinear multiphoton process. This process is effective only at the focus of the pulsed laser where the peak intensity is high. Regions where the beam is traversed but not at the focus are not affected by the laser. Therefore, the interaction region with the ocular tissue is highly localized both transversally and axially along the laser beam. The process can also be used in weakly absorbing or weakly scattering tissue. While femtosecond lasers with photo-disruptive interactions have been successfully used in ophthalmic surgical systems and commercialized in other ophthalmic laser procedures, none have been used in an integrated surgical system that accesses the irido-corneal angle.

In known refractive procedures, femtosecond lasers are used to create corneal flaps, pockets, tunnels, arcuate incisions, lenticule shaped incisions, partial or fully penetrating corneal incisions for keratoplasty. For cataract procedures the laser creates a circular cut on the capsular bag of the eye for capsulotomy and incisions of various patterns in the lens for breaking up the interior of the crystalline lens to smaller fragments to facilitate extraction. Entry incisions through the cornea opens the eye for access with manual surgical devices and for insertions of phacoemulsification devices and intra-ocular lens insertion devices. Several companies have commercialized such surgical systems, among them the IntraLase system now available from Johnson & Johnson Vision, Santa Ana, CA, The LenSx and WaveLight systems from Alcon, Fort Worth, TX the Lensar Laser System from Lensar, Inc. Orlando, FL; the family of Femto Lasers from Ziemer Ophthalmics, Alton IL; the Victus Femtosecond Laser Platform from Bausch and Lomb, Rochester, NY; and the Catalys Precision Laser System from Johnson & Johnson, Santa Ana, CA.

These existing systems are developed for their specific applications, for surgery in the cornea, and the crystalline lens and its capsular bag and are not capable of performing surgery in the irido-corneal angle 13 for several reasons. First, the irido-corneal angle 13 is not accessible with these surgical laser systems because the irido-corneal angle is too far out in the periphery and is outside of surgical range of these systems. Second, the angle of the laser beam from these systems, which is along the optical axis 24 to the eye 1, is not appropriate for reaching the irido-corneal angle 13, where there is significant scattering and optical distortion at the applied wavelength. Third, any imaging capabilities these systems may have do not have the accessibility, penetration depth and resolution to image the tissue along the trabecular outflow pathway 40 with sufficient detail and contrast.

In accordance with the integrated surgical system disclosed herein, clear access to the irido-corneal angle 13 is provided along the angled beam path 30. The tissue, e.g., cornea 3 and the aqueous humor 8 in the anterior chamber 7, along this angled beam path 30 is transparent for wavelengths from approximately 400 nm to 2500 nm and femtosecond lasers operating in this region can be used. Such mode locked lasers work at their fundamental wavelength with Titanium, Neodymium or Ytterbium active material. Non-linear frequency conversion techniques known in the art, frequency doubling, tripling, sum and difference frequency mixing techniques, optical parametric conversion can convert the fundamental wavelength of these lasers to practically any wavelength in the above mentioned transparent wavelength range of the cornea.

Existing ophthalmic surgical systems apply lasers with pulse durations longer than 1 ns have higher photo-disruption threshold energy, require higher pulse energy and the dimension of the photo-disruptive interaction region is larger, resulting in loss of precision of the surgical treatment. When treating the irido-corneal angle 13, however, higher surgical precision is required. To this end, the integrated surgical system may be configured to apply lasers with pulse durations from 10 femtosecond (fs) to 1 nanosecond (ns) for generating photo-disruptive interaction of the laser beam with ocular tissue in the irido-corneal angle 13. While lasers with pulse durations shorter than 10 fs are available, such laser sources are more complex and more expensive. Lasers with the described desirable characteristics, e.g., pulse durations from 10 femtosecond (fs) to 1 nanosecond (ns), are commercially available from multiple vendors, such as Newport, Irvine, CA, Coherent, Santa Clara, CA, Amplitude Systems, Pessac, France, NKT Photonics, Birkerod, Denmark, and other vendors.

Accessing the Irido-Corneal Angle

Figure 6:
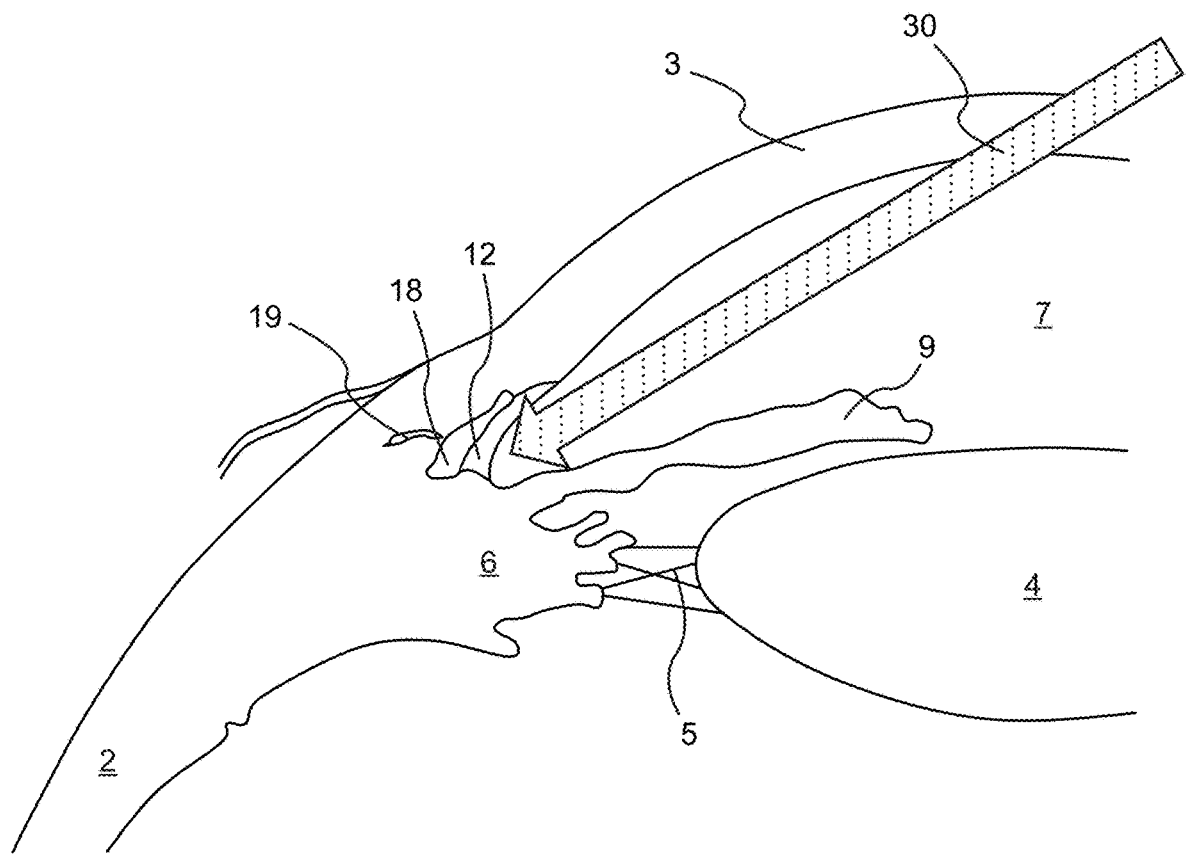
FIG. 6 is a sectional schematic illustration of an angled beam path along which one or more light beams may access the irido-corneal angle of the eye.

An important feature afforded by the integrated surgical system is access to the targeted ocular tissue in the irido-corneal angle 13. With reference to FIG. 6, the irido-corneal angle 13 of the eye may be accessed via the integrated surgical system along an angled beam path 30 passing through the cornea 3 and through the aqueous humor 8 in the anterior chamber 7. For example, one or more of an imaging beam, e.g., an OCT beam and/or a visual observation beam, and a laser beam may access the irido-corneal angle 13 of the eye along the angled beam path 30.

An optical system disclosed herein is configured to direct a light beam to an irido-corneal angle 13 of an eye along an angled beam path 30. The optical system includes a first optical subsystem and a second optical subsystem. The first optical subsystem includes a window formed of a material with a refractive index $n_w$ and has opposed concave and convex surfaces. The first optical subsystem also includes an exit lens formed of a material having a refractive index $n_x$. The exit lens also has opposed concave and convex surfaces. The concave surface of the exit lens is configured to couple to the convex surface of the window to define a first optical axis extending through the window and the exit lens. The concave surface of the window is configured to detachably couple to a cornea of the eye with a refractive index $n_c$ such that, when coupled to the eye, the first optical axis is generally aligned with the direction of view of the eye.

The second optical subsystem is configured to output a light beam, e.g., an OCT beam or a laser beam. The optical system is configured so that the light beam is directed to be incident at the convex surface of the exit lens along a second optical axis at an angle α that is offset from the first optical axis. The respective geometries and respective refractive indices $n_x$, and $n_w$ of the exit lens and window are configured to compensate for refraction and distortion of the light beam by bending the light beam so that it is directed through the cornea 3 of the eye toward the irido-corneal angle 13. More specifically, the first optical system bends the light beam to that the light beam exits the first optical subsystem and enters the cornea 3 at an appropriate angle so that the light beam progresses through the cornea and the aqueous humor 8 in a direction along the angled beam path 30 toward the irido-corneal angle 13.

Accessing the irido-corneal angle 13 along the angled beam path 30 provides several advantages. An advantage of this angled beam path 30 to the irido-corneal angle 13 is that the OCT beam and laser beam passes through mostly clear tissue, e.g., the cornea 3 and the aqueous humor 8 in the anterior chamber 7. Thus, scattering of these beams by tissue is not significant. With respect to OCT imaging, this enables the use of shorter wavelength, less than approximately 1 micrometer, for the OCT to achieve higher spatial resolution. An additional advantage of the angled beam path 30 to the irido-corneal angle 13 through the cornea 3 and the anterior chamber 7 is the avoidance of direct laser beam or OCT beam light illuminating the retina 11. As a result, higher average power laser light and OCT light can be used for imaging and surgery, resulting in faster procedures and less tissue movement during the procedure.

Another important feature provided by the integrated surgical system is access to the targeted ocular tissue in the irido-corneal angle 13 in a way that reduces beam discontinuity. To this end, the window and exit lens components of the first optical subsystem are configured to reduce the discontinuity of the optical refractive index between the cornea 3 and the neighboring material and facilitate entering light through the cornea at a steep angle.

Having thus generally described the integrated surgical system and some of its features and advantages, a more detailed description of the system and its component parts follows.

Integrated Surgical System

In the following description, the term "beam" may—depending on the context—refer to one of a laser beam, an OCT beam, an illumination beam, an observation beam, an illumination/observation beam, or a visual beam. The term "colinear beams" refers to two or more different beams that are combined by optics of the integrated surgical system 1000 to share a same path to a same target location of the eye as they enter the eye. The term "non-colinear beams" refers to two or more different beams that have different paths into the eye. The term "co-targeted beams" refers to two or more different beams that have different paths into the eye but that target a same location of the eye. In colinear beams, the different beams may be combined to share a same path into the eye by dichroic or polarization beam splitters, and delivered along a same optical path through a multiplexed delivery of the different beams. In non-colinear beams, the different beams are delivered into the eye along different optical paths that are separated spatially or by an angle between them. In the description to follow, any of the foregoing beams or combined beams may be generically referred to as a light beam. The terms distal and proximal may be used to designate the direction of travel of a beam, or the physical location of components relative to each other within the integrated surgical system. The distal direction refers to a direction toward the eye; thus an OCT beam output by the OCT imaging apparatus moves in the distal direction toward the eye. The proximal direction refers to a direction away from the eye; thus an OCT return beam from the eye moves in the proximal direction toward the OCT imaging apparatus.

Figure 7:
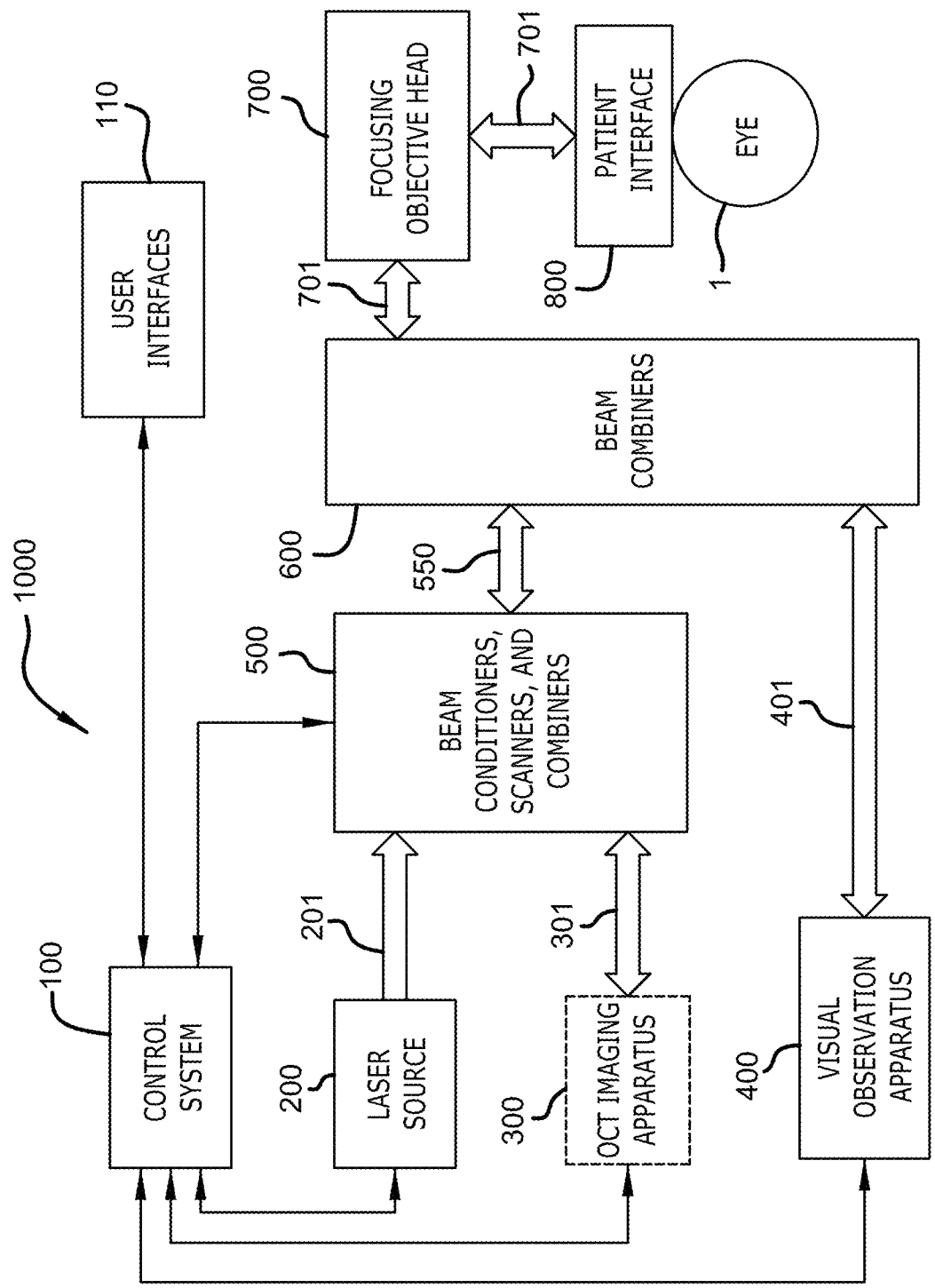
FIG. 7 is a block diagram of an integrated surgical system for non-invasive glaucoma surgery including a control system, a femtosecond laser source, an OCT imaging apparatus, a microscope, beam conditioners and scanners, beam combiners, a focusing objective head, and a patient interface.

With reference to FIG. 7, an integrated surgical system 1000 for non-invasive glaucoma surgery includes a control system 100, a surgical component 200, a first imaging component 300 and an optional second imaging component 400. In the embodiment of FIG. 7, the surgical component 200 is a femtosecond laser source, the first imaging component 300 is an OCT imaging apparatus, and the optional second imaging component 400 is a visual observation apparatus, e.g., a microscope, for direct viewing or viewing with a camera. Other components of the integrated surgical system 1000 include beam conditioners and scanners 500, beam combiners 600, a focusing objective head 700, and a patient interface 800.

The control system 100 may be a single computer or and plurality of interconnected computers configured to control the hardware and software components of the other components of the integrated surgical system 1000. A user interface 110 of the control system 100 accepts instructions from a user and displays information for observation by the user. Input information and commands from the user include but are not limited to system commands, motion controls for docking the patient's eye to the system, selection of pre-programmed or live generated surgical plans, navigating through menu choices, setting of surgical parameters, responses to system messages, determining and acceptance of surgical plans and commands to execute the surgical plan. Outputs from the system towards the user includes but are not limited to display of system parameters and messages, display of images of the eye, graphical, numerical and textual display of the surgical plan and the progress of the surgery.

The control system 100 is connected to the other components 200, 300, 400, 500 of the integrated surgical system 1000. Control signals from the control system 100 to the femtosecond laser source 200 function to control internal and external operation parameters of the laser source, including for example, power, repetition rate and beam shutter. Control signals from the control system 100 to the OCT imaging apparatus 300 function to control OCT beam scanning parameters, and the acquiring, analyzing and displaying of OCT images.

Laser beams 201 from the femtosecond laser source 200 and OCT beams 301 from the OCT imaging apparatus 300 are directed towards a unit of beam conditioners and scanners 500. Beam conditioners set the basic beam parameters, beam size, divergence. Beam conditioners may also include additional functions, setting the beam power or pulse energy and shutter the beam to turn it on or off. Different kind of scanners can be used for the purpose of scanning the laser beam 201 and the OCT beam 301. For scanning transversal to a beam 201, 301, angular scanning galvanometer scanners are available for example from Cambridge Technology, Bedford, MA, Scanlab, Munich, Germany.

To optimize scanning speed, the scanner mirrors are typically sized to the smallest size, which still support the required scanning angles and numerical apertures of the beams at the target locations. The ideal beam size at the scanners is typically different from the beam size of the laser beam 201 or the OCT beam 301, and different from what is needed at the entrance of a focusing objective head 700. Therefore, beam conditioners are applied before, after or in between individual scanners. The beam conditioner and scanners 500 includes scanners for scanning the beam transversally and axially. Axial scanning changes the depth of the focus at the target region. Axial scanning can be performed by moving a lens axially in the beam path with a servo or stepper motor.

Beam combiners, such as dichroic, polarization or other kind of beam combiners, colinearly combine the laser beam 201 and the OCT beam 301. In some embodiments, the laser beam 201 and the OCT beam 301 may be combined and then scanned using a common scanner. In other embodiments, the laser beam 201 and the OCT beam 301 beams may be scanned using separate scanners and then colinearly combined. In either case, a combined laser/OCT beam 550 is colinearly combined with an illumination beam 401 of the visual observation apparatus 400 with dichroic, polarization or other kind of beam combiners 600. The beam combiner 600 uses dichroic or polarization beam splitters to split and recombine light with different wavelength and/or polarization. The beam combiner 600 may also include optics to change certain parameters of the individual beams 201, 301, 401 such as beam size, beam angle and divergence. The combined laser/OCT/visual beam 701 is passed through optics of the focusing objective head 700 and optics of the patient interface 800 to reach a common target volume or surgical volume in the eye 1.

To resolve ocular tissue structures of the eye in sufficient detail, the imaging components 300, 400 of the integrated surgical system 1000 may provide an OCT beam and a visual observation beam having a spatial resolution of several micrometers. The resolution of the OCT beam is the spatial dimension of the smallest feature that can be recognized in the OCT image. It is determined mostly by the wavelength and the spectral bandwidth of the OCT source, the quality of the optics delivering the OCT beam to the target location in the eye, the numerical aperture of the OCT beam and the spatial resolution of the OCT imaging apparatus at the target location. In one embodiment, the OCT beam of the integrated surgical system has a resolution of no more than 5 µm.

Likewise, the surgical laser beam provided by the femtosecond laser source 200 may be delivered to targeted locations with several micrometer accuracy. The resolution of the laser beam is the spatial dimension of the smallest feature at the target location that can be modified by the laser beam without significantly affecting surrounding ocular tissue. It is determined mostly by the wavelength of the laser beam, the quality of the optics delivering the laser beam to target location in the eye, the numerical aperture of the laser beam, the energy of the laser pulses in the laser beam and the spatial resolution of the laser scanning system at the target location. In addition, to minimize the threshold energy of the laser for photo-disruptive interaction, the size of the laser spot should be no more than approximately 5 µm.

It should be noted that, while the observation beam 401 is acquired by the visual observation apparatus 400 using fixed, non-scanning optics, the OCT beam 301 of the OCT imaging apparatus 300 is scanned laterally in two transversal directions. The laser beam 201 of the femtosecond laser source 200 is scanned in two lateral dimensions and the depth of the focus is scanned axially.

For practical embodiments, beam conditioning, scanning and combining the optical paths are certain functions performed on the laser, OCT and visual observation optical beams. Implementation of those functions may happen in a different order than what is indicated in FIG. 7. Specific optical hardware that manipulates the beams to implement those functions can have multiple arrangements with regards to how the optical hardware is arranged. They can be arranged in a way that they manipulate individual optical beams separately, in another embodiment one component may combine functions and manipulates different beams. For example, a single set of scanners can scan both the laser beam 201 and the OCT beam 301. In this case, separate beam conditioners set the beam parameters for the laser beam 201 and the OCT beam 301, then a beam combiner combines the two beams for a single set of scanners to scan the beams. While many combinations of optical hardware arrangements are possible for the integrated surgical system, the following section describes in detail an example arrangement.

Figure 8:
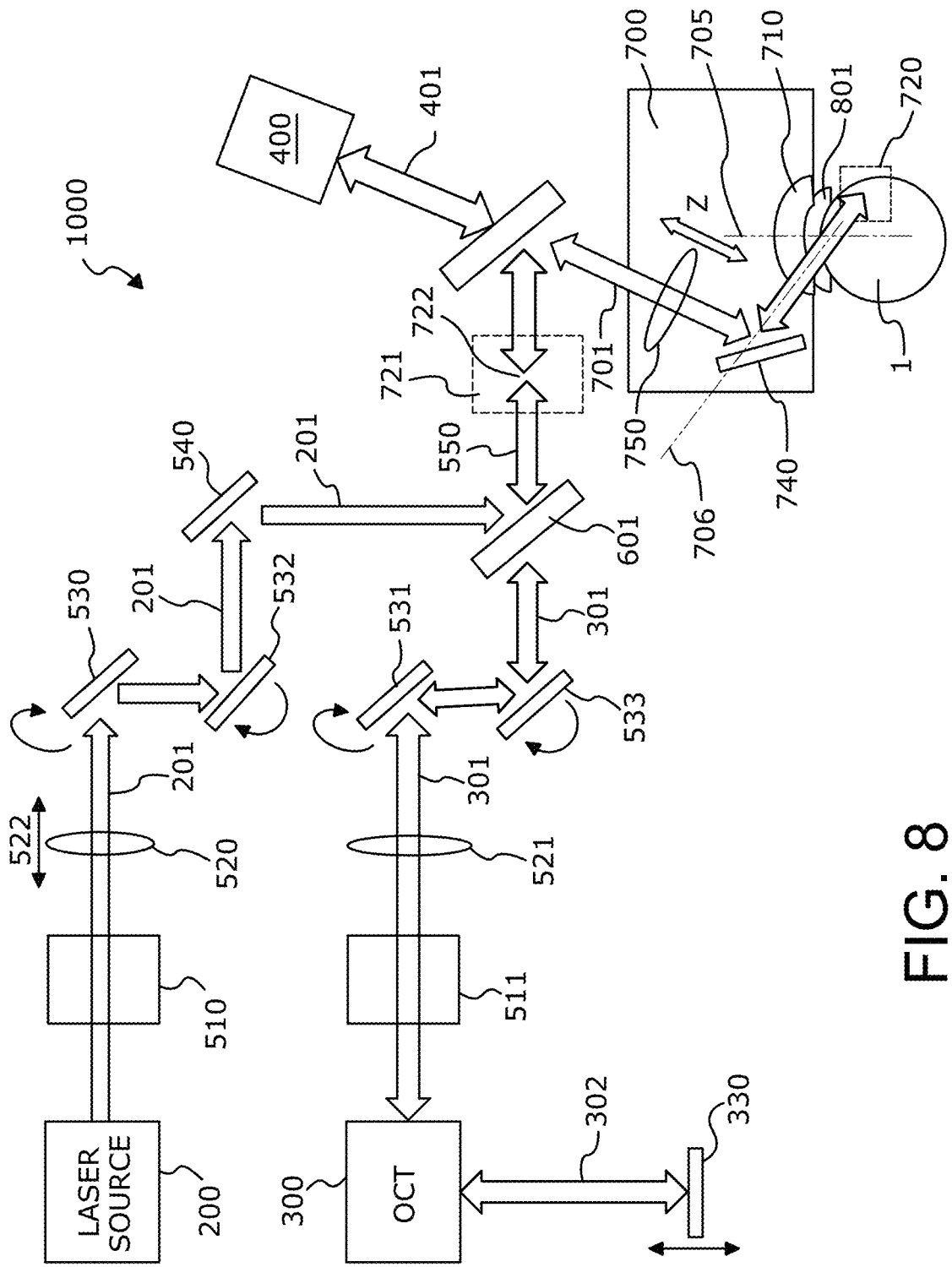
FIG. 8 is a detailed block diagram of the integrated surgical system of FIG. 7.

Referring to FIG. 8, an example integrated surgical system 1000 includes optical subsystems configured together to deliver each of a laser beam 201, an OCT beam 301, and an illumination beam 401 in the distal direction toward an eye 1, and receive each of an OCT return beam and an observation beam 401 back from the eye 1.

Regarding the delivery of a laser beam, a laser beam 201 output by the femtosecond laser source 200 passes through a beam conditioner 510 where the basic beam parameters, beam size, divergence are set. The beam conditioner 510 may also include additional functions, setting the beam power or pulse energy and shutter the beam to turn it on or off. After existing the beam conditioner 510, the laser beam 210 enters an axial scanning lens 520. The axial scanning lens 520, which may include a single lens or a group of lenses, is movable in the axial direction 522 by a servo motor, stepper motor or other control mechanism. Movement of the axial scanning lens 520 in the axial direction 522 changes the axial distance of the focus of the laser beam 210 at a focal point.

In accordance with a particular embodiment of the integrated surgical system, an intermediate focal point 722 is set to fall within, and is scannable in, the conjugate surgical volume 721, which is an image conjugate of the surgical volume 720, determined by optics of the focusing objective head 700. The surgical volume 720 is the spatial extent of the region of interest within the eye where imaging and surgery is performed. For glaucoma surgery, the surgical volume 720 is the vicinity of the irido-corneal angle 13 of the eye.

A pair of transverse scanning mirrors 530, 532 rotated by a galvanometer scanner scan the laser beam 201 in two essentially orthogonal transversal directions, e.g., in the x and y directions. Then the laser beam 201 is directed towards a dichroic or polarization beam splitter 540 where it is reflected toward a beam combining mirror 601 configured to combine the laser beam 201 with an OCT beam 301.

Regarding delivery of an OCT beam, an OCT beam 301 output by the OCT imaging apparatus 300 passes through a beam conditioner 511, an axially moveable focusing lens 521 and a transversal scanner with scanning mirrors 531 and 533. The focusing lens 521 is used set the focal position of the OCT beam in the conjugate surgical volume 721 and the real surgical volume 720. The focusing lens 521 is not scanned for obtaining an OCT axial scan. Axial spatial information of the OCT image is obtained by Fourier transforming the spectrum of the interferometrically recombined OCT return beam 301 and reference beams 302. However, the focusing lens 521 can be used to re-adjust the focus when the surgical volume 720 is divided into several axial segments. This way the optimal imaging spatial resolution of the OCT image can be extended beyond the Rayleigh range of the OCT signal beam, at the expense of time spent on scanning at multiple ranges.

Proceeding in the distal direction toward the eye 1, after the scanning mirrors 531 and 533, the OCT beam 301 is combined with the laser beam 201 by the beam combiner mirror 601. The OCT beam 301 and laser beam 201 components of the combined laser/OCT beam 550 are multiplexed and travel in the same direction to be focused at an intermediate focal point 722 within the conjugate surgical volume 721. After having been focused in the conjugate surgical volume 721, the combined laser/OCT beam 550 propagates to a second beam combining mirror 602 where it is combined with a visual observation beam 401 to form a combined laser/OCT/visual beam 701.

The combined laser/OCT/visual beam 701 traveling in the distal direction then passes through a relay lens 750 included in the focusing objective head 700, is reflected by a reflecting surface 740, which may be a planar beam-folding mirror or a facet inside an optic, and then passes through an exit lens 710 of the focusing objective head and a window 801 of a patient interface, where the intermediate focal point 722 of the laser beam within the conjugate surgical volume 721 is re-imaged into a focal point in the surgical volume 720. The optics of the focusing objective head 700 re-images the intermediate focal point 722, through the window 801 of a patient interface, into the ocular tissue within the surgical volume 720. In one configuration, the reflecting surface 740 in the form of a facet inside an optic may have a specialized coating for broadband reflection (visible, OCT and femtosecond) and low difference between s and p polarization group delay dispersion (GDD).

A scattered OCT return beam 301 from the ocular tissue travels in the proximal direction to return to the OCT imaging apparatus 300 along the same paths just described, in reverse order. The reference beam 302 of the OCT imaging apparatus 300, passes through a reference delay optical path and return to the OCT imaging apparatus from a moveable mirror 330. The reference beam 302 is combined interferometrically with the OCT return beam 301 on its return within the OCT imaging apparatus 300. The amount of delay in the reference delay optical path is adjustable by moving the moveable mirror 330 to equalize the optical paths of the OCT return beam 301 and the reference beam 302. For best axial OCT resolution, the OCT return beam 301 and the reference beam 302 are also dispersion compensated to equalize the group velocity dispersion within the two arms of the OCT interferometer.

When the combined laser/OCT/visual beam 701 is delivered through the cornea 3 and the anterior chamber 7, the combined beam passes through posterior and anterior surface of the cornea at a steep angle, far from normal incidence. These surfaces in the path of the combined laser/OCT/visual beam 701 create excessive astigmatism and coma aberrations that need to be compensated for.

Figure 9B:
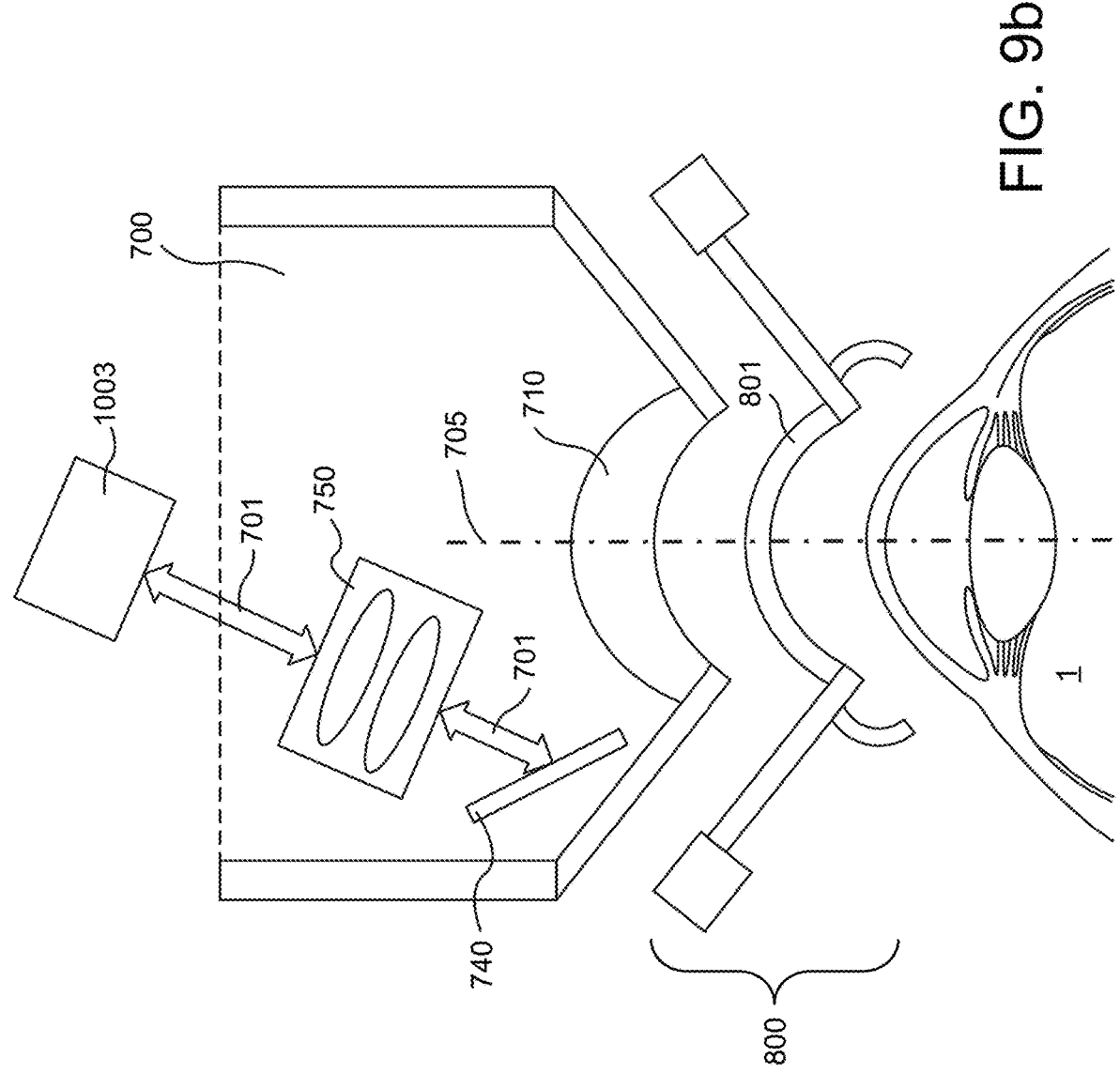

With reference to FIGS. 9a and 9b, in an embodiment of the integrated surgical system 1000, optical components of the focusing objective head 700 and patient interface 800 are configured to minimize spatial and chromatic aberrations and spatial and chromatic distortions. FIG. 9a shows a configuration when both the eye 1, the patient interface 800 and the focusing objective head 700 all coupled together. FIG. 9b shows a configuration when both the eye 1, the patient interface 800 and the focusing objective head 700 all detached from one another.

The patient interface 800 optically and physically couples the eye 1 to the focusing objective head 700, which in turn optically couples with other optic components of the integrated surgical system 1000. The patient interface 800 serves multiple functions. It immobilizes the eye relative to components of the integrated surgical system; creates a sterile barrier between the components and the patient; and provides optical access between the eye and the instrument. The patient interface 800 is a sterile, single use disposable device and it is coupled detachably to the eye 1 and to the focusing objective head 700 of the integrated surgical system 1000.

Figure 9C:
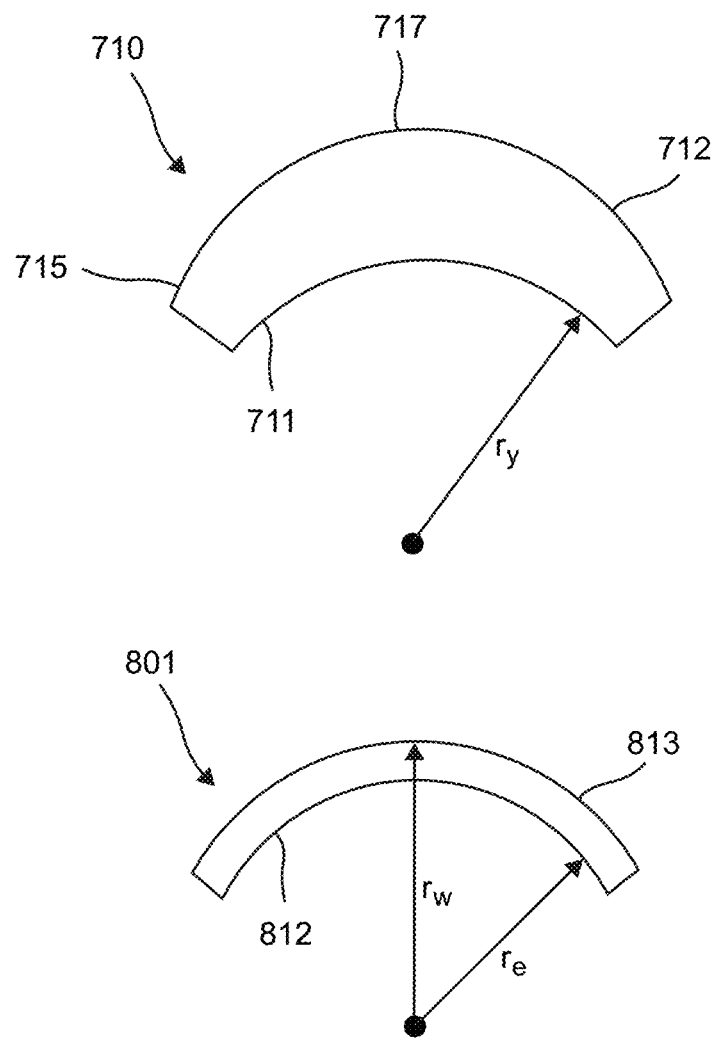
FIG. 9c is a schematic illustration of components of the focusing objective head and the patient interface included in FIGS. 9a and 9b.

The patient interface 800 includes a window 801 having an eye-facing, concave surface 812 and an objective-facing, convex surface 813 opposite the concave surface. The window 801 thus has a meniscus form. With reference to FIG. 9c, the concave surface 812 is characterized by a radius of curvature $r_e$, while the convex surface 813 is characterized by a radius of curvature $r_w$. The concave surface 812 is configured to couple to the eye, either through a direct contact or through index matching material, liquid or gel, placed in between the concave surface 812 and the eye 1. The window 801 may be formed of glass and has a refractive index $n_w$. In one embodiment, the window 801 is formed of fused silica and has a refractive index $n_w$ of 1.45. Fused silica has the lowest index from common inexpensive glasses. Fluoropolymers such as the Teflon AF are another class of low index materials that have refractive indices lower than fused silica, but their optical quality is inferior to glasses and they are relatively expensive for high volume production. In another embodiment the window 801 is formed of the common glass BK7 and has a refractive index $n_w$ of 1.50. A radiation resistant version of this glass, BK7G18 from Schott AG, Mainz, Germany, allows gamma sterilization of the patient interface 800 without the gamma radiation altering the optical properties of the window 801.

Returning to FIGS. 9a and 9b, the window 801 is surrounded by a wall 803 of the patient interface 800 and an immobilization device, such as a suction ring 804. When the suction ring 804 is in contact with the eye 1, an annular cavity 805 is formed between the suction ring and the eye. When vacuum applied to the suction ring 804 and the cavity via a vacuum tube a vacuum pump (not shown in FIGS. 9a and 9b), vacuum forces between the eye and the suction ring attach the eye to the patient interface 800 during surgery. Removing the vacuum releases or detach the eye 1.

The end of the patient interface 800 opposite the eye 1 includes an attachment interface 806 configured to attach to the housing 702 of the focusing objective head 700 to thereby affix the position of the eye relative to the other components of the integrated surgical system 1000. The attachment interface 806 can work with mechanical, vacuum, magnetic or other principles and it is also detachable from the integrated surgical system.

The focusing objective head 700 includes an aspheric exit lens 710 having an eye-facing, concave surface 711 and a convex surface 712 opposite the concave surface. The exit lens 710 thus has a meniscus form. While the exit lens 710 shown in FIGS. 9a and 9b is an aspheric lens giving more design freedom, in other configurations the exit lens may be a spherical lens. Alternatively, constructing the exit lens 710 as a compound lens, as opposed to a singlet, allows more design freedom to optimize the optics while preserving the main characteristics of the optical system as presented here. With reference to FIG. 9c, the concave surface 711 is characterized by a radius of curvature $r_x$, while the convex surface 712 is characterized by an aspheric shape. The aspheric convex surface 712 in combination with the spherical concave surface 711 result in an exit lens 710 having varying thickness, with the outer perimeter edges 715 of the lens being thinner than the central, apex region 717 of the lens. The concave surface 711 is configured to couple to the convex surface 813 of the window 801. In one embodiment, the exit lens 710 is formed of fused silica and has a refractive index $n_x$ of 1.45.

Figure 10A:
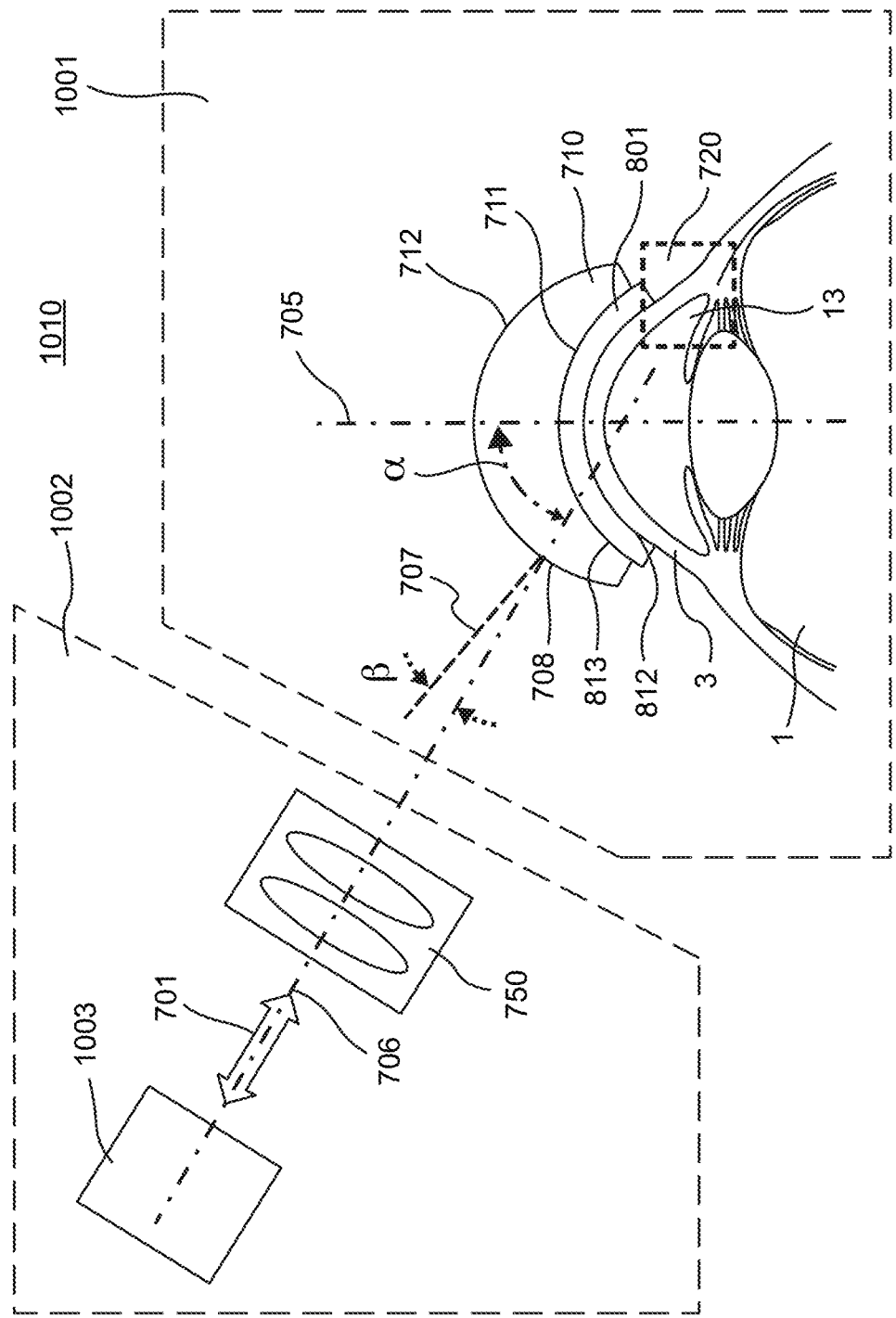
FIGS. 10a and 10b are schematic illustrations of components of the integrated surgical system of FIGS. 7 and 8 functionally arranged to form a first optical system and a second optical subsystem that enable access to the irido-corneal angle along the angled beam path of FIG. 6.
Figure 10B:
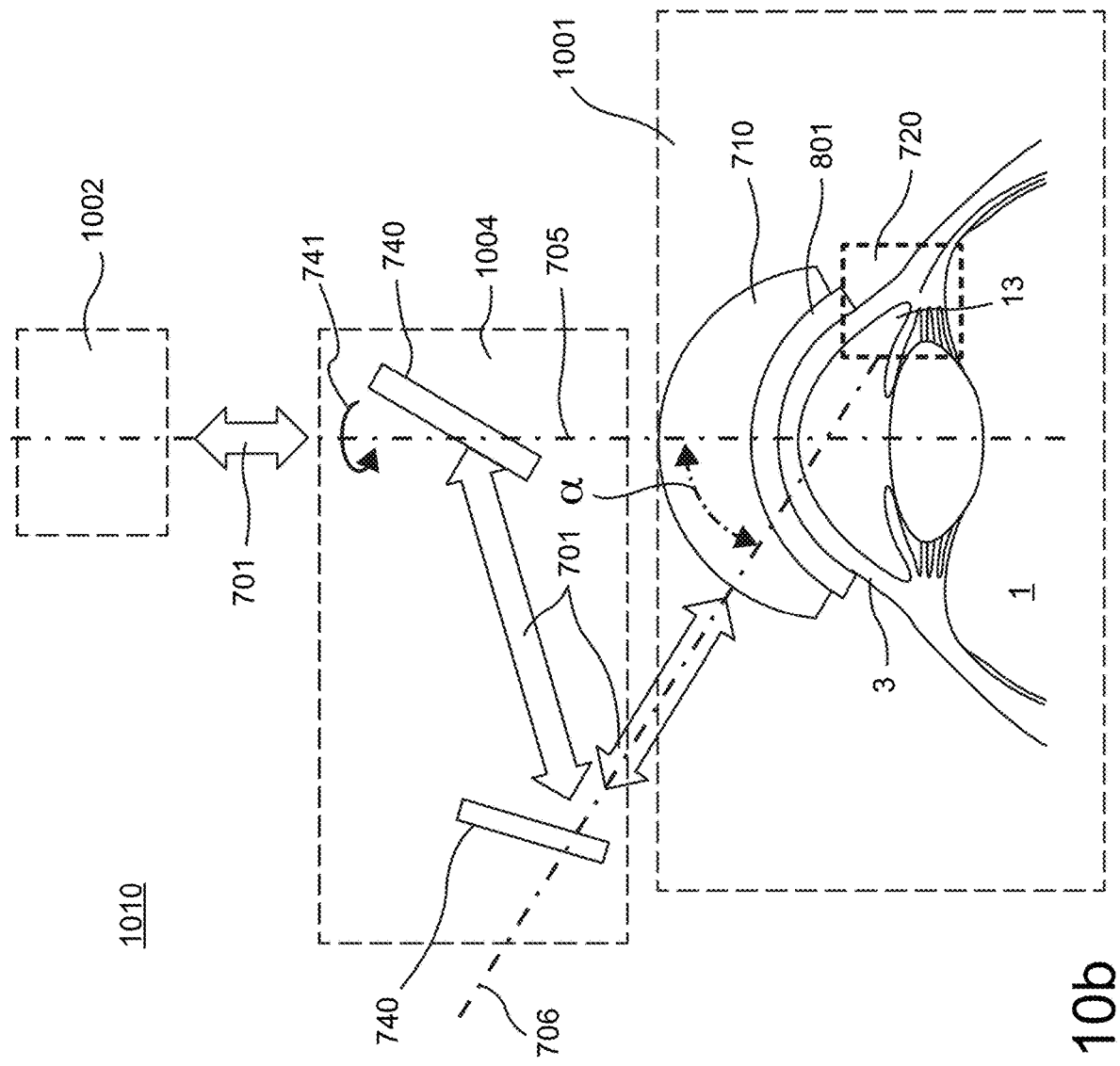
Figure 10C:
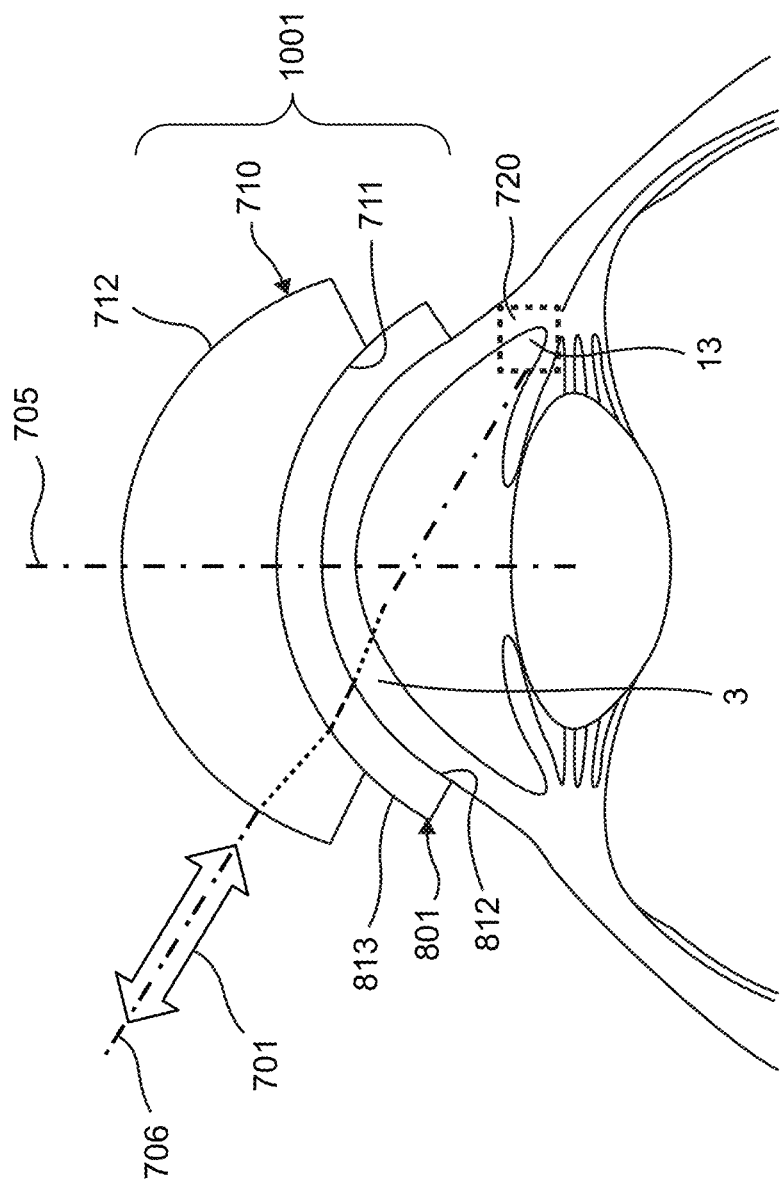
FIG. 10c is a schematic illustration of a beam passing through the first optical subsystem of FIGS. 10a and 10b and into the eye.

FIGS. 10a and 10b are schematic illustrations of components of the integrated surgical system of FIGS. 7 and 8 functionally arranged to form an optical system 1010 having a first optical subsystem 1001 and a second optical subsystem 1002 that enable access to a surgical volume 720 in the irido-corneal angle. Each of FIGS. 10a and 10b include components of the focusing objective head 700 and the patient interface 800 of FIG. 9a. However, for simplicity, the entirety of the focusing objective head and the patient interface are not included in FIGS. 10a and 10b. Also, for additional simplicity in FIG. 10a, the reflecting surface 740 of FIGS. 9a and 9b is not included and the combined laser/OCT/visual beam 701 shown in FIG. 9a is unfolded or straightened out. It is understood by those skilled in the art that adding or removing planar beam folding mirrors does not alter the principal working of the optical system formed by the first optical subsystem and the second optical subsystem. FIG. 10c is a schematic illustration of a beam passing through the first optical subsystem of FIGS. 10a and 10b.

With reference to FIG. 10a, a first optical subsystem 1001 of the integrated surgical system 1000 includes the exit lens 710 of a focusing objective head 700 and the window 801 of a patient interface 800. The exit lens 710 and the window

801 are arranged relative to each other to define a first optical axis 705. The first optical subsystem 1001 is configured to receive a beam, e.g., a combined laser/OCT/visual beam 701, incident at the convex surface 712 of the exit lens 710 along a second optical axis 706, and to direct the beam toward a surgical volume 720 in the irido-corneal angle 13 of the eye.

During a surgical procedure, the first optical subsystem 1001 may be assembled by interfacing the convex surface 813 of the window 801 with the concave surface 711 of the exit lens 710. To this end, a focusing objective head 700 is docked together with a patient interface 800. As a result, the concave surface 711 of the exit lens 710 is coupled to the convex surface 813 of the window 801. The coupling may be by direct contact or through a layer of index matching fluid. For example, when docking the patient interface 800 to focusing objective head 700, a drop of index matching fluid can be applied between the contacting surfaces to eliminate any air gap that may be between the two surfaces 711, 813 to thereby help pass the combined laser/OCT/visual beam 701 through the gap with minimal Fresnel reflection and distortion.

In order to direct the beam toward the surgical volume 720 in the irido-corneal angle 13 of the eye, the first optical subsystem 1001 is designed to account for refraction of the beam 701 as it passes through the exit lens 710, the window 801 and the cornea 3. To this end, and with reference to FIG. 10c, the refractive index $n_x$ of the exit lens 710 and the refractive index $n_w$ of the window 801 are selected in view of the refractive index $n_c$ of the cornea 3 to cause appropriate beam bending through the first optical subsystem 1001 so that when the beam 701 exits the subsystem and passes through the cornea 3, the beam path is generally aligned to fall within the irido-corneal angle 13.

Continuing with reference to FIG. 10c and beginning with the interface between the window 801 and the cornea 3. Too steep of an angle of incidence at the interface where the combined laser/OCT/visual beam 701 exits the window 801 and enters the cornea 3, i.e., at the interface between the concave surface 812 of the window and the convex surface of the cornea 3, can create excessive refraction and distortion. To minimize refraction and distortion at this interface, in one embodiment of the first optical subsystem 1001, the refractive index of the window 801 is closely matched to the index of the cornea 3. For example, as describe above with reference to FIGS. 9a and 9b, the window 801 may have a refractive index lower than 1.42 to closely match the cornea 3, which has a refractive index of 1.36.

Excessive refraction and distortion at the interface where the combined laser/OCT/visual beam 701 exits the window 801 and enters the cornea 3 may be further compensated for by controlling the bending of the beam 701 as it passed through the exit lens 710 and the window 801. To this end, in one embodiment of the first optical subsystem 1001 the index of refraction $n_w$ of the window 801 is larger than each of the index of refraction $n_x$ of the exit lens 710 and the index of refraction $n_c$ of the cornea 3. As a result, at the interface where the combined laser/OCT/visual beam 701 exits the exit lens 710 and enters the window 801, i.e., interface between the concave surface 711 of the exit lens and the convex surface 813 of the window, the beam passes through a refractive index change from high to low that cause the beam to bend in a first direction. Then, at the interface where the combined laser/OCT/visual beam 701 exits the window 801 and enters the cornea 3, i.e., interface between the concave surface 812 of the exit lens and the convex surface of the cornea, the beam passes through a refractive index change from low to high that cause the beam to bend in a second direction opposite the first direction.

The shape of the window 801 is chosen to be a meniscus lens. As such, the incidence angle of light has similar values on both surfaces 812, 813 of the window 801. The overall effect is that at the convex surface 813 the light bends away from the surface normal and at the concave surface 812 the light bends towards the surface normal. The effect is like when light passes through a plan parallel plate. Refraction on one surface of the plate is compensated by refraction on the other surface a light passing through the plate does not change its direction. Refraction at the entering, convex surface 712 of the exit lens 710 distal to the eye is minimized by setting the curvature of the entering surface such that angle of incidence β of light 701 at the entering surface is close to a surface normal 707 to the entering surface at the intersection point 708.

Here, the exit lens 710, the window 801, and the eye 1 are arranged as an axially symmetric system with a first optical axis 705. In practice, axial symmetry is an approximation because of manufacturing and alignment inaccuracies of the optical components, the natural deviation from symmetry of the eye and the inaccuracy of the alignment of the eye relative to the window 801 and the exit lens 710 in a clinical setting. But, for design and practical purposes the eye 1, the window 801, and the exit lens 710 are considered as an axially symmetric first optical subsystem 1001.

With continued reference to FIG. 10a, a second optical subsystem 1002 is optically coupled to the first optical subsystem 1001 at an angle α relative to the first optical axis 705 of the first optical subsystem 1001. The advantage of this arrangement is that both optical subsystems 1001, 1002 can be designed at a much lower numerical aperture compared to a system where all optical components are designed on axis with a common optical axis.

The second optical subsystem 1002 includes a relay lens 750 that, as previously described with reference to FIG. 8, generates a conjugate surgical volume 721 of the surgical volume 720 within the eye. The second optical subsystem 1002 includes various other components collectively indicated as an optical subsystem step 1003. Referring to FIG. 8, these components may include a femtosecond laser source 200, an OCT imaging apparatus 300, a visual observation apparatus 400, beam conditioners and scanners 500, and beam combiners 600.

The second optical subsystem 1002 may include mechanical parts (not shown) configured to rotate the entire subsystem around the first optical axis 705 of the first optical subsystem 1001. This allows optical access to the whole 360-degree circumference of the irido-corneal angle 13 of the eye 1.

With reference to FIG. 10b, flexibility in arranging the first and second optical subsystems 1001, 1002, relative to each other may be provided by an optical assembly 1004 interposed between the optical output of the second optical subsystem 1002 and the optical input of the first optical subsystem 1001. In one embodiment, the optical assembly 1004 may include one or more reflecting surfaces 740, prisms (not shown) or optical gratings (not shown) configured to receive the optical output, e.g., combined laser/OCT/visual beam 701, of the second optical subsystem 1002, change or adjust the direction of the combined laser/OCT/visual beam, and direct the beam to the optical input of the first optical subsystem 1001 while preserving the angle α between the first optical axis 705 and the second optical axis 706.

In another configuration, the optical assembly 1004 of the reflecting surfaces 740 further includes mechanical parts (not shown) configured to rotate 741 the assembly around the first optical axis 705 of the first optical subsystem 1001 while keeping the second optical subsystem 1002 stationary. Accordingly, the second optical axis 706 of the second optical subsystem 1002 can be rotated around the first optical axis 705 of the first optical subsystem 1001. This allows optical access to the whole 360-degree circumference of the irido-corneal angle 13 of the eye 1.

With considerations described above with reference to FIGS. 9a, 9b and 9c, the design of the first optical subsystem 1001 is optimized for angled optical access at an angle α relative to the first optical axis 705 of the first optical subsystem 1001. Optical access at the angle α compensates for optical aberrations of the first optical subsystem 1001. Table 1 shows the result of the optimization at access angle α=72 degrees with Zemax optical design software package. This design is a practical embodiment for image guided femtosecond glaucoma surgery.

TABLE 1

| Surface | Structure and Material | Refractive index | Radius [mm] | Center Thickness [mm] |
|---|---|---|---|---|
| concave surface 711, convex surface 712 | Exit lens 710 of focusing objective head 700. Fused silica | 1.45 | −10 | 4.5 |
| concave surface 812, convex surface 813 | Window 801 of patient interface. BK7G18 | 1.50 | −10.9 | 1.0 |
| 3 | Cornea | 1.36 | −7.83 | 0.54 |
| 8 | Aqueous humor | 1.32 | −6.53 | 3.5 |
| Target | Ophthalmic tissue | 1.38 | N/A | 0 to 1 mm |

This design produces diffraction limited focusing of 1030 nm wavelength laser beams and 850 nm wavelength OCT beams with numerical aperture (NA) up to 0.2. In one design, the optical aberrations of the first optical subsystem are compensated to a degree that the Strehl ratio of the first optical subsystem for a beam with numerical aperture larger than 0.15 at the irido-corneal angle is larger than 0.9. In another design, the optical aberrations of the first optical subsystem are partially compensated, the remaining uncompensated aberrations of the first optical system are compensated by the second optical subsystem to a degree that the Strehl ratio of the combined first and second optical subsystem for a beam with numerical aperture larger than 0.15 at the irido-corneal angle is larger than 0.9.

Calibration

The femtosecond laser source 200, OCT imaging apparatus 300, and visual observation apparatus 400 of the integrated surgical system 1000 are first individually calibrated to ensure their internal integrity and then cross-calibrated for system integrity. The essential part of system calibration is to ensure that the when the surgical focus of a laser beam 201 is commanded to a location of a surgical volume 720, as identified by the OCT imaging apparatus and/or the visual observation apparatus 400, the achieved location of the focus matches the commanded location of the focus within a certain tolerance, typically within 5 to 10 µm. Also, graphical and cursor outputs, images, overlays displayed on a user interface 110, such as a computer monitor, and user inputs of ocular tissue surgical volume 720 locations accepted from the user interface 110 should correspond to actual locations in tissue within predetermined tolerances of similar accuracy.

One embodiment of this spatial calibration procedure starts with imaging calibrated scales and scaling magnifications of the OCT imaging apparatus 300 and/or the visual observation apparatus 400 and their displays in a way that the scale value on the display matches the real scale of the calibration target. Then laser calibration patterns are exposed or burned into transparent calibration targets, and the calibration patterns are subsequently imaged. Then, the intended patterns and the actual burned patterns are compared with the imaging system of the integrated surgical system 1000 or by a separate microscope. If they do not match within the specified tolerance, the scaling parameters of the surgical patterns are re-scaled by adjusting the scaling of the laser beam scanners. This procedure is iterated, if necessary, until all spatial calibrations are within tolerance.

Minimally Invasive Surgical Treatments

Figure 11:
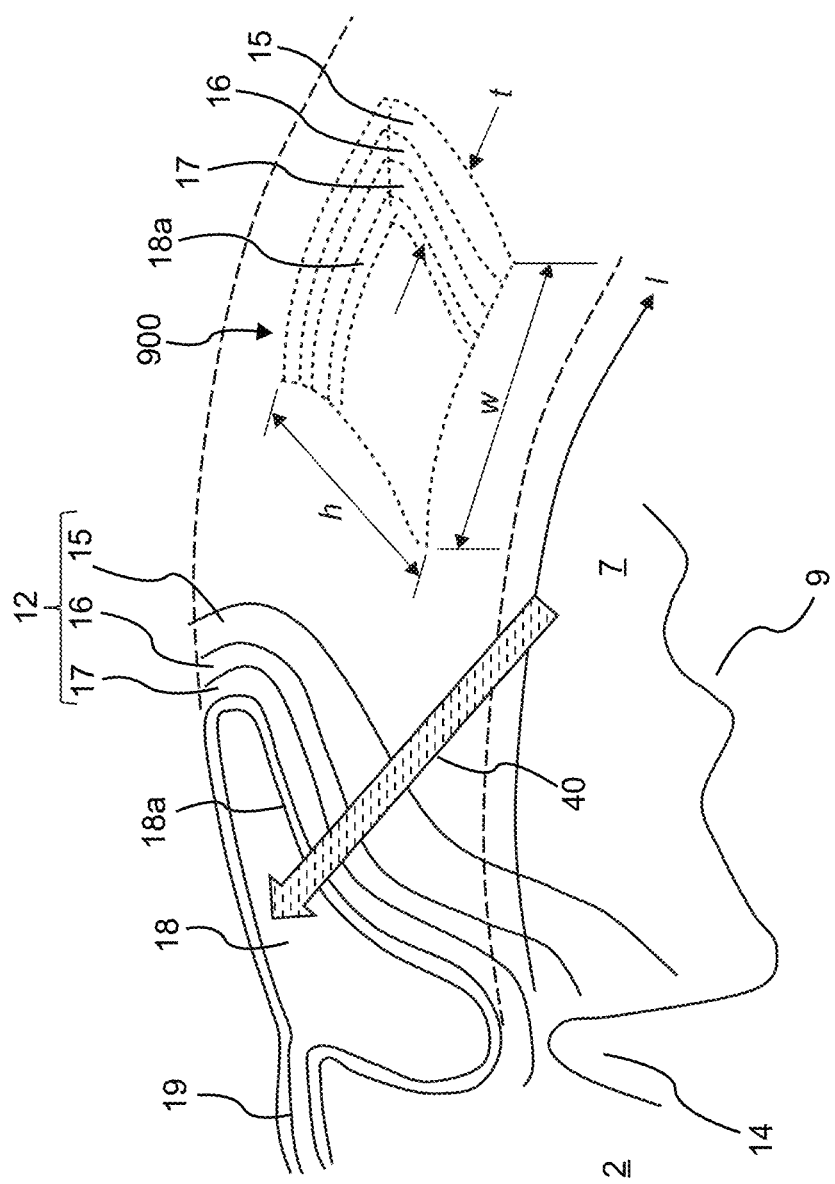
FIG. 11 is a three-dimensional schematic illustration of anatomical structures in the irido-corneal angle, including the trabecular meshwork, Schlemm's canal, a collector channel branching from the Schlemm's canal, and a surgical volume of ocular tissue to be treated by the integrated surgical system of FIG. 7.

FIG. 11 is a three-dimensional schematic illustration of anatomical structures of the eye relevant to the surgical treatment enabled by the integrated surgical system 1000. To reduce the IOP, laser treatment targets ocular tissues that affect the trabecular outflow pathway 40. These ocular tissues may include the trabecular meshwork 12, the scleral spur 14, the Schlemm's canal 18, and the collector channels 19. The trabecular meshwork 12 has three layers, the uveal 15, the corneoscleral meshwork 16, and the juxtacanalicular tissue 17. These layers are porous and permeable to aqueous, with the uveal 15 being the most porous and permeable, followed by the corneoscleral meshwork 16. The least porous and least permeable layer of the trabecular meshwork 12 is the juxtacanalicular tissue 17. The inner wall 18a of the Schlemm's canal 18, which is also porous and permeable to aqueous, has characteristics similar to the juxtacanalicular tissue 17.

Figure 12A:
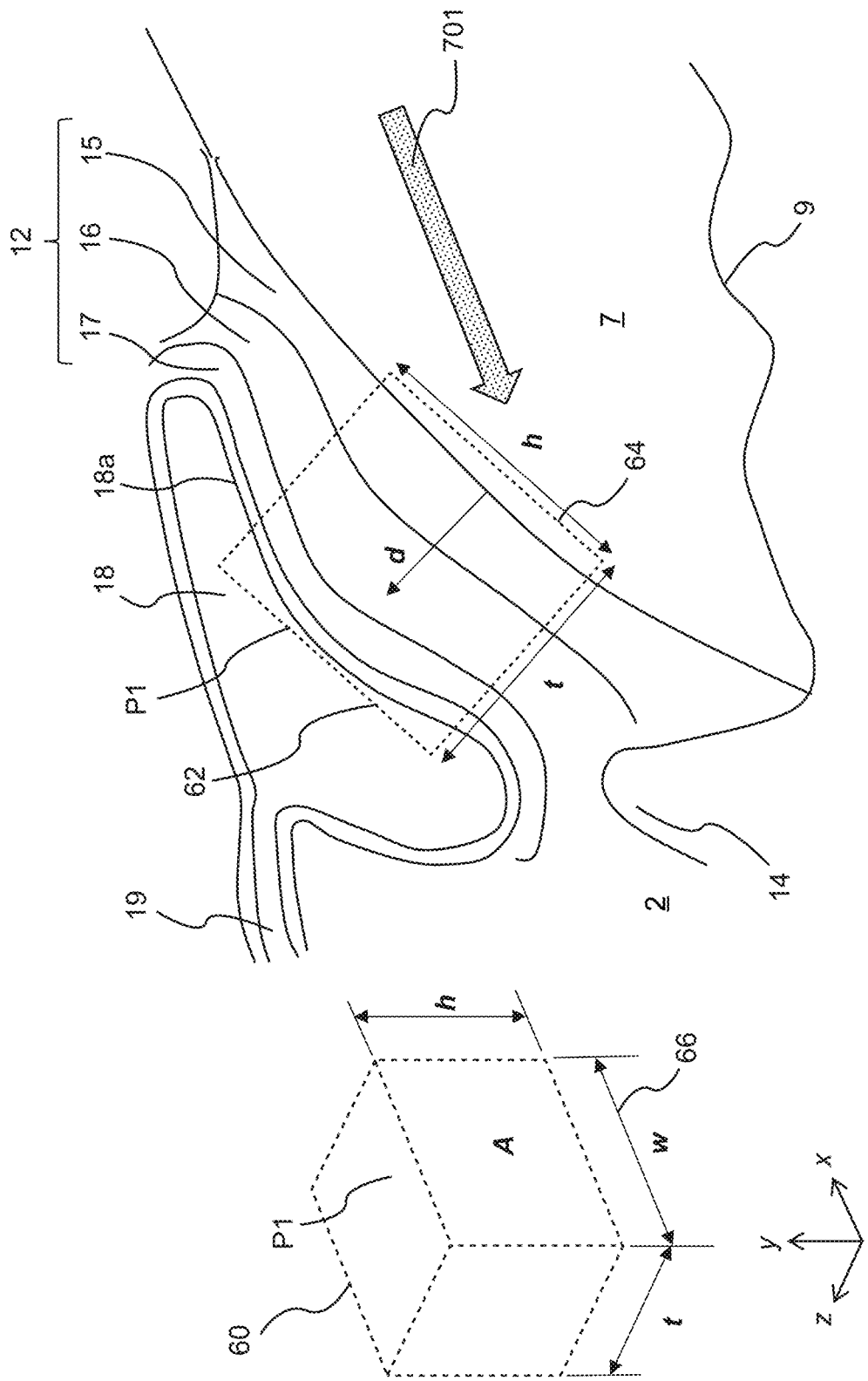
FIGS. 12a and 12b are two-dimensional schematic illustrations of anatomical structures in the irido-corneal angle and a three-dimensional laser treatment pattern to be applied by the integrated surgical system of FIG. 7 to affect a surgical volume of ocular tissue between the Schlemm's canal and the anterior chamber as shown in FIG. 11.
Figure 12B:
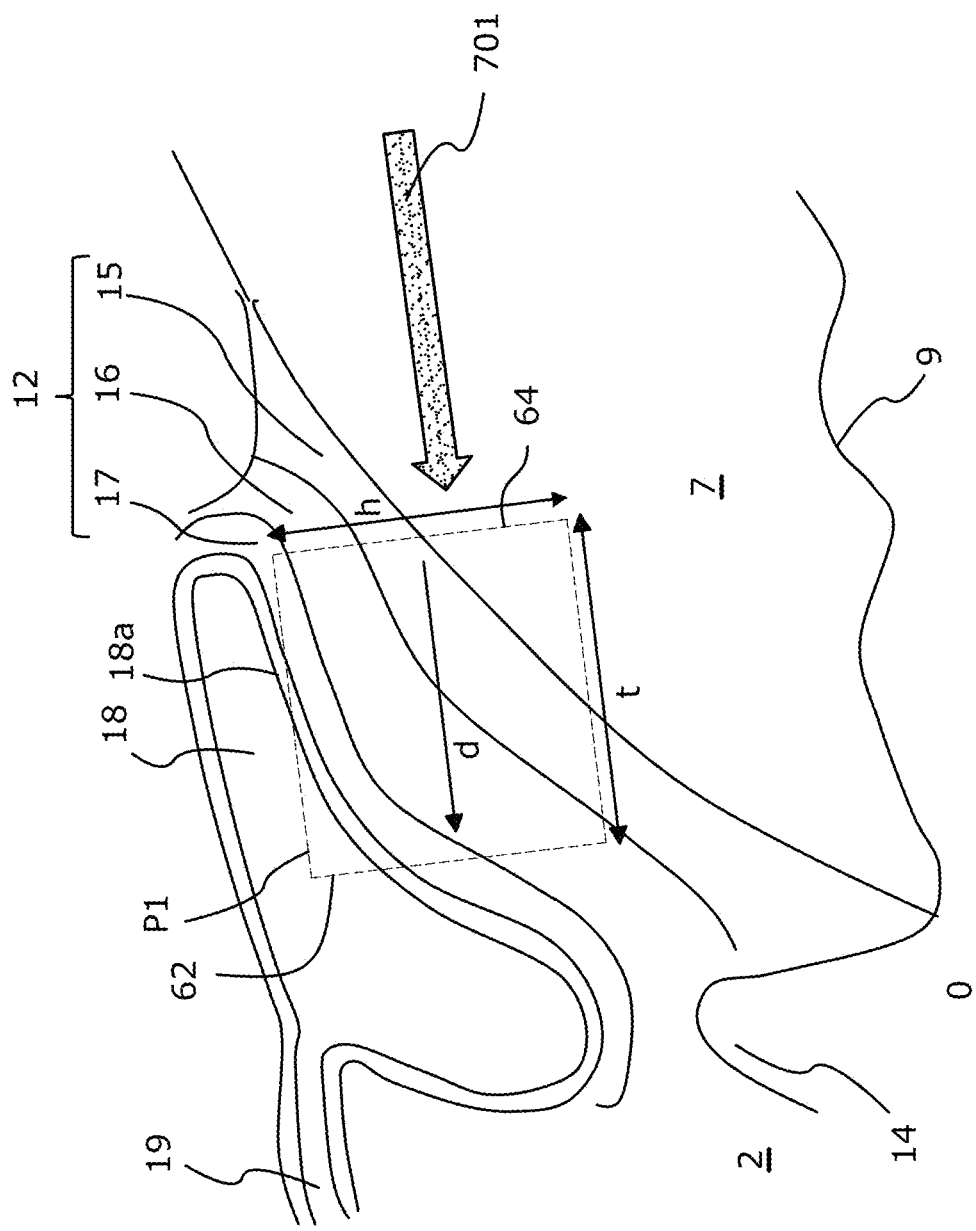
Figure 12B:
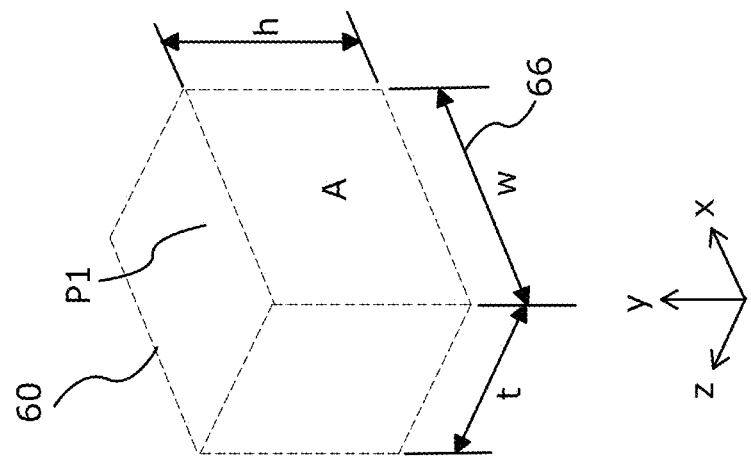
Figure 13:
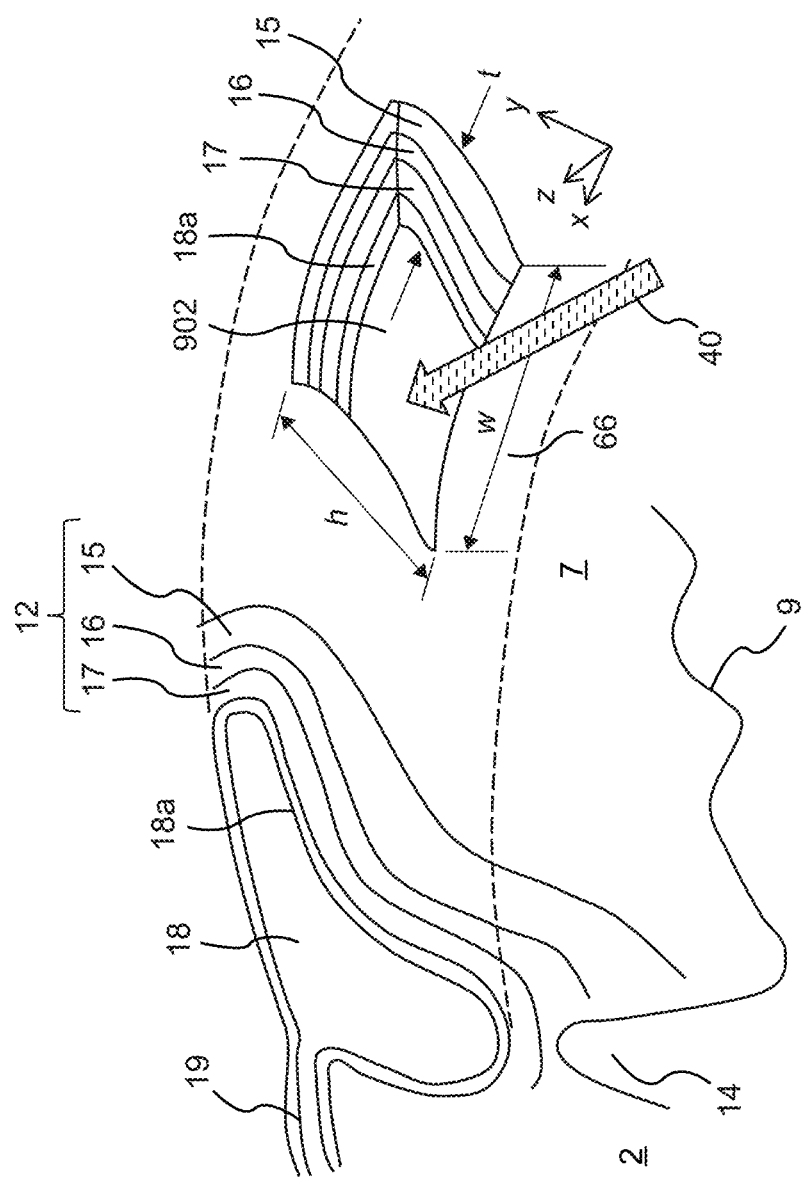
FIG. 13 is a three-dimensional schematic illustration of FIG. 11 subsequent to treatment of the surgical volume of ocular tissue by a laser based on the laser treatment pattern of FIGS. 12a and 12b that forms an opening between the Schlemm's canal and the anterior chamber.

FIGS. 12a and 12b include three-dimensional illustrations of a treatment pattern P1 to be applied by the integrated surgical system 1000 to affect the surgical volume 900 of ocular tissue shown in FIG. 11, and a two-dimensional schematic illustration of the treatment pattern P1 overlaying anatomical structures to be treated. FIG. 12b is essentially the same as FIG. 12a, but more clearly illustrates an orthogonal relationship between the treatment pattern P1 and the laser beam 701. FIG. 13 is a three-dimensional schematic illustration of the anatomical structures of the eye including an opening 902 through the trabecular meshwork 12 that results from the application of the laser treatment pattern of FIGS. 12a and 12b. The opening 902 may also be referred to as a channel or aperture. The opening 902 provides and outflow pathway 40 that reduces the flow resistance in the ocular tissue to increase aqueous flow from the anterior chamber 7 into the Schlemm's canal 18 and thereby reduce the IOP of the eye.

Surgical treatments reduce outflow pathway resistance while minimizing ocular tissue modification through design and selection of laser treatment patterns. A treatment pattern is considered to define a collection of a laser-tissue interaction volumes, referred to herein as cells. The size of a cell is determined by the extent of the influence of the laser-tissue interaction. When the laser spots, or cells, are spaced close along a line, the laser creates a narrow, microscopic channel. A wider channel can be created by closely spacing a multitude of laser spots within the cross section of the channel. The arrangement of the cells may resemble the arrangement of atoms in a crystal structure.

With reference to FIGS. 12a and 12b, a treatment pattern P1 may be in the form of a cubic structure that encompasses individual cells arranged in regularly spaced rows, columns and sheets or layers. The treatment pattern P1 may be characterized by x, y, z dimensions, with x, y, z coordinates of the cells being calculated sequentially from neighbor to neighbor in the order of a column location (x coordinate), a row location (y coordinate), and a layer location (z coordinate). A treatment pattern P1 as such, defines a three-dimensional model of ocular tissue to be modified by a laser or a three-dimensional model of ocular fluid to be affected by a laser.

A treatment pattern P1 is typically defined by a set of surgical parameters. The surgical parameters may include one or more of a treatment area A that represents a surface area or layer of ocular tissue through which the laser will travel. The treatment area A is determined by the treatment height, h, and the lateral extent of the treatment, w. A treatment thickness t that represents the level to which the laser will cut into the ocular tissue from the distal extent or border of the treatment volume at or near Schlemm's canal 18 to the proximal extent or border at or near the surface of the trabecular meshwork 12. Thus, a laser applied in accordance with a treatment pattern may affect or produce a surgical volume that resembles the three-dimensional model of the treatment pattern, or may affect fluid located in an interior of an eye structure resembled by the three-dimensional model.

Additional surgical parameters define the placement of the surgical volume or affected volume within the eye. For example, with reference to FIGS. 11, 12a, and 12b, placement parameters may include one or more of a location l that represents where the treatment is to occur relative to the circumferential angle of the eye, and a treatment depth d that represents a position of the three-dimensional model of ocular tissue or ocular fluid within the eye relative to a reference eye structure. In the following, the treatment depth d is shown and described relative to the region where the anterior chamber 7 meets the trabecular meshwork 12. Together, the treatment pattern and the placement parameters define a treatment plan.

A femtosecond laser provides highly localized, non-thermal photo-disruptive laser-tissue interaction with minimal collateral damage to surrounding ocular tissue. Photo-disruptive interaction of the laser is utilized in optically transparent tissue. The principal mechanism of laser energy deposition into the ocular tissue is not by absorption but by a highly nonlinear multiphoton process. This process is effective only at the focus of the pulsed laser where the peak intensity is high. Regions where the beam is traversed but not at the focus are not affected by the laser. Therefore, the interaction region with the ocular tissue is highly localized both transversally and axially along the laser beam.

With reference to FIGS. 11, 12a, and 12b, in accordance with embodiments disclosed herein a surgical volume 900 of ocular tissue to be treated is identified by the integrated surgical system 1000 and a treatment pattern P1 corresponding to the surgical volume is designed by the integrated surgical system. Alternatively, the treatment pattern P1 may be designed first, and then an appropriate surgical volume 900 for applying the treatment pattern may be identified. The surgical volume 900 of ocular tissue may comprise portions of the trabecular meshwork 12 and the Schlemm's canal 18. For example, the surgical volume 900 of ocular tissue shown in FIG. 11 includes portions of the uveal 15, the corneoscleral meshwork 16, the juxtacanalicular tissue 17, and the inner wall 18a of the Schlemm's canal 18. The treatment pattern P1 defines a laser scanning procedure whereby a laser is focused at different depth locations in ocular tissue and then scanned in multiple directions to affect a three-dimensional volume of tissue comprising multiple sheets or layers of affected tissue.

With reference to FIGS. 12a, 12b, and 13, during a laser scanning procedure, a surgical laser 701 may scan ocular tissue in accordance with the treatment pattern P1 to form an opening 902 that extends from the anterior chamber 7, through each of the uveal 15, the corneoscleral meshwork 16, the juxtacanalicular tissue 17 of the trabecular meshwork 12, and the inner wall 18a of the Schlemm's canal 18. While the example opening 902 in FIG. 13 is depicted as a continuous, single lumen defining a fluid pathway, the opening may be defined an arrangement of adjacent pores forming a sponge like structure defining a fluid pathway or a combination thereof. While the example opening 902 in FIG. 13 is in the shape of a cube, the opening may have other geometric shapes.

The movement of the laser as it scans to affect the surgical volume 900 follows the treatment pattern P1, which is defined by a set of surgical parameters that include a treatment area A and a thickness t. The treatment area A is defined by a width w and a height h. The width may be defined in terms of a measure around the circumferential angle. For example, the width w may be defined in terms of an angle, e.g., 90 degrees, around the circumferential angle.

Referring to FIGS. 11, 12a, and 12b, an initial placement of the laser focus within the eye is defined by a set of placement parameters, including a depth d and a location 1. The location 1 defines a point around the circumferential angle of the eye at which laser treatment will begin, while the depth d defines a point between the anterior chamber 7 and the Schlemm's canal 18 where the laser treatment begins or ends. The depth d is measured relative to the region where the anterior chamber 7 meets the trabecular meshwork 12. Thus, a first point that is closer to the Schlemm's canal 18 side of the trabecular meshwork 12 may be described as being deeper than a second point that is closer to the anterior chamber 7 side of the trabecular meshwork 12. Alternatively, the second point may be described as being shallower than the first point.

With reference to FIG. 13, the opening 902 resulting from laser application of the treatment pattern P1 resembles the surgical volume 900 and is characterized by an area A and thickness t similar to those of the surgical volume and the treatment pattern. The thickness t of the resulting opening 902 extends from the anterior chamber 7 and through the inner wall 18a of the Schlemm's canal 18, while the area A defines the cross-section size of the opening 902.

In accordance with embodiments disclosed herein, during a laser scanning procedure, a laser focus is moved to different depths d in ocular tissue and then scanned in two lateral dimensions or directions as defined by a treatment pattern P1 to affect a three-dimensional volume 900 of ocular tissue comprising multiple sheets or layers of affected tissue. The two lateral dimensions are generally orthogonal to the axis of movement of the laser focus. With reference to FIG. 13, the movement of a laser focus during laser scanning is described herein with reference to x, y, and z directions or axes, wherein: 1) movement of the laser focus to different depths d through the thickness t of treatment pattern P1 or the volume 900 of tissue corresponds to movement of the focus along the z axis, 2) movement of the laser focus in two dimensions or directions orthogonal to the z axis corresponds to movement of the laser focus along the width w of the treatment pattern P1 or the volume 900 of tissue in the x direction, and movement of the laser focus along the height h of the treatment pattern P1 or the volume 900 of tissue in the y direction.

As used herein scanning of the laser focus generally corresponds to a raster type movement of the laser focus in the x direction, the y direction, and the z direction. The laser focus may be located at a point in the z direction and then raster scanned in two dimensions or directions, in the x direction and the y direction. The focal point of the laser in the z direction may be referred to as a depth d within the treatment pattern P1 or the volume 900 of tissue. The two direction raster scanning of the laser focus defines a layer of laser scanning, which in turn produces a layer of laser-affected tissue.

During laser scanning, pulse shots of a laser are delivered to tissue within the volume of ocular tissue corresponding to the treatment pattern P1. Because the laser interaction volume is small, about a few micrometers (μm), the interaction of ocular tissue with each laser shot of a repetitive laser breaks down ocular tissue locally at the focus of the laser. Pulse duration of the laser for photo-disruptive interaction in ocular tissue can range from several femtoseconds to several nanoseconds and pulse energies from several nanojoules to tens of microjoules. The laser pulses at the focus, through multiphoton processes, breaks down chemical bonds in the molecules, locally photo-dissociate tissue material and create gas bubbles in wet tissue. The breakdown of tissue material and mechanical stress from bubble formation fragments the tissue and create clean continuous cuts when the laser pulses are laid down in proximity to one another along geometrical lines and surfaces.

Table 2 includes examples of treatment pattern parameters and surgical laser parameters for treating tissue. The range of the parameter set is limited by practical ranges for the repetition rate of the laser and the scanning speed of the scanners.

anterior chamber 7 and the Schlemm's canal 18 due to interference by gas bubbles produced during laser application. As noted above, femtosecond lasers generate a very short pulse of optical energy. When a beam of such pulses is focused to a very small volume of space characterized by a small cross-sectional area, a non-linear effect occurs within the focus spot. When such a focus spot is directed onto tissue, the tissue is photodisrupted (broken down) leaving a small bubble of gas. This process is essentially non-thermal and requires a tiny amount of energy. The result is that the surrounding tissue is not affected.

However, when a femtosecond laser beam is scanned over the surface of a tissue, the laser treatment of this initial surface layer generates a layer of bubbles over the area of the treatment. When the laser scans the layer of tissue below or deeper than the initial surface layer, these bubbles create a shadow effect that scatters the incident laser light, effectively blocking further treatment of the tissue. This renders further laser treatment of tissue beneath or deeper that the initial surface layer ineffective.

Figure 14A:
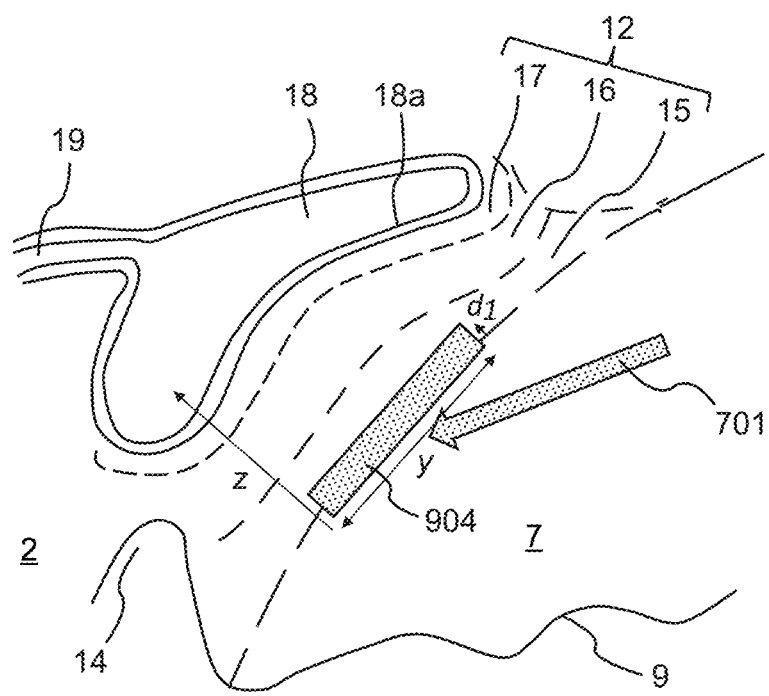
FIGS. 14a and 14b are a series of schematic illustrations of a laser scanning process based on the treatment pattern of FIGS. 12a and 12b, where the scanning begins adjacent the anterior chamber and proceeds toward the Schlemm's canal.
Figure 14B:
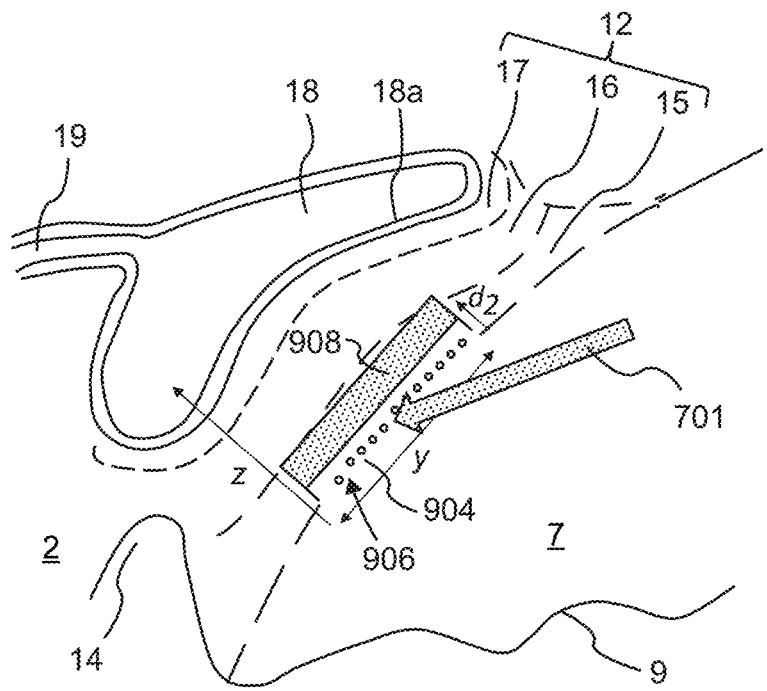

An example of this effect within the context of glaucoma surgery is illustrated in FIGS. 14a and 14b. In FIG. 14a, the focus of the laser beam 701 is initially located at a depth $d_1$. This depth $d_1$ places the laser focus in an initial layer 904 of tissue. For example, initial layer 904 of tissue may be at the interface between the uveal 15 of the trabecular meshwork 12 and the anterior chamber 7. In this instance, this depth location of the laser focus is referred to a null depth and the initial layer 904 to be treated corresponds to the surface of the uveal 15 facing the anterior chamber 7. Once the laser focus is positioned at the initial depth $d_1$, the focus is scanned in multiple directions while being maintained at the initial depth. With reference to FIG. 14a, the multiple directions are the x direction and y direction, where the x direction is into the plane of FIG. 14a.

TABLE 2

| Tissue treated | Treatment pattern dimensions w[mm], h[mm], t[mm] | Opening cross section A [mm²] | Cell size w[μm], h[μm], t[μm] | Laser average power [W] | Laser repetition rate [kHz] | Laser pulse energy [μJ] | Procedure time [s] |
| --- | --- | --- | --- | --- | --- | --- | --- |
| Trabecular meshwork | 1.5, 0.2, 0.2 | 0.3 | 3, 3, 3 | 0.9 | 300 | 3 | 7.4 |
| Trabecular meshwork | 2, 0.2, 0.2 | 0.4 | 4, 4, 4 | 1 | 200 | 5 | 6.3 |
| Trabecular meshwork | 0.5, 0.2, 0.5 | 0.1 | 5, 5, 5 | 0.75 | 50 | 15 | 8.0 |
| Trabecular meshwork | 0.5, 0.2, 0.5 | 0.1 | 5, 5, 5 | 0.14 | 10 | 14 | 40.0 |
| Trabecular meshwork | 0.5, 0.2, 1.0 | 0.1 | 10, 10, 10 | 0.35 | 10 | 35 | 10.0 |
| Trabecular meshwork | 0.75, 0.25, 0.35 | 0.1875 | 10, 10, 10 | 0.7 | 20 | 35 | 3.3 |

With reference to FIGS. 11, 12a, 12b, 13, 14a and 14b, in one type of laser scanning procedure, the scanning begins at the end of the treatment pattern P1 adjacent the anterior chamber 7 and proceeds in a direction that generally corresponds to the direction of propagation of the laser beam 701. More specifically, and with reference to FIG. 14a, the laser scanning proceeds in the z direction toward an anatomical structure, e.g., the inner wall 18a of the Schlemm's canal 18, while the direction of propagation of the laser 701 also proceeds toward same anatomical structure, e.g., the inner wall 18a of the Schlemm's canal 18.

Laser scanning in this manner, however, may be ineffective at producing the desired opening 902 between the With reference to FIG. 14b, the raster scanning in the multiple directions results in the photodisruption of the initial layer 904 of tissue and the formation of a layer of bubbles 906 at the initial layer of tissue. The focus of the laser beam 701 is then moved in the z direction toward the inner wall 18a of the Schlemm's canal 18 to another depth $d_2$. This depth $d_2$ places the laser focus at a subsequent layer 908 of tissue deeper than the initial layer 904. For example, the deeper layer of tissue may comprise the uveal 15 of the trabecular meshwork 12. Once the laser focus is positioned at the subsequent layer 908, the focus is raster scanned in multiple directions while being maintained at that depth. However, in this instance, the layer of bubbles 906 scatters the incident laser light, effectively blocking further treatment of the tissue at the subsequent layer 908.

With reference to FIGS. 11, 12a, 12b, 13, 15a-15g, in accordance with embodiments disclosed the above ineffective laser treatment is avoided by implementing a laser scanning procedure, whereby the laser scanning begins at the end of the treatment pattern P1 adjacent the Schlemm's canal 18 and proceeds in a direction generally opposite to or against the direction of propagation of the laser beam 701. More specifically, and with reference to FIG. 15a, the laser scanning starts at an anatomical structure, e.g., the inner wall 18a of the Schlemm's canal 18 and proceeds away from that structure in the z direction toward the anterior chamber 7, while the direction of propagation of the laser beam 701 proceeds toward the that structure.

With this scanning procedure, the laser beam of femtosecond pulses is focused within a volume of ocular tissue at an initial depth or distance from a surface of the volume of tissue. An initial layer of tissue at the initial depth is treated, which generates a layer of bubbles at the area of the initial layer. After treatment of the initial layer of tissue, the laser is refocused to a subsequent layer of tissue that is shallower than the initial layer of tissue, i.e., at a depth that is closer to the surface of the volume of ocular tissue than the initial depth. Since the layer of bubbles at the area of the initial layer is below the second layer, the bubbles do not obstruct the second layer. This process is repeated until the laser scans, layer-by-layer through the volume of ocular tissue to the surface of the volume of tissue.

Figure 15A:
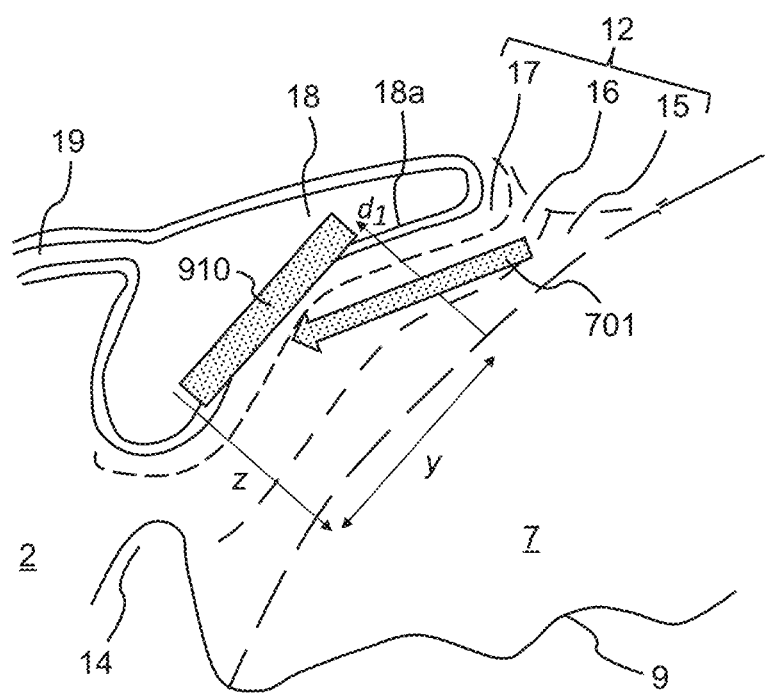
FIGS. 15a-15g are a series of schematic illustrations of a laser scanning process based on the treatment pattern of FIGS. 12a and 12b, where the scanning begins adjacent the Schlemm's canal and proceeds toward the anterior chamber.

An example of this scanning procedure within the context of glaucoma surgery is illustrated in FIGS. 15a-15g. In FIG. 15a, the focus of the laser beam 701 is initially located at a depth $d_1$. This depth $d_1$ places the laser focus in an initial layer 910 of tissue. For example, initial layer 910 of tissue may comprise the inner wall 18a of the Schlemm's canal 18. Once the laser focus is positioned at the initial depth $d_1$, the focus is scanned in multiple directions while being maintained at the initial depth $d_1$. With reference to FIG. 15a, the multiple directions are the x direction and y direction, where the x direction is into the plane of FIG. 15a.

Figure 15B:
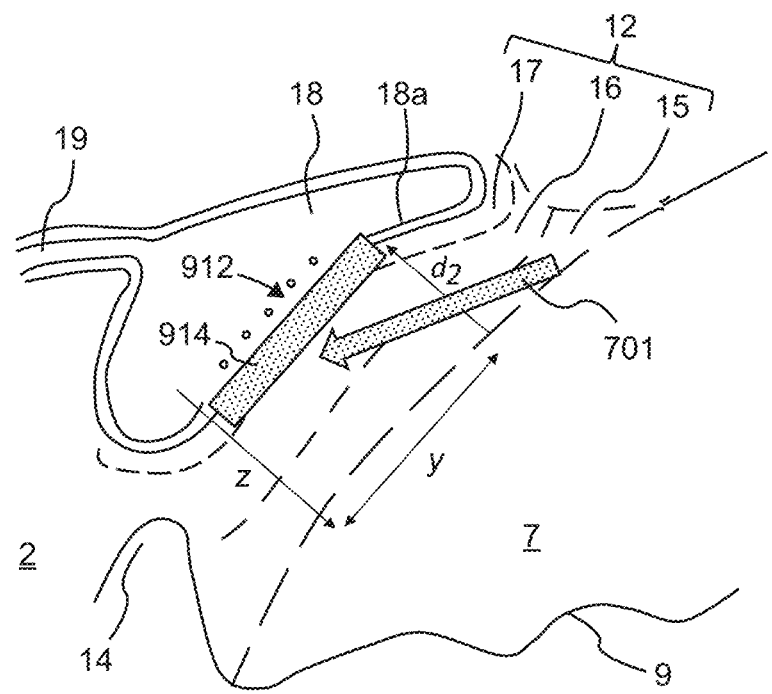

With reference to FIG. 15b, the laser scanning in multiple directions results in the photodisruption of the initial layer 910 of tissue and the formation of a layer of bubbles 912 at the location of the initial layer of tissue. The focus of the laser beam 701 is then moved in the z direction toward the anterior chamber 7 to a subsequent depth $d_2$. The subsequent depth $d_2$ places the laser focus at a subsequent layer 914 of tissue less deep than the initial layer 910 of tissue. For example, the subsequent layer 914 of tissue may comprise a portion of the inner wall 18a of the Schlemm's canal 18, the juxtacanalicular tissue 17, and the corneoscleral meshwork 16. Once the laser focus is positioned at the subsequent depth $d_2$, the focus is scanned in multiple directions while being maintained at the subsequent depth $d_2$. Since the layer of bubbles 912 is beneath the subsequent layer 914, the bubbles do not obstruct laser access to or block photodisruption of the subsequent layer.

Figure 15C:
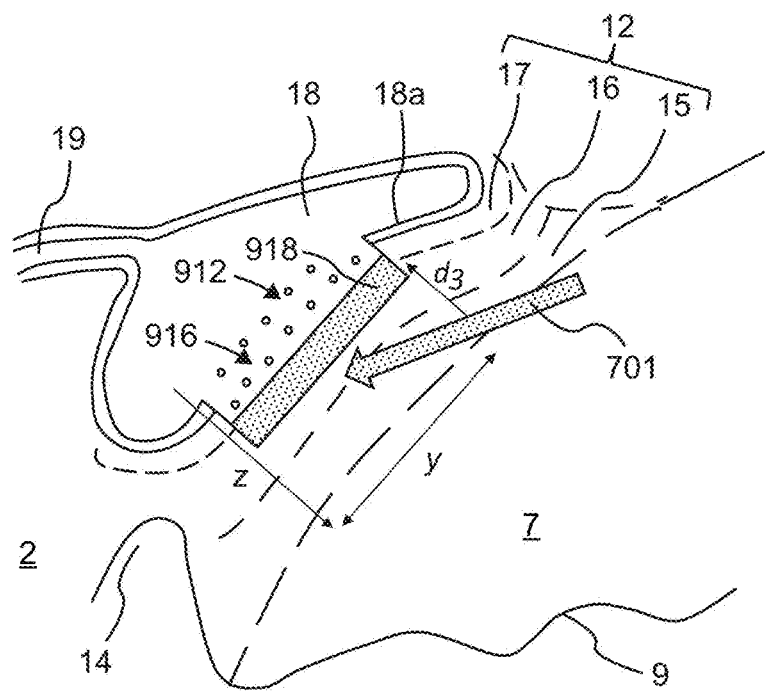

With reference to FIG. 15c, the laser scanning in multiple directions results in the photodisruption of the subsequent layer 914 of tissue and the formation of a layer of bubbles 916 at the location of the subsequent layer of tissue. The focus of the laser beam 701 is then moved in the z direction toward the anterior chamber 7 to a subsequent depth $d_3$. The subsequent depth $d_3$ places the laser focus at a subsequent layer 918 of tissue less deep than the subsequent layer 914 of tissue. For example, the subsequent layer 914 of tissue may comprise a portion of the juxtacanalicular tissue 17 and the corneoscleral meshwork 16. Once the laser focus is positioned at the subsequent depth $d_3$, the focus is scanned in multiple directions while being maintained at the subsequent depth $d_3$. Since the layers of bubbles 912, 916 are beneath the subsequent layer 918, the bubbles do not obstruct laser access to or block photodisruption of the subsequent layer.

Figure 15D:
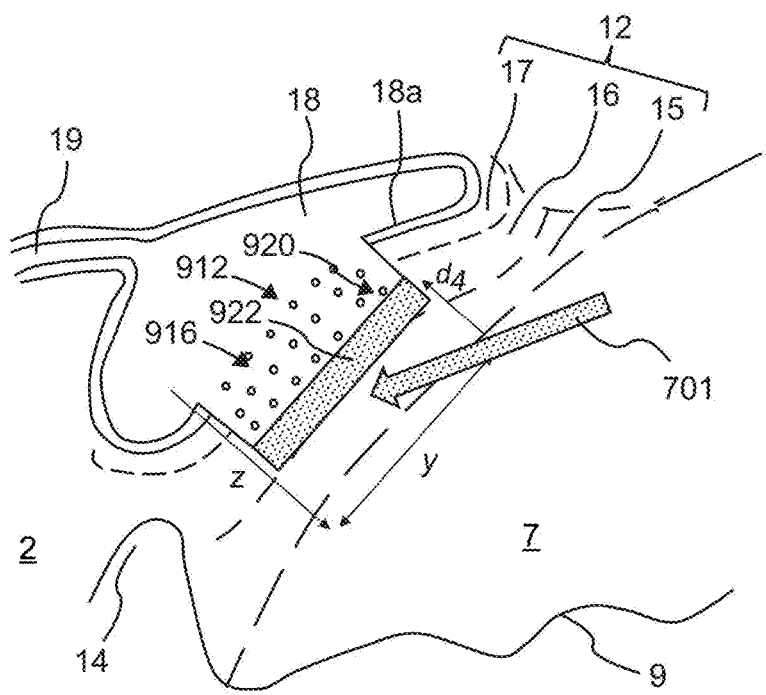

With reference to FIG. 15d, the laser scanning in multiple directions results in the photodisruption of the subsequent layer 918 of tissue and the formation of a layer of bubbles 920 at the location of the subsequent layer of tissue. The focus of the laser beam 701 is then moved in the z direction toward the anterior chamber 7 to a subsequent depth $d_4$. The subsequent depth $d_4$ places the laser focus at a subsequent layer 922 of tissue less deep than the subsequent layer 918 of tissue. For example, the subsequent layer 922 of tissue may comprise a portion of the corneoscleral meshwork 16 and the uveal 15. Once the laser focus is positioned at the subsequent depth $d_4$, the focus is scanned in multiple directions while being maintained at the subsequent depth $d_4$. Since the layers of bubbles 912, 916, 920 are beneath the subsequent layer 922, the bubbles do not obstruct laser access to or block photodisruption of the subsequent layer.

Figure 15E:
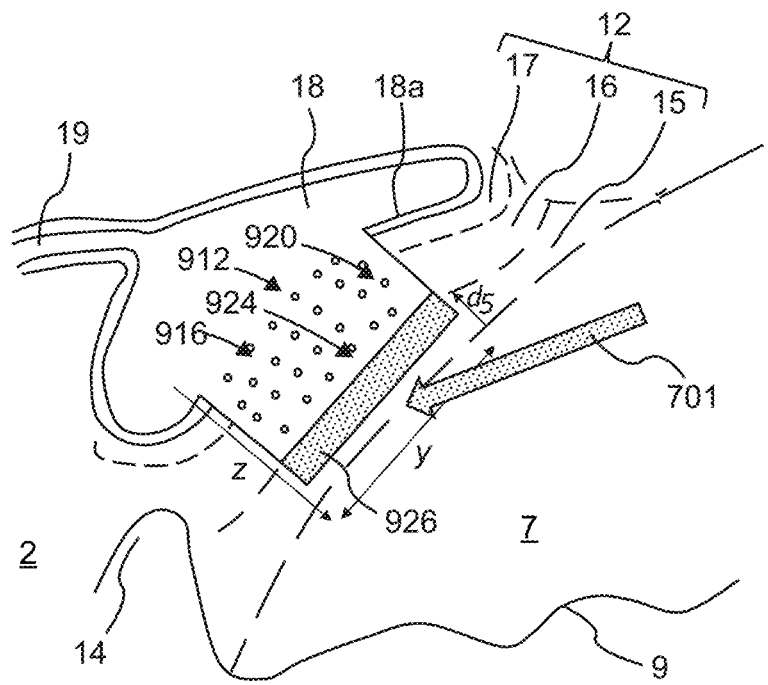

With reference to FIG. 15e, the laser scanning in multiple directions results in the photodisruption of the subsequent layer 922 of tissue and the formation of a layer of bubbles 924 at the location of the subsequent layer of tissue. The focus of the laser beam 701 is then moved in the z direction toward the anterior chamber 7 to a subsequent depth $d_5$. The subsequent depth $d_5$ places the laser focus at a subsequent layer 926 of tissue less deep than the subsequent layer 922 of tissue. For example, the subsequent layer 926 of tissue may comprise the uveal 15. Once the laser focus is positioned at the subsequent depth $d_5$, the focus is scanned in multiple directions while being maintained at the subsequent depth $d_5$. Since the layers of bubbles 912, 916, 920, 924 are beneath the subsequent layer 926, the bubbles do not obstruct laser access to or block photodisruption of the subsequent layer.

Figure 15F:
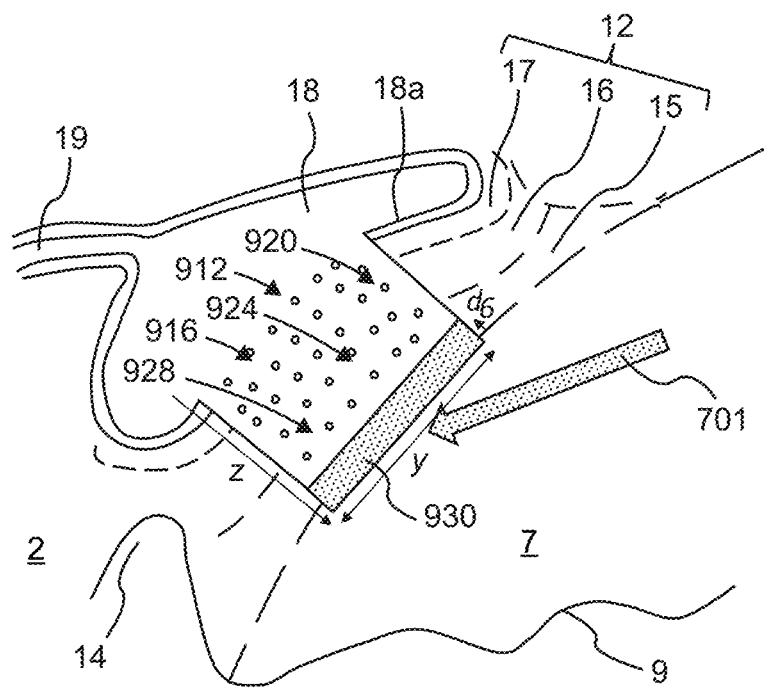

With reference to FIG. 15f, the laser scanning in multiple directions results in the photodisruption of the subsequent layer 926 of tissue and the formation of a layer of bubbles 928 at the location of the subsequent layer of tissue. The focus of the laser beam 701 is then moved in the z direction toward the anterior chamber 7 to a subsequent depth $d_6$. The subsequent depth $d_6$ places the laser focus at a subsequent layer 930 of tissue less deep than the subsequent layer 926 of tissue. For example, the subsequent layer 930 of tissue may comprise the uveal 15 and the inner surface of the uveal facing the anterior chamber 7. Once the laser focus is positioned at the subsequent depth $d_6$, the focus is scanned in multiple directions while being maintained at the subsequent depth $d_6$. Since the layers of bubbles 912, 916, 920, 924, 928 are beneath the subsequent layer 930, the bubbles do not obstruct laser access to or block photodisruption of the subsequent layer.

Figure 15G:
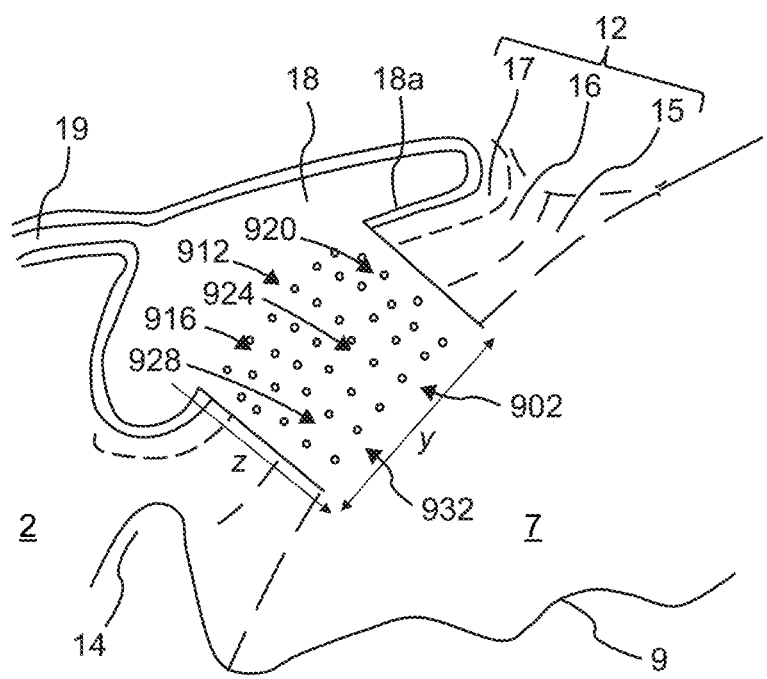

With reference to FIG. 15g, the laser scanning in multiple directions results in the photodisruption of the subsequent layer 930 of tissue and the formation of a layer of bubbles 932 at the location of the subsequent layer of tissue. Photodisruption of this subsequent layer 930 of tissue results in the formation of an opening 902 between the anterior chamber 7 and the Schlemm's canal 18, thus completing the laser treatment procedure.

Figure 16A:
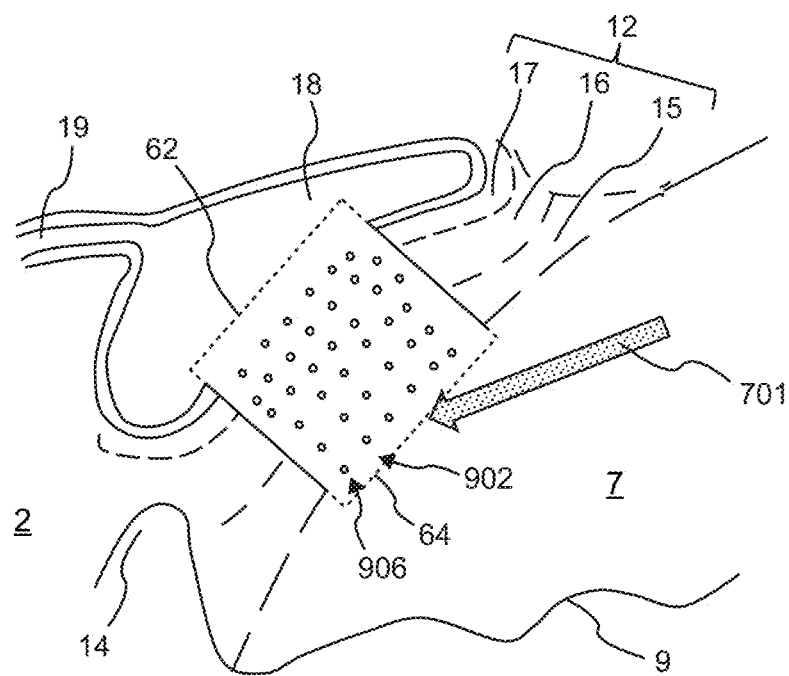
FIGS. 16a and 16b are a series of schematic illustrations of an optional laser scanning process through the opening of FIG. 15g, where the scanning begins at the end of the opening adjacent the anterior chamber and proceeds toward the Schlemm's canal.
Figure 16B:
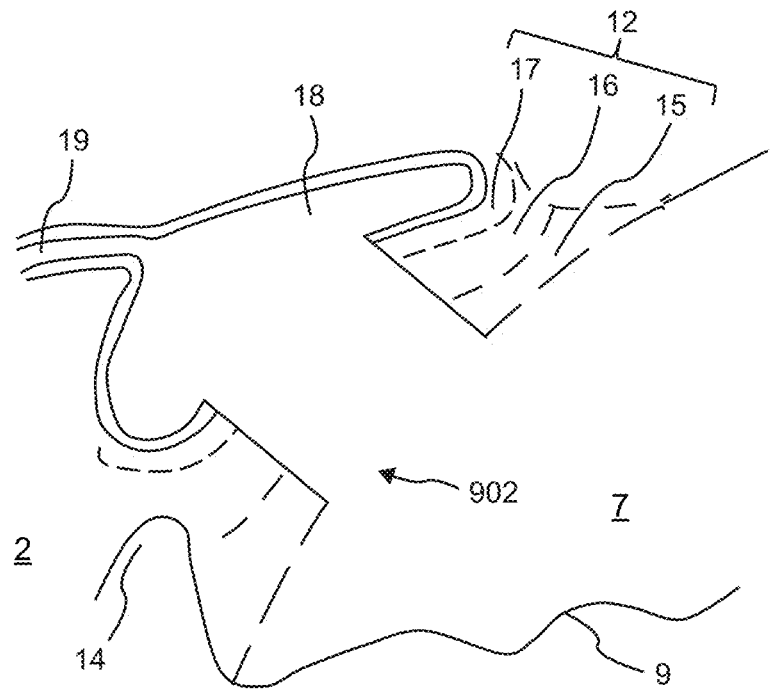

With reference to FIG. 16a, upon completion of the laser scanning the opening 902 may be partially obstructed or occluded by the gas bubbles 912, 916, 920, 924, 928 created during treatment. Thus, in accordance with embodiments disclosed herein, the direction of the laser scanning described with reference to FIGS. 15a-15g may be reversed in order to push any remaining bubbles into the Schlemm's canal 18 thereby clearing the opening 902, as shown in FIG. 16b.

Figure 17:
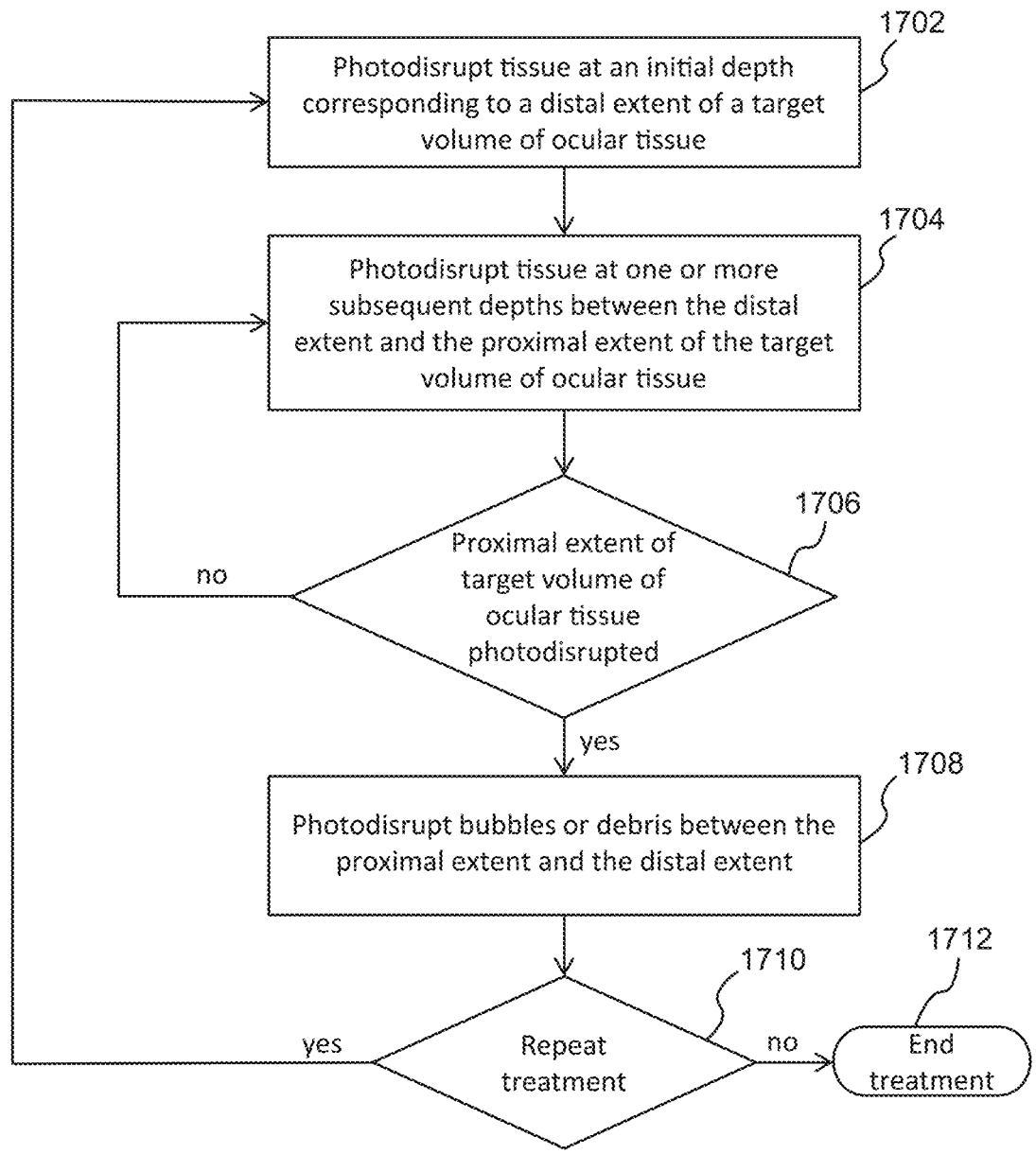
FIG. 17 is a flowchart of a method of treating a volume of ocular tissue.

FIG. 17 is a flowchart of a method of treating a target volume of ocular tissue with a laser having a direction of propagation toward the target volume of ocular tissue. With reference to FIGS. 12a and 12b, the target volume 60 of ocular tissue is characterized by a distal extent 62, a proximal extent 64, and a lateral extent 66. The distal extent 62 corresponds to the part or point of the target volume 60 that is most distal along the direction of propagation of the laser beam 701. The proximal extent 64 corresponds to the part or point of the target volume 60 that is most proximal along the direction of propagation of the laser beam 701. The lateral extent 66 corresponds to the distance or width w of the target volume 60 along the circumference angle.

The method, which may be performed by the integrated surgical system 1000 of FIGS. 7-10b, begins at a point in a surgical procedure where access to the irido-corneal angle has already been obtained and the target volume 60 of ocular tissue has already been identified for treatment. Systems and methods for accessing the irido-corneal angle are described in U.S. patent application Ser. No. 16/036,883, entitled Integrated Surgical System and Method for Treatment in the Irido-Corneal Angle of the Eye, the disclosure of which is hereby incorporated by reference. Systems and method for identifying volumes of ocular tissue for treatment and designing treatment patterns reference are described in U.S. patent application Ser. No. 16/125,588, entitled Non-Invasive and Minimally Invasive Laser Surgery for the Reduction of Intraocular Pressure in the Eye, the disclosure of which is hereby incorporated by reference.

At block 1702, the integrated surgical system 1000 initially photodisrupts tissue at an initial depth $d_1$ corresponding to the distal extent 62 of the target volume 60 of ocular tissue is. To this end, and with reference to FIG. 15a, the integrated surgical system 1000 focuses light from a femtosecond laser beam 701 at a spot in the tissue at the initial depth $d_1$ and applies optical energy to the tissue, which energy is at a level sufficient to photodisrupt the tissue. Optical energy is applied by scanning the laser beam 701 in multiple directions defining an initial treatment plane 910 at the initial depth $d_1$ to thereby photodisrupt an initial layer of tissue of the target volume of ocular tissue. With reference to FIG. 13, the scanning may be in the form of a raster scan where the laser is scanned in a first direction along the lateral extent 66, i.e., the x direction, and then slightly repositioned in a second direction. i.e., the y direction, and then scanned again along the lateral extent.

As an additional aspect of the initial photodisruption process of block 1702, the integrated surgical system 1000 may detect the distal extent 62 of the target volume of ocular tissue. To this end, in one configuration images captured by the OCT imaging apparatus 300 are processed by the control system 100 to detect the distal extent 62 of the target volume using known techniques. In another configuration, the integrated surgical system 1000 may include a multiphoton imaging apparatus (not shown) that provides a visual indication on a display of the user interface 110 that is indicative of the location of the focus of the laser beam 701 relative to the distal extent 62 of the target volume 60 of ocular tissue. The integrated surgical system 1000 may also determine the lateral extent 66 of the target volume 60 of ocular tissue based on OCT imaging.

At block 1704 and with reference to FIGS. 15b-15f, the integrated surgical system 1000 subsequently photodisrupts tissue at one or more subsequent depths $d_2$-$d_6$ between the distal extent 62 of the target volume 60 of ocular tissue and the proximal extent 64 of the target volume of ocular tissue is by moving a focus of the laser beam 701 in a direction opposite the direction of propagation of the laser. To this end, the integrated surgical system 1000 focuses light from a femtosecond laser beam 701 at a spot in the tissue at the one or more subsequent depths $d_2$-$d_6$ and applies optical energy to the tissue, which energy is at a level sufficient to photodisrupt the tissue. Optical energy is applied by scanning the laser beam 701 in multiple directions defining a subsequent treatment plane 914, 918, 922, 926, 930 at a respective different depth $d_2$-$d_6$, to thereby photodisrupt one or more subsequent layers of tissue of the target volume 60 of ocular tissue. With reference to FIG. 13, the scanning may be in the form of a raster scan where the laser is scanned in a first direction along the lateral extent 66, i.e., the x direction, and then slightly repositioned in a second direction. i.e., the y direction, and then scanned again along the lateral extent.

As an additional aspect of the subsequent photodisruption process of block 1704, the integrated surgical system 1000 may detect the proximal extent 64 of the target volume 60 of ocular tissue. To this end, in one configuration images captured by the OCT imaging apparatus 300 are processed by the control system 100 to detect the proximal extent 64 of the target volume 60 using known techniques. In another configuration, the integrated surgical system 1000 may include a multiphoton imaging apparatus (not shown) that provides a visual indication on a display of the user interface 110 that is indicative of the location of the focus of the laser beam 701 relative to the proximal extent 64 of the target volume 60 of ocular tissue. In yet another configuration, the integrated surgical system 1000 may include an opto-mechanical imaging apparatus (not shown) that provides a visual indication on a display of the user interface 110 that is indicative of the location of the focus of the laser beam 701 relative to the proximal extent 64 of the target volume 60 of ocular tissue.

At block 1706, the integrated surgical system 1000 determines if the proximal extent 64 of the target volume 60 of ocular tissue has been photodisrupted. If the proximal extent 64 has not been photodisrupted, the process return to block 1704 and the integrated surgical system 1000 repeats the photodisrupting at one or more subsequent depths until tissue at the proximal extent 64 of the target volume 60 of ocular tissue is photodisrupted.

Returning to block 1706 and with reference to FIG. 16a, if the proximal extent 64 has been photodisrupted, the process proceeds to block 1708 and the integrated surgical system 1000 photodisrupts tissue debris or bubbles 906 between the proximal extent 64 of the target volume 60 of ocular tissue and the distal extent 62 of the target volume by moving the focus of the laser beam 701 in the direction of propagation of the laser. To this end, the integrated surgical system 1000 focuses light from a femtosecond laser beam 701 at a spot in the volume of tissue debris or bubbles 906 at the one or more subsequent depths and applies optical energy to the tissue debris or bubbles. Optical energy is applied by scanning the laser beam 701 in multiple directions along one or more of the previously-scanned treatment planes 910, 914, 918, 922, 926, 930 to photodisrupt tissue debris or bubbles 906 between the proximal extent 64 and the distal extent 62 of the photodisrupted target volume 60.

At block 1710, the integrated surgical system 1000 may determine to repeat the treatment of the photodisrupted target volume 60 of ocular tissue or to end the treatment. If treatment is repeated, the process returns to block 1702, where the integrated surgical system 1000 repeats the initial photodisrupting of tissue, and then proceeds to blocks 1704 and 1706, where the system repeats the subsequent photodisrupting of tissue one or more times. If treatment is not to be repeated, the process proceeds to block 1712, where treatment ends.

Regarding the use of a multiphoton imaging apparatus to detect the distal extent 62 of the target volume of ocular tissue, or the proximal extent 64 of the target volume, such an apparatus is configured to present an image of a second harmonic light that results from an encounter between the focus of the laser beam 701 and tissue. When the focus of the laser beam 701 is not encountering tissue, the intensity of the second harmonic light is zero or very low. When the focus is encountering tissue, the intensity of the second harmonic light increases. Based on this, a distal extent 62 such as shown in FIGS. 12a and 12b may be detected by first advancing the focus of the laser beam 701 through the trabecular meshwork 12 and the inner wall 18a of the Schlemm's canal and into the Schlemm's canal 18, where the focus will not encounter light and the intensity of the second harmonic light is zero or very low, and then retracting the focus back toward the inner wall 18a of the Schlemm's canal and detecting that the focus is at the inner wall when an increase in the intensity of the second harmonic light is noted on the display.

Regarding the use of an opto-mechanical imaging apparatus to detect the proximal extent 64 of the target volume 60 of ocular tissue, such an apparatus is configured to direct a first beam of light and a second beam of light to be incident with the target volume and to align the first beam of light and the second beam of light relative to each other and relative to the laser beam such that the first beam of light and the second beam light intersect at a point corresponding to the focus of the laser. The apparatus is also configured to capture an image of a first spot corresponding to the first beam of light, and a second spot corresponding to the second beam of light relative to the proximal extent 64 of the target volume 60 of ocular tissue. The first and second spots appear in the image as two separate visible spots on the surface of the proximal extent 64 when the focus is away from the surface, and as a single, overlapping spot when the focus is on the surface. Accordingly, the proximal extent 64 is detected when the spots overlap.

With reference to FIGS. 7-10b, a surgical system 1000 for implementing the method of FIG. 17 includes a first optical subsystem 1001 and a second optical subsystem 1002. The first optical subsystem 1001 includes the exit lens 710 of a focusing objective head 700 and the window 801 of a patient interface 800. The second optical subsystem 1002 including a laser source 200 configured to output a laser beam 201/701 and a plurality of components 1003 configured to one or more of focus, scan, and direct the laser beam through the focusing objective head, in a direction of propagation toward the target volume of ocular tissue.

The surgical system 1000 further includes a control system 100 coupled to the second optical subsystem 1002 and configured to control the focus and scan of the laser beam 701 to photodisrupt tissue at an initial depth corresponding to the distal extent of the target volume of ocular tissue. To this end, the control system 100 is configured to focus light from a femtosecond laser source 200 at a spot in the tissue at the initial depth and then apply optical energy to the tissue, where the energy is sufficient to photodisrupt tissue. The control system 100 controls the focus and scan of the laser beam 701 during application of optical energy by being further configured to scan the laser in multiple directions defining an initial treatment plane, to thereby photodisrupt an initial layer of tissue of the target volume of ocular tissue.

The control system 100 is also configured to control the focus and scan of the laser beam 701 to photodisrupt tissue at one or more subsequent depths between the distal extent of the target volume of ocular tissue and the proximal extent of the target volume of ocular tissue by moving a focus of the laser in a direction opposite the direction of propagation of the laser. To this end, the control system 100 is configured to focus light from a femtosecond laser source 200 at a spot in the tissue at a subsequent depth and then apply optical energy to the tissue, where the energy is sufficient to photodisrupt tissue. The control system 100 controls the focus and scan of the laser beam 701 during application of optical energy by being further configured to scan the laser in multiple directions defining a subsequent treatment plane, to thereby photodisrupt a subsequent layer of tissue of the target volume of ocular tissue.

The control system 100 is also configured to control the focus and scan of the laser beam 701 to photodisrupt tissue debris or bubbles between the proximal extent of the target volume of ocular tissue and the distal extent of the target volume by moving the focus of the laser in the direction of propagation of the laser, after photodisrupting the target volume of ocular tissue. The control system 100 is further configured to control the focus and scan of the laser beam 701 to repeat the initial photodisrupting of tissue and the subsequent photodisrupting of tissue one or more times.

Figure 18:
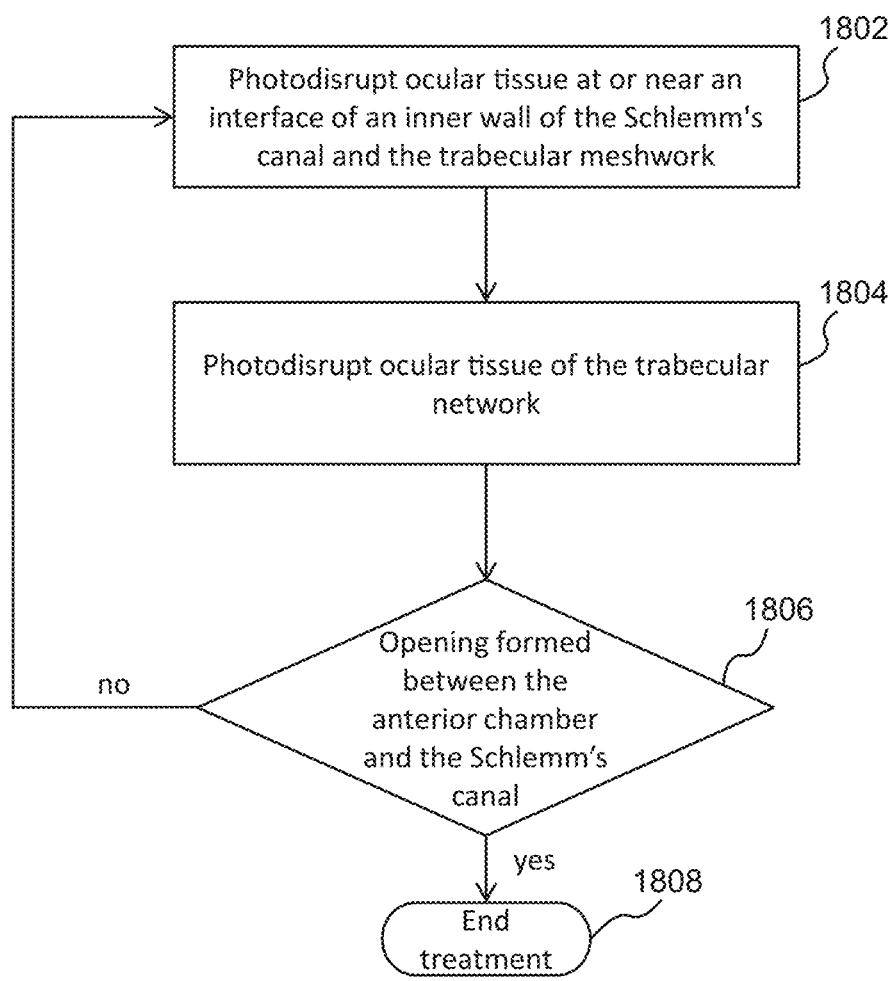
FIG. 18 is a flowchart of a method of treating an eye comprising an anterior chamber, a Schlemm's canal, and a trabecular meshwork.

FIG. 18 is a flowchart of a method of treating an eye comprising an anterior chamber, a Schlemm's canal, and a trabecular meshwork therebetween. The method, which may be performed by the integrated surgical system 1000 of FIGS. 7-10b, begins at a point in a surgical procedure where access to the irido-corneal angle has already been obtained and one or more anatomical structures of the eye that are to be treated have been located.

At block 1802 and with reference to FIGS. 15a and 15b, the integrated surgical system 1000 initially photodisrupts ocular tissue at or near an interface of an inner wall 18a of the Schlemm's canal 18 and the trabecular meshwork 12. To this end, the integrated surgical system 1000 focuses light from a femtosecond laser beam 701 at a spot in the ocular tissue at or near the interface of the inner wall 18a of the Schlemm's canal 18 and the trabecular meshwork 12 and applies optical energy to the tissue, which energy is at a level sufficient to photodisrupt the tissue.

As an additional aspect of the initial photodisruption process of block 1802, the integrated surgical system 1000 may detect ocular tissue at or near the interface of the inner wall 18a of the Schlemm's canal 18 and the trabecular meshwork 12. To this end, in one configuration images captured by the OCT imaging apparatus 300 are processed by the control system 100 to detect the interface of the inner wall 18a of the Schlemm's canal 18 and the trabecular meshwork 12 using known techniques. In another configuration, the integrated surgical system 1000 may include a multiphoton imaging apparatus (not shown) that provides a visual indication on a display of the user interface 110 that is indicative of the location of the focus of the laser beam 701 relative to the interface of the inner wall 18a of the Schlemm's canal 18 and the trabecular meshwork 12. The integrated surgical system 1000 may also determine a lateral extent 66 of ocular tissue to be photodisrupted based on OCT imaging.

At block 1804 and with reference to FIGS. 15c-15f, the integrated surgical system 1000 subsequently photodisrupts ocular tissue of the trabecular meshwork 12. To this end, the integrated surgical system 1000 focuses light from a femtosecond laser beam 701 at a spot in tissue of the trabecular meshwork 12 and applies optical energy to the tissue, which energy is at a level sufficient to photodisrupt the tissue.

As an additional aspect of the subsequent photodisruption process of block 1804, the integrated surgical system 1000 may detect a proximal extent of tissue of the trabecular meshwork. To this end, in one configuration images captured by the OCT imaging apparatus 300 are processed by the control system 100 to detect the proximal extent 64 of the tissue of the trabecular meshwork using known techniques. In another configuration, the integrated surgical system 1000 may include a multiphoton imaging apparatus (not shown) that provides a visual indication on a display of the user interface 110 that is indicative of the location of the focus of the laser beam 701 relative to the proximal extent 64 of the tissue of the trabecular meshwork. In yet another configuration, the integrated surgical system 1000 may include an opto-mechanical imaging apparatus (not shown) that provides a visual indication on a display of the user interface 110 that is indicative of the location of the focus of the laser beam 701 relative to the proximal extent 64 of the tissue of the trabecular meshwork.

At block 1806, the integrated surgical system 1000 determines if an opening is formed between the anterior chamber and the Schlemm's canal. If an opening has not been formed, the process return to block 1802 and the integrated surgical system 1000 repeats the initial photodisrupting of ocular tissue and then proceeds to block 1804 and repeats the subsequent photodisrupting of ocular tissue one or more times until an opening is formed between the anterior chamber and the Schlemm's canal. If an opening has been formed, the process proceeds to block 1808, where treatment ends.

With reference to FIGS. 7-10b, a surgical system 1000 for implementing the method of FIG. 18 includes a first optical subsystem 1001 and a second optical subsystem 1002. The first optical subsystem 1001 includes the exit lens 710 of a focusing objective head 700 and the window 801 of a patient interface 800. The second optical subsystem 1002 including a laser source 200 configured to output a laser beam 201/701 and a plurality of components 1003 configured to one or more of focus, scan, and direct the laser beam through the focusing objective head, in a direction of propagation toward the target volume of ocular tissue.

The surgical system 1000 further includes a control system 100 coupled to the second optical subsystem 1002 and configured to control the focus and scan of the laser beam 701 to initially photodisrupt ocular tissue at or near an interface of an inner wall of the Schlemm's canal and the trabecular meshwork. To this end, the control system 100 is configured to focus light from a femtosecond laser source 200 at a spot in the ocular tissue at or near the interface of the inner wall of the Schlemm's canal and the trabecular meshwork, and then apply optical to the tissue, where the energy is sufficient to photodisrupt tissue.

The control system 100 is also configured to control the focus and scan of the laser beam 701 to subsequently photodisrupt tissue of the trabecular meshwork. To this end, the control system 100 is configured to focus light from a femtosecond laser at a spot in tissue of the trabecular meshwork, and then apply optical energy to the tissue, where the energy is sufficient to photodisrupt tissue. The control system 100 is further configured to control the focus and scan of the laser beam 701 to repeat the initial photodisrupting of ocular tissue and the subsequent photodisrupting of ocular tissue one or more times until an opening is formed between the anterior chamber and the Schlemm's canal.

Figure 20:
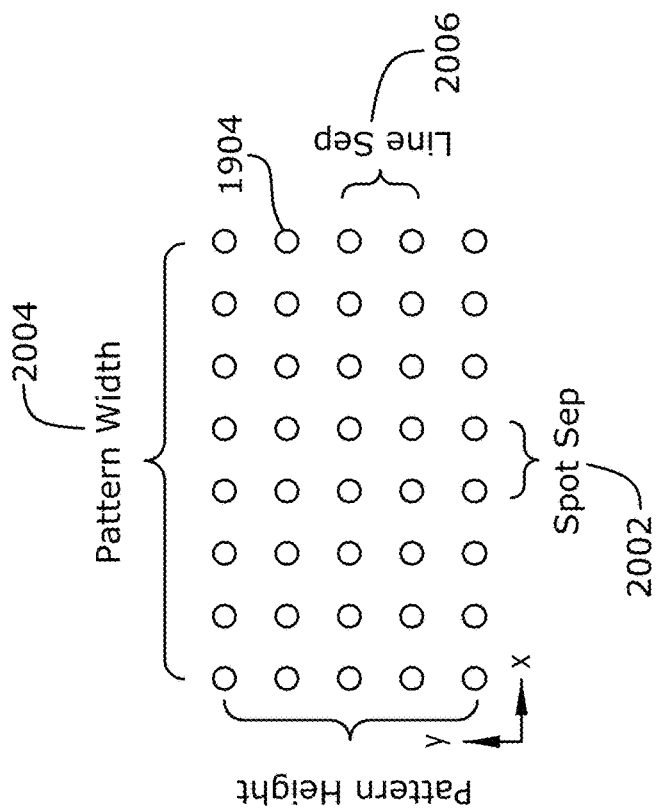
FIG. 20 is a schematic illustration of a two-dimensional treatment layer defined by an array of spots.
Figure 19:
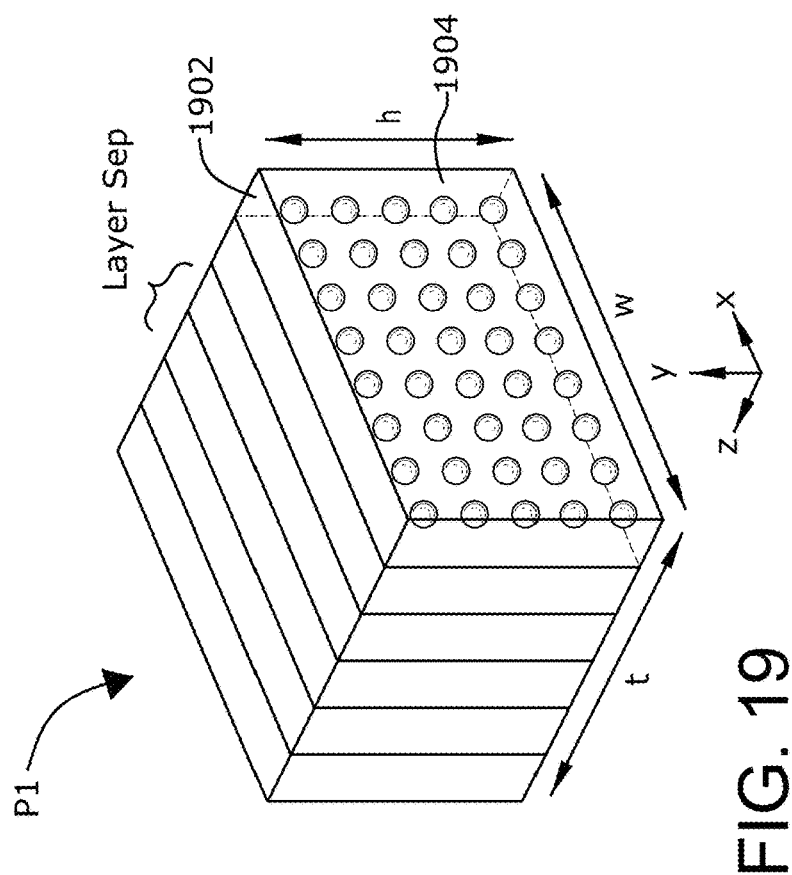
FIG. 19 is a schematic illustration of a three-dimensional laser treatment pattern formed by a number of stacked two-dimensional treatment planes or layers.

With reference to FIGS. 19 and 20, as previously described, a 3D treatment pattern P1 may be defined by a number of 2D treatment layers 1902 or treatment planes that are stacked to form a 3D treatment pattern characterized by a width w, height h, and depth or thickness t. Each individual treatment layer 1902 is in turn characterized by a pattern height h (equal to the height h of the 3D treatment pattern P1) and a pattern width w (equal to the width w of the 3D treatment pattern P1) and comprises an array of spots 1904 spaced apart to establish or fit within the height and width. The pattern width w corresponds to a distance along the circumference of the corneal angle parallel to the trabecular meshwork. This direction is also known as the circumferential direction. The pattern height h corresponds to a distance transverse to the circumference of the corneal angle perpendicular to the trabecular meshwork. This direction is also known as the azimuthal direction.

Each spot 1904 in the treatment pattern P1 corresponds to a site within a target volume of ocular tissue where optical energy is applied at a laser focus to create a micro-photodisruption site. With reference to FIG. 20, each spot 1904 in a treatment layer 1902 is separated from a neighboring spot by programmable distances called spot separation (Spot Sep) and a line separation (Line Sep). A treatment layer 1902 is completed with the programmed pattern width w and pattern height h is achieved. Each layer 1902 in the 3D treatment pattern P1 is separated from a neighboring layer by a layer separation (Layer Sep).

A treatment pattern P1 may be defined by a set of programmable parameters, such as shown in Table 3.

TABLE 3

| Parameter | Minimum | Maximum |
| --- | --- | --- |
| width w | 10 µm | 2000 µm |
| height h | 10 µm | 2000 µm |
| depth/thickness t | 10 µm | 4000 µm |
| Spot Sep | 2 µm | 40 µm |
| Line Sep | 2 µm | 40 µm |
| Layer Sep | 2 µm | 200 µm |
| pulse energy | 0 µJ | 35 µJ |

Other, non-rectangular and more irregular treatment patterns can also be programmed and created in the tissue. These irregular patterns can still be decomposed to spots, lines, and layers and their extent characterized by width, height, and depth. Examples of irregular treatment patterns are described in U.S. patent application Ser. No. 16/838,858, entitled Method, System, and Apparatus for Generating Three-Dimensional Treatment Patterns for Laser Surgery of Glaucoma, the disclosure of which is hereby incorporated by reference.

In one example treatment pattern P1, the parameters are:
width=750 µm
height=250 µm
depth=350 µm
spot separation=10 µm
line separation=10 µm
layer separation=10 µm In one embodiment of laser treatment, such as described above with reference to FIGS. 15a-15g, each treatment layer 1902 is individually created by scanning the laser focus in two dimensions, e.g., width and height, or z and y, to the various spots 1904 defining the layer, while the focus is fixed at the third dimension, e.g., depth or Z. Once a treatment layer 1902 is created, the focus is moved in the depth or z direction and the next treatment layer in the stack is created. This process is repeated until all treatment layers 1902 in the 3D treatment pattern P1 are created.

Patient Customized Laser Treatment

As noted previously in this disclosure, femtosecond laser pulses treat tissue by a process called photodisruption in which tissue at the focus of a beam is disrupted to elemental gas. The intent of treating the tissue in this manner is to create or cut an aperture, opening, or channel through ocular tissue, and through which the intraocular pressure can be reduced. The "cutting efficiency" of a laser treatment is a function of laser fluence, which is the ratio of energy per pulse to the area over which the energy is delivered. The area over which the energy is delivered is referred to as a laser focus spot size. Once the laser fluence exceeds a breakdown threshold value, the tissue within a volume specified by the laser focus spot size is disrupted. If the laser fluence is less than the breakdown threshold, the focused laser does not affect the tissue. It is generally accepted that the breakdown threshold for ocular tissue is approximately 0.8 to 1.0 $\mu J/cm^2$.

In embodiments disclosed herein, femtosecond lasers treat the trabecular meshwork by focusing a beam of a femtosecond laser pulse through optics of a focusing objective head and a window of a patient interface, through the cornea, through the anterior chamber, and into a spot on the iridocorneal angle. The size (diameter) of the laser focus spot changes depending upon the number of optical aberrations introduced into the beam trajectory as it enters, and passes through the optics of the focusing objective head, the window of the patient interface, and the eye to the trabecular meshwork 12. The location of the trabecular meshwork 12 varies across the patient population due to anatomical differences in corneal anterior and posterior shape, corneal thickness, and corneal diameter. There is a unique beam trajectory for each patient, which leads to a unique set of optical aberrations. Therefore, there is variation in laser focus spot size across the patient population—and for a fixed energy—a different fluence, resulting in variation in cutting efficiency.

Disclosed herein are methods and systems that create homogeneous cutting efficiency across a patient population by combining biometric data, an anatomical model, and laser control to customize the delivery of laser energy to each patient. In some embodiments, the laser energy used to treat tissue in the irido-corneal angle is adjusted based on the optical anatomy of the eye. This laser energy adjustment is intended to compensate for the change in laser fluence resulting from optical aberrations of the eye, and optical and mechanical aberrations introduced by components of the laser treatment system, e.g., the optics of the focusing objective head and the window of the patient interface.

Disclosed laser treatment methods and systems deliver laser energy to optical tissue at energy levels that vary as a function of the location of the tissue being treated. For example, an energy delivery look up table may provide laser energy levels as a function of the location of a laser focus in a volume of ocular tissue in the irido-corneal angle of the eye, thereby enabling adjustments of laser energy during treatment.

Other disclosed methods and systems generate a laser energy delivery look up table that may be employed by the laser treatment methods and systems. These methods and systems generate look up tables based on simulated biometric data across a simulated patient population and use a graphics rendering model, such as a ray tracing model, to obtain spot size distributions for the laser focus at different simulated locations in anatomy of the eye. Energy levels may be assigned to different focus locations based on a respective spot size associated with the focus at the different locations.

Patient Biometric Data

Figure 21:
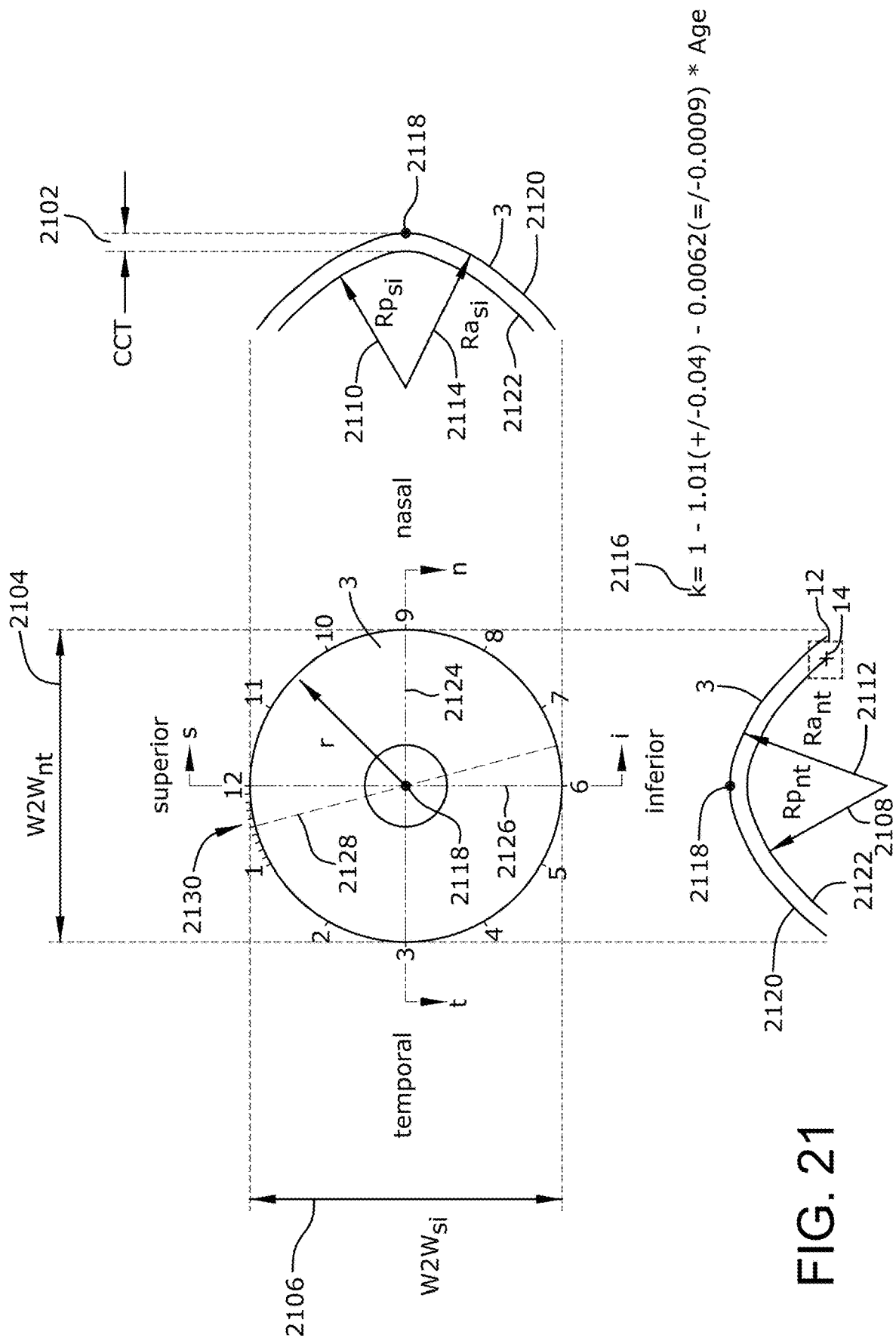
FIG. 21 is a schematic diagram of the cornea including a plan view from the top of the cornea, a superior-to-inferior cross-section through the superior-to-inferior meridian of the cornea, and a nasal-to-temporal cross-section through the nasal-to-temporal meridian of the cornea.

With reference to FIG. 21, which is a schematic illustration of a cornea of a left eye, the disclosed methods and systems may be based on biometric data, including various natural anatomical measurements of the eye and demographic data, e.g., patient age. "Natural" in this context means that the anatomical measurements of the eye are obtained without imparting deformation to the eye. For example, coupling a patient interface 800 to the eye, as shown in FIG. 9a, deforms the cornea. Accordingly, the natural anatomical measurements described herein are obtained in the absence of a coupling of a patient interface 800.

With continued reference to FIG. 21, the natural anatomical measurements may include one or more sets of measurements obtained relative to one or more meridians of the cornea 3. The meridians of the cornea 3 may be described in terms of clock time, and include for example, a 3-9 o'clock meridian 2124 (also referred to as a nasal-temporal meridian), and a 6-12 o'clock meridian 2126 (also referred to as a superior-inferior meridian). Numerous other meridians of the cornea 3 at respective clock times are present around the circumference of the cornea, however, for clarity of illustration only the nasal-temporal meridian 2124 and the superior-inferior meridian 2126 are shown in FIG. 21.

Natural anatomical measurements include:
1) the central corneal thickness (CCT) 2102 of the cornea 3, which corresponds to the difference in height between the anterior surface 2120 of the cornea and the posterior surface 2122 of the cornea at the apex 2118 of the cornea;
2) one or more white-to-white diameters (W2W), which may include for example, a nasal-temporal W2W diameter ($W2W_{nt}$) 2104 along a nasal-temporal meridian 2124, or a superior-inferior W2W diameter ($W2W_{si}$) 2106 along a superior-inferior meridian 2126, or a W2W diameter for any other meridian of the cornea 3;
3) one or more anterior cornea radii of curvature (Ra), which may include for example, a nasal-temporal anterior cornea radius of curvature ($Ra_{nt}$) 2112 along a nasal-temporal meridian 2124, or a superior-inferior anterior cornea radius of curvature ($Ra_{si}$) 2114 along a superior-inferior meridian 2126, or an anterior cornea radius of curvature (Ra) for any other meridian of the cornea 3;
4) one or more posterior cornea radii of curvature (Rp), which may include for example, a nasal-temporal posterior cornea radius of curvature ($Rp_{nt}$) 2108 derived from a nasal-temporal anterior cornea radius of curvature ($Ra_{nt}$) 2112, or a superior-inferior posterior cornea radius of curvature ($Rp_{si}$) 2110, derived from a superior-inferior anterior cornea radius of curvature ($Ra_{si}$) 2114, or a posterior cornea radius of curvature (Rp) for any other meridian of the cornea 3, each of which is derived from a corresponding anterior cornea radius of curvature (Ra).

The natural anatomical measurements may be obtained using measurement equipment that is commonly found in ophthalmic settings such as the IOLMaster or the Orbscan. Germane biometric data that these devices calculate are the CCT 2102, the anterior cornea radius of curvature Ra along numerous meridians of the cornea (including but not limited to the nasal-temporal anterior cornea radius of curvature ($Ra_{nt}$) 2112 and the superior-inferior anterior cornea radius of curvature ($Ra_{si}$) 2114), and the W2W diameter along numerous meridians of the cornea (including but not limited to the nasal-temporal W2W diameter ($W2W_{nt}$) 2104 and the superior-inferior W2W diameter ($W2W_{si}$) 2106).

The natural posterior cornea radii of curvature Rp may be derived from the anterior cornea radius of curvature Ra using a known relationship. For example, the ratio of the anterior-to-posterior radius of curvature has been comprehensively measured in the literature and is a stable relationship regardless of age, gender, or race. See, e.g., M. Dubbelman, V.A.D.P Sicam, and G. L. Van der Heijde, "The shape of the anterior and posterior surface of the aging human cornea," *Vision Research* (2006) 46, 993-1001. The ratio of the natural anterior radius of curvature Ra to the natural posterior radius of curvature Rp is approximately 1.22. Accordingly, a natural posterior cornea radius of curvature Rp may be derived using the following equation:

$$Rp = Ra/1.22 \quad\quad (Eq. 1)$$

For example, the nasal-temporal radius of curvature ($Rp_{nt}$) 2108 and the superior-inferior posterior cornea radius of curvature ($Rp_{si}$) 2110 may be respectively derived based on the nasal-temporal anterior cornea radius of curvature ($Ra_{nt}$) 2112 and the superior-inferior anterior cornea radius of curvature ($Ra_{si}$) 2114 using Eq 1.

With continued reference to FIG. 21, regarding the anterior cornea radii of curvature and the posterior cornea radii of curvature, because the anterior surface 2120 of the cornea 3 and the posterior surface 2122 of the cornea are aspherical the respective radii of curvature of these surfaces varies from point to point on the surface. For example, considering the cross-section of the cornea 3 along the nasal-temporal meridian 2124 shown in FIG. 21, the measures of $Ra_{nt}$ 2112 and $Rp_{nt}$ 2108 vary from point to point along the arc of the cross-section. Similarly, the measures of $Ra_{si}$ 2114 and $Rp_{si}$ 2110 vary along the arc of the cross-section of the cornea 3 along the superior-inferior meridian 2126. Furthermore, the anterior surface 2120 of the cornea 3 and the posterior surface 2122 of the cornea have different shapes, with the posterior surface curving more sharply than the anterior surface.

Other biometric data of the patient includes an age-based posterior conic constant (k) 2116. The age-based posterior conic constant (k) mathematically describes the deviation of the posterior surface 2122 of the cornea 3 from a purely spherical surface. The age-based posterior conic constant (k) is determined from an empirical relationship determined from clinical data and is a function of patient age. This relationship is given as:

$$k = 1 - 1.01(\pm 0.04) - 0.0062(\pm 0.0009)*Age \quad\quad (Eq. 2)$$

Having thus described the types of biometric data relevant to the methods and system disclosed herein, a description of a method and system of laser treatment of a patient based on the biometric data of that particular patient follows.

Laser Treatment

Figure 22:
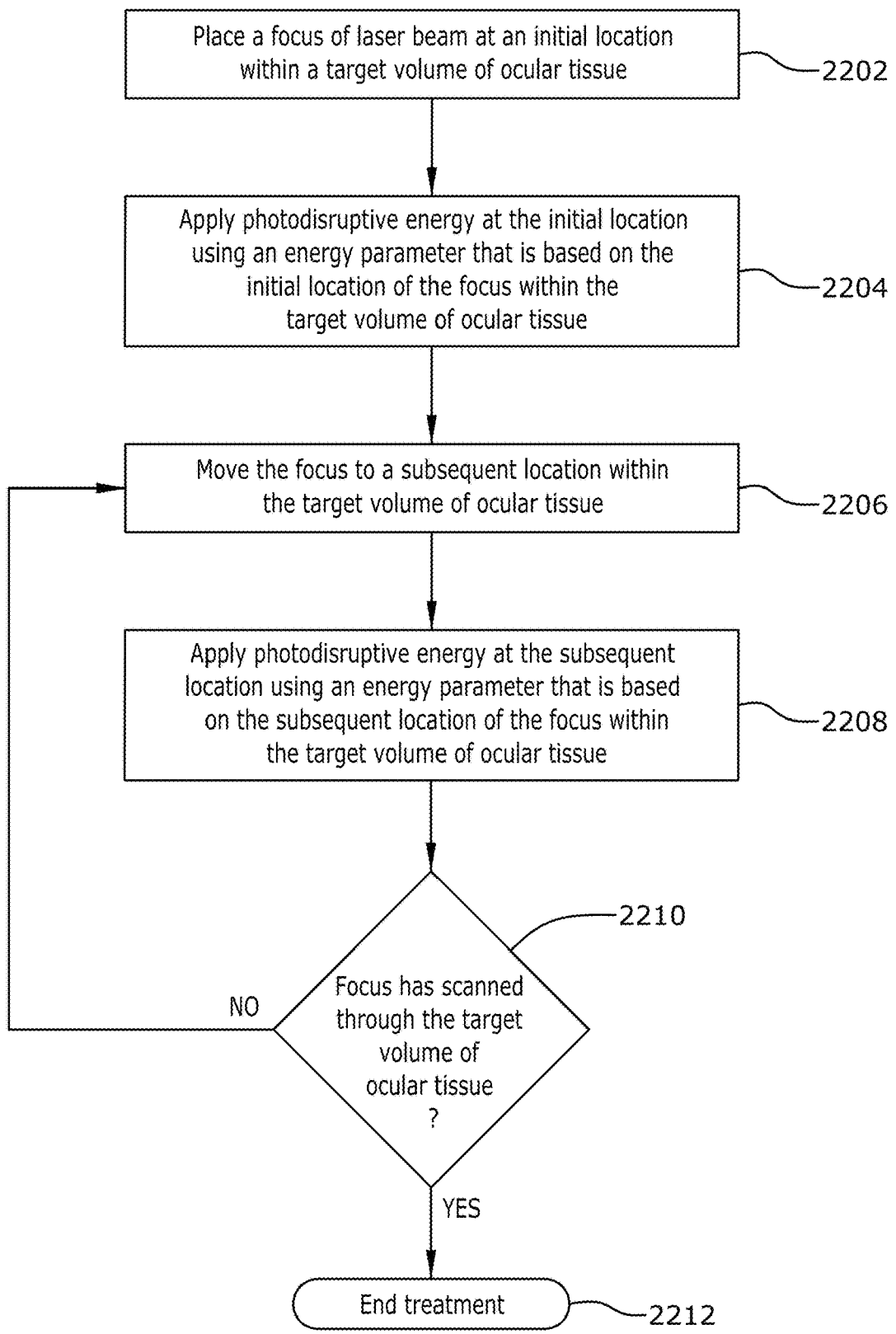
FIG. 22 is a flowchart of a method of photodisrupting a target volume of ocular tissue with a laser, wherein photodisruptive energy is based on the location of the focus within the target volume.

FIG. 22 is a flowchart of a method of photodisrupting a target volume of ocular tissue with a laser, wherein laser energy may vary as a function of the location of the target volume of ocular tissue, and the location of the laser focus within the target volume. The target volume of ocular tissue may be located in an irido-corneal angle of an eye of a patient, at a location along or around the circumference of the irido-corneal angle. The method begins at a point in a surgical procedure where access to the irido-corneal angle has already been obtained and one or more anatomical structures of the eye that are to be treated have been located. The target volume of ocular tissue may be entirely within ocular tissue. Alternatively, at least a portion of the target volume of ocular tissue may encompass portions of adjacent anatomy, e.g., the anterior chamber, or the interior of the Schlemm's canal.

Figure 23:
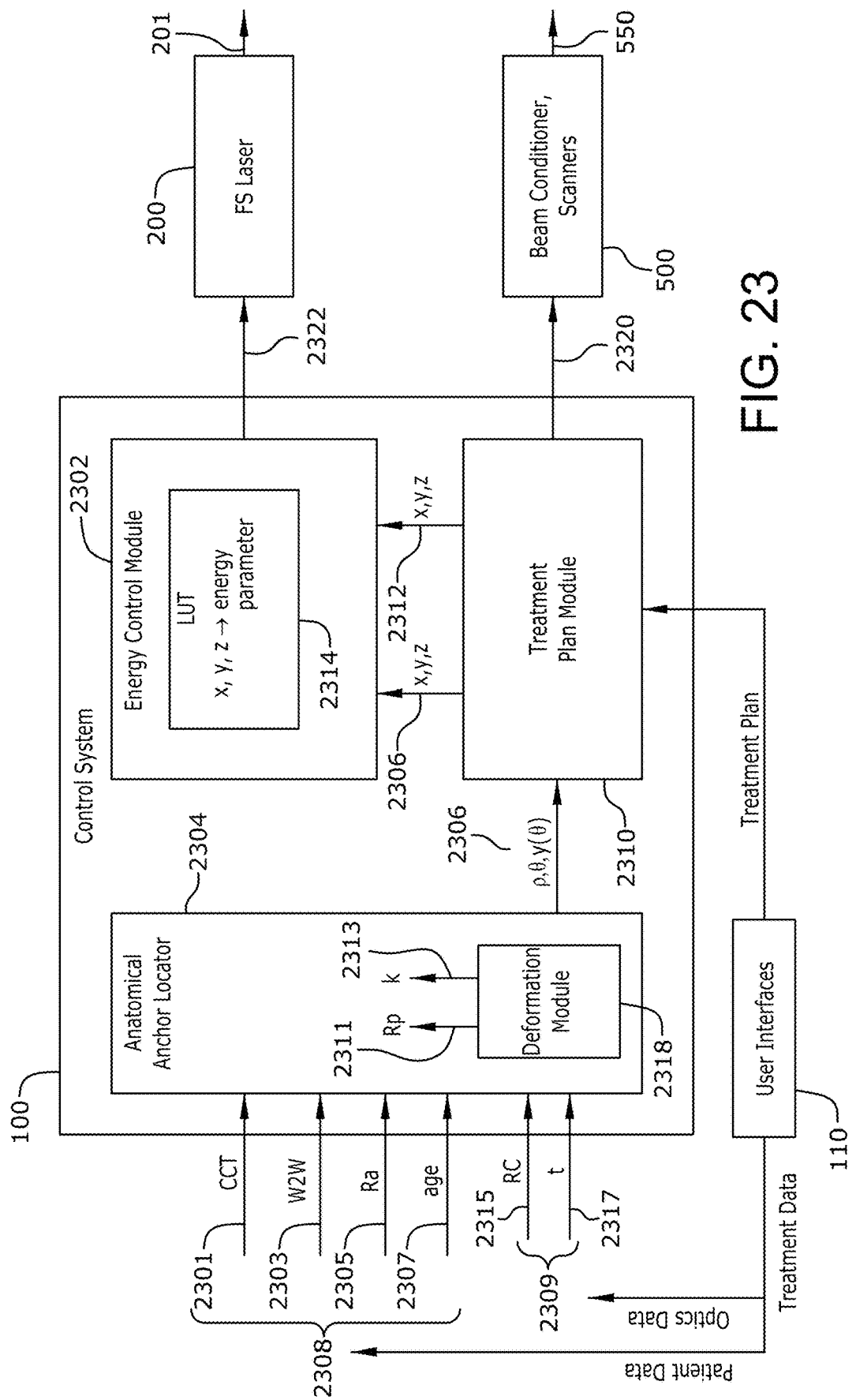
FIG. 23 is a block diagram of components of the integrated surgical system of FIG. 7 including a control system having an anatomical anchor locator, a treatment plan module, and an energy control module configured to implement the method of FIG. 22.

The method of FIG. 22 may be performed by the integrated surgical system 1000 of FIGS. 7-10b, having a control system 100 further configured as shown in FIG. 23. The control system 100 includes an anatomical anchor locator 2304, a treatment plan module 2310, and an energy control module 2302. The energy control module 2302 is configured to control the energy level of the laser during treatment. The energy control module 2302 may include, for example, a look up table 2324 that maps coordinate locations within a target volume of ocular tissue to one or more energy parameters. The anatomical anchor locator 2304 is configured to determine a coordinate set 2306 corresponding to the location of an anatomical anchor of the patient based on a set of patient data 2308 and a set of optics data 2309. This determined coordinate set 2306 is used to position the laser focus at an initial location within the target volume of ocular tissue. Once positioned at the initial location, further movement of the laser focus through the target volume of ocular tissue is controlled by the treatment plan module 2310, which defines a treatment pattern through which a laser focus is scanned in order to treat the target volume of ocular tissue. As further described below, the treatment pattern is defined by a plurality of coordinate sets 2306, 2312 that include the coordinate set 2306 corresponding to the location of an anatomical anchor.

Prior to initiation of the method of FIG. 22, patient data 2308, including natural biometric data and demographic data of the patient being treated, and optics data 2309, may be input to the control system 100 through a user interface 110, together with a treatment plan for the patient. As described above with reference to FIGS. 12a and 12b, a treatment plan may be defined by a treatment pattern P1 that defines the geometry of the target volume of ocular tissue to be treated, and placement parameters that define the location of the target volume of ocular tissue around the circumference of the irido-corneal angle.

Regarding the treatment pattern, with additional reference to FIG. 19, the treatment plan module 2310 may define a 3D treatment pattern P1 having a number of 2D treatment layers 1902 or treatment planes that are stacked to form a 3D treatment pattern characterized by a width w, height h, and depth or thickness t. Each individual treatment layer 1902 is in turn characterized by a pattern height h (equal to the height h of the 3D treatment pattern P1) and a pattern width w (equal to the width w of the 3D treatment pattern P1) and comprises an array of spots 1904—each at a corresponding one of the plurality of coordinate sets 2306, 2312. Treatment patterns of various geometric shapes may be defined by the treatment plan module 2310. Examples of other treatment patterns are described in U.S. patent application Ser. No. 16/838,858, entitled Method, System, and Apparatus for Generating Three-Dimensional Treatment Patterns for Laser Surgery of Glaucoma.

Figure 24:
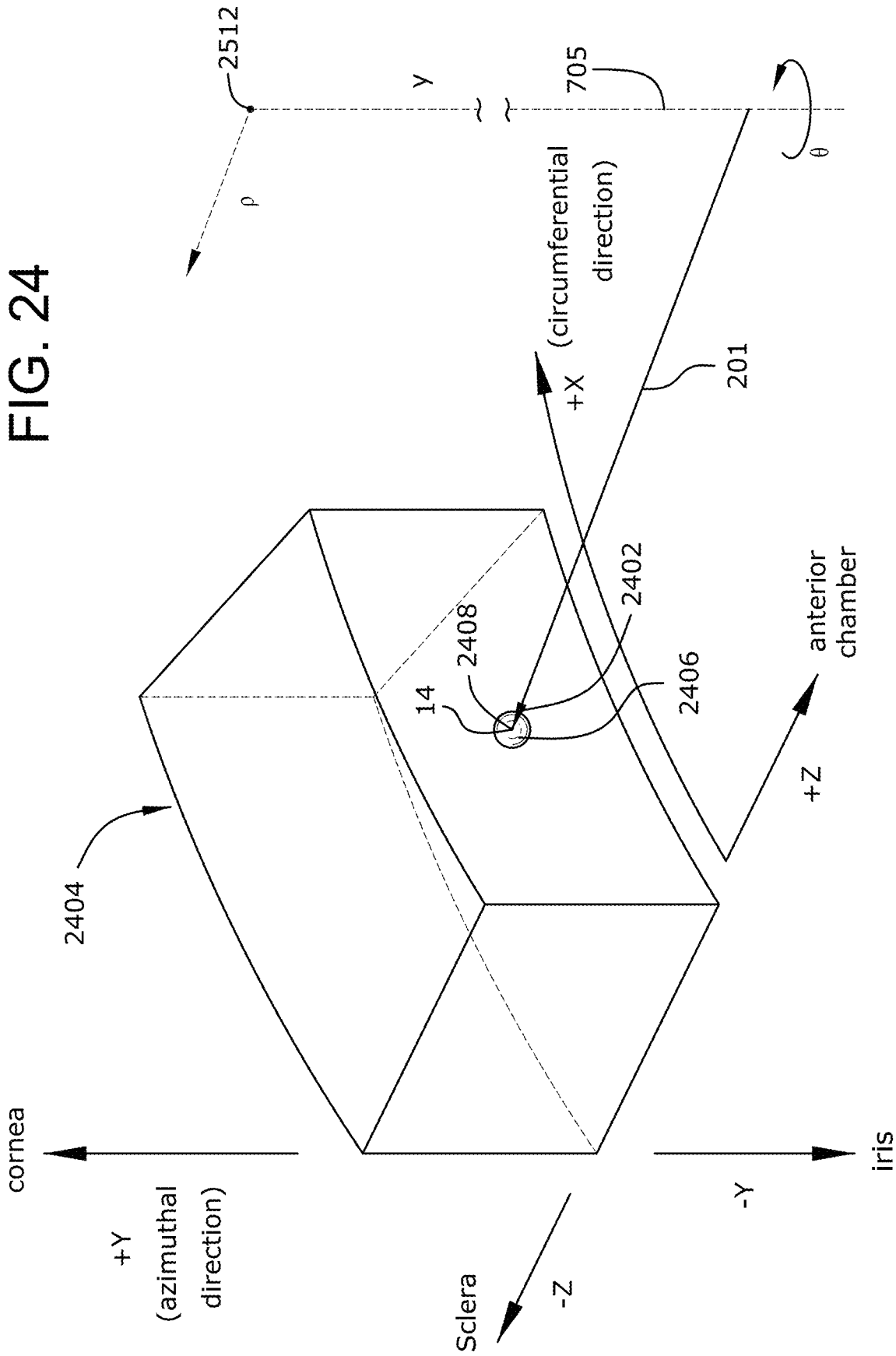
FIG. 24 is a schematic illustration of a clinical target volume of ocular tissue being scanned and treated by a laser.
Figure 25:
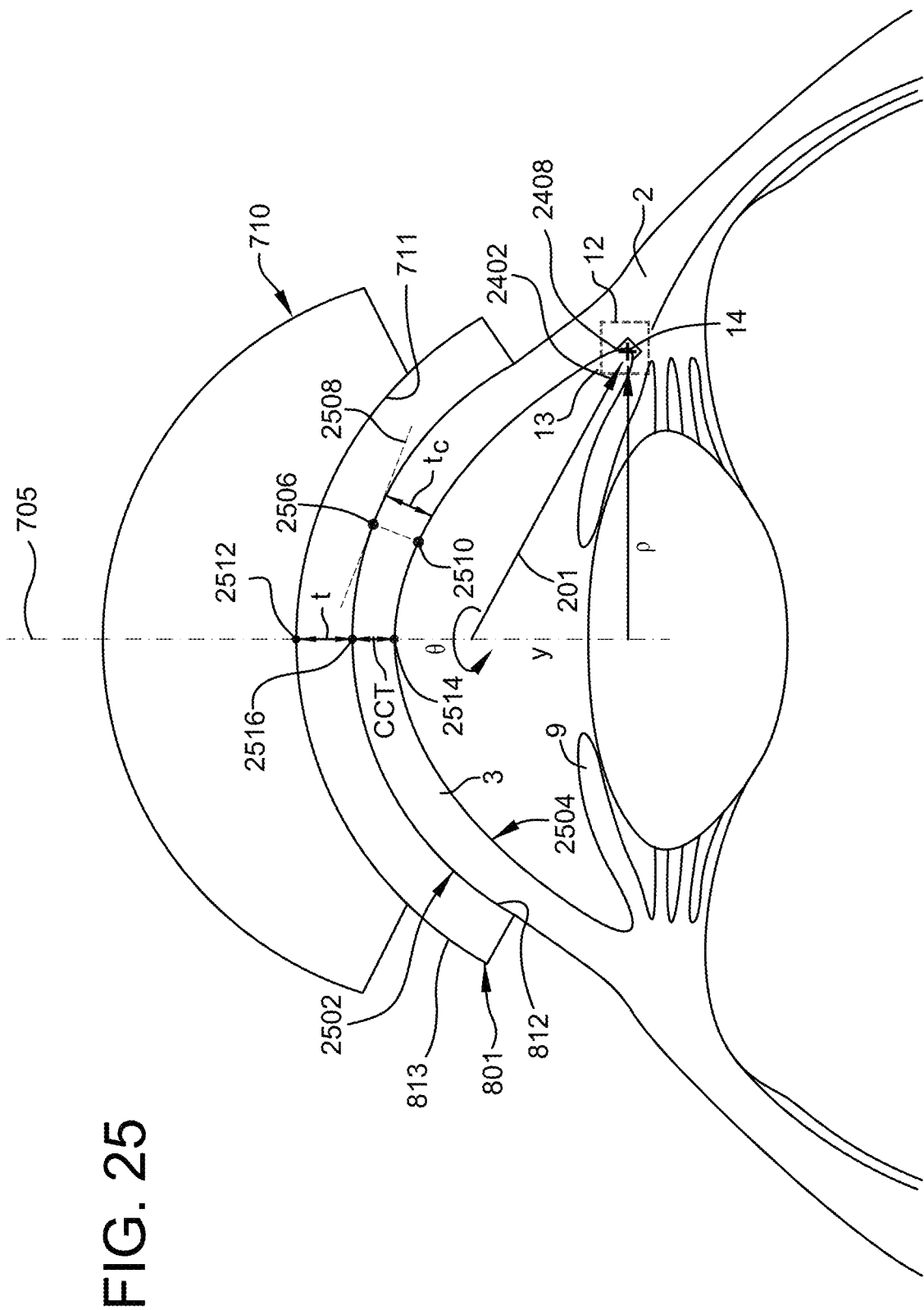
FIG. 25 is a cross-section of an eye during laser treatment having a window of a patient interface coupled to the cornea, and showing an anatomical anchor corresponding to a sclera spur located in a trabecular meshwork region.

Returning to FIG. 22, at block 2202, and with additional reference to FIGS. 23, 24, and 25, a focus 2402 of a laser 201 is placed at an initial location 2408 within the target volume of ocular tissue 2404 that is associated with an eye of a patient. To this end, the anatomical anchor locator 2304 of FIG. 23 derives a coordinate set 2306 corresponding to the initial location 2408 of the focus 2402 within the target volume of ocular tissue 2404 of FIG. 24. This initial coordinate set 2306 may be expressed, for example in cylindrical coordinates (ρ, θ, y(θ)), and is derived based on patient data 2308, including natural biometric data and demographic data of the patient being treated, and optics data 2309. Once the coordinate set 2306 for the initial location of the focus 2402 is derived, the focus is placed at that coordinate location.

With reference to FIG. 24, in some embodiments the initial location 2408 of the focus 2402 within the target volume of ocular tissue 2404 is at or near an anatomical anchor. In cases where the initial location of the focus 2402 is at an anatomical anchor, the derived initial coordinate set 2306 of FIG. 23 corresponds to the location coordinates of the anatomical anchor. With reference to FIG. 25, in some embodiments, the anatomical anchor may be the scleral spur 14, which is also the location of the base of the trabecular meshwork 12 as identified in histology, and morphologically corresponds to the transition point between transparent cornea 3 and denser, optically thick sclera 2.

With reference to FIGS. 23 and 24, the relevant patient data 2308 used to derive the coordinate set 2306 for an initial location 2408 corresponding to anatomical anchor 14 includes the patient's set of natural anatomical measurements, e.g., CCT 2301, W2W 2303, and Ra 2305, corresponding to the corneal meridian with which the laser beam 201 of the integrated surgical system 1000 is aligned, and the patient's demographic data, e.g., age 2307. The relevant optics data 2309 used to derive the coordinate set 2306 for an initial location 2408 includes the radius of curvature RC 2315 of a concave surface of an optical component, and a thickness t 2317 of the optical component that is or will be coupled to the patient's eye during treatment.

Regarding the patient's set of natural anatomical measurements, considering FIG. 21, if the laser beam 201 is aligned along the nasal-temporal meridian 2124 for delivery in the 3 o'clock direction (or the 9 o'clock direction), the patient's relevant set of natural measurements CCT 2301, W2W 2303, and Ra 2305 include: the central corneal thickness (CCT) 2102, the nasal-temporal W2W (W2W$_{nt}$) 2104, and the nasal-temporal anterior cornea radius of curvature (Ra$_{nt}$) 2112. If, however, the laser beam 201 is aligned along the superior-inferior meridian 2126 for delivery in the 6 o'clock direction (or the 12 o'clock direction), the patient's relevant set of natural measurements CCT 2301, W2W 2303, and Ra 2305 include: the central corneal thickness (CCT) 2102, the superior-inferior W2W (W2W$_{si}$) 2106, and the superior-inferior anterior cornea radius of curvature (Ra$_{si}$) 2114. Again, the relevant patient data 2308 used to derive the coordinate set 2306 may be for any corneal meridian.

Regarding the optics data 2309, e.g., the radius of curvature RC 2315 and thickness t 2317 of optical component, with reference to FIGS. 9a, and 25, during a laser treatment procedure an optical component in the form of a window 801 of a patient interface 800 is docked between the cornea 3 and an exit lens 710 of a focusing objective head 700 (see FIG. 9a) of the integrated surgical system 1000. As shown in FIG. 25, a concave surface 812 of the window 801 of the patient interface contacts the anterior surface 2502 of the cornea 3, and a convex surface 813 contacts a surface 711 of the exit lens 710 of the focusing objective head. This applanation of the window 801 to the eye deforms the anterior surface 2502 of the cornea 3, which in turn deforms the posterior surface 2504 of the cornea. As described later below, the anatomical anchor locator 2304 accounts for deformation of the anterior surface 2502 and the posterior surface 2504 of the cornea 3 due to applanation during a treatment procedure based on the optics data 2309, e.g., the radius of curvature RC 2315 of the concave surface of the window 801.

Having the relevant patient data 2308 for the relevant meridian of the eye and the optics data 2309 (collectively referred to herein as treatment data), the anatomical anchor locator 2304 derives a coordinate set 2306 for an initial location 2408 corresponding to an anatomical anchor 14 of the patient. To this end, and with reference to FIG. 25:

1) The anatomical anchor locator 2714 generates a natural anterior curve based on patient data 2308, including the W2W, k, and the natural anterior radius of curvature Ra. This is done using the following equation:

$$y(\theta) = -\frac{c\rho^2}{1 + \sqrt{1 - (1+k)c^2\rho^2}} + CCT + t \quad \text{(Eq. 3)}$$

where:
θ is the rotational angle corresponding to the relevant meridian of the eye;
y is sag, the distance from an origin 2512 along the y axis, where the origin is at the apex of the window 801;
c is the curvature (the inverse of the natural anterior radius of curvature Ra 2305);
k is the natural conic constant (derived from the patient's age 2307 using Eq. 2);
ρ is the radius, the distance from the origin 2512 along the ρ axis;
CCT is the central corneal thickness 2301; and is constant; and
t is the thickness of the window 801; and is constant.

Note that the rotational angle θ may be the position of the turret about the y axis 705 or "sweep angle" (as shown in FIGS. 24 and 25) and is defined for θ=0 at the superior position (12 o'clock) for either the left or the right eye and to be positive clockwise when looking from the top of the eye. For example, with reference to FIG. 21, θ=90 for the left eye is nasal, θ=180 is inferior and θ=270 is temporal. For the right eye (not shown in FIG. 21), θ=90 is temporal, θ=180 is inferior and θ=270 is nasal.

Note that in Eq. 1 (and all other equations for y herein) y(θ) has a negative sign because the origin 2512 (see FIG. 25) of the cylindrical coordinate system is above the anterior surface 2502 of the cornea 3 and the cornea bends downward, toward the iris 9.

Because each of t and CCT is a constant for a particular patient, the last two terms in Eq. 3 represent a fixed offset which is the distance from the origin 2512 to the apex 2514 of the posterior surface 2504 of the cornea 3.

The natural c (the inverse of the natural anterior radius of curvature Ra 2305) and the natural conic constant k are substituted in Eq. 3, and a number of different radius positions from the origin out to one-half the natural W2W 2303 are individually substituted for ρ to obtain a corresponding number of values of y. In one example, the number of radius positions is 500. The values of y as a function of ρ define a curve corresponding to the natural anterior curve.

While the natural anterior curve is not shown in FIG. 25 due to applanation of the window 801 to the cornea 3, the natural anterior curve would be the curve of the anterior surface 2502 of the cornea if the window was not coupled to the cornea.

2) The anatomical anchor locator 2714 then generates a natural posterior curve based on the patient data 2308, including the W2W, k, CCT, and the natural anterior radius of curvature Ra. This is done using the following equation:

$$y(\theta) = -\frac{c\rho^2}{1 + \sqrt{1 - (1+k)c^2\rho^2}} + CCT + t \qquad (\text{Eq. 4})$$

where:
θ is the rotational angle corresponding to the relevant meridian of the eye;
y is sag, the distance from the origin 2512 along the y axis;
c is the curvature (the inverse of the natural posterior radius of curvature Rp, where Rp=Ra/1.22);
k is the natural conic constant (derived from the patient's age 2307 using Eq. 2);
ρ is the radius, the distance from the origin 2512 along the ρ axis; and
CCT is the central corneal thickness 2301; and
t is the thickness of the window 801.

The natural c (the inverse of the natural posterior radius of curvature Rp), the natural conic constant k, and the natural CCT are substituted in Eq. 4, and a number of different radius positions from the origin out to one-half the natural W2W 2303 are individually substituted for ρ to obtain a corresponding number of values of y. The values of r substituted into the equation may corresponds to the same values of ρ substituted in Eq. 3 when generating the natural anterior curve. In one example, the number of radius positions is 500. The values of y as a function of ρ define a curve corresponding to the natural posterior curve. While the natural posterior curve is not shown in FIG. 25 due to applanation of the window 801 to the cornea 3, the natural posterior curve would be the curve of the posterior surface 2504 of the cornea if the window was not coupled to the cornea.

3) The anatomical anchor locator 2304 then generates a deformed anterior curve based on the patient data 2308, including the conic constant k and the W2W, and optics data 2309, including the radius of curvature of the window 801 coupled to the anterior surface 2502 of the cornea 3. This is done using the following equation:

$$y(\theta) = -\frac{c\rho^2}{1 + \sqrt{1 - (1+k)c^2\rho^2}} + CCT + t \qquad (\text{Eq. 5})$$

where:
θ is the rotational angle corresponding to the relevant meridian of the eye;
y is sag, the distance from the origin 2512 along the y axis;
c is the curvature (the inverse of the radius of curvature 2315 of the window 801);
k is the natural conic constant (derived from the patient's age using Eq. 2); and
ρ is the radius, the distance from the origin 2512 along the ρ axis;
CCT is the central corneal thickness 2301; and
t is the thickness of the window 801.

The value of c (the inverse of the radius of curvature of the window 801), and the natural conic constant k are substituted in Eq. 5, and a number of different radius positions from the origin out to one-half the natural W2W 2303 are individually substituted for ρ to obtain a corresponding number of values of y. The values of ρ substituted into the equation may corresponds to the same values of ρ substituted in Eq. 3 when generating the natural anterior curve. In one example, the number of radius positions is 500. The values of y as a function of r define a curve corresponding to the deformed anterior curve 2502.

4) The anatomical anchor locator 2304 then calculates the arc length of the deformed anterior curve 2502 and the arc length of the deformed posterior curve 2504 using known equations, wherein the arc length corresponds to the distance along the respective curve between the minimum radius (origin) and the maximum radius (W2W/2).

5) The anatomical anchor locator 2304 then determines a deformed posterior curve using the boundary conditions that the posterior corneal arc length is constant (does not change after deformation). In other words, the natural posterior arc length is equal to the deformed posterior art length. With reference to FIG. 25, arc length refers to the distance between two points on a curve. Thus, a full corneal arc length of a corneal cross-section (as shown in FIG. 25) is the distance along the arc from one end of the cornea 3 to the other end. While a half corneal arc length refers to the distance along the arc from one end of the cornea 3 to the point on the curve at the azimuthal axis 705.

Continuing with reference to FIGS. 23 and 25, the deformation module 2318 of the anatomical anchor locator 2304 calculates a corresponding posterior surface point 2510 for each of a discrete number of anterior surface points 2506 along the deformed anterior surface 2502 arc length. Based on the previously derived natural anterior curve and natural posterior curve, the deformation module 2318 determines a normal thickness ($t_c$) of the cornea 3 at various points along the length of the natural cornea. Because the thickness of the cornea 3 is not impacted by applanation of the window 801, the deformation module 2318 applies these known normal thicknesses to determine a corresponding posterior surface point 2510 for each of a number of anterior surface points. Each corresponding posterior surface point 2510 is in a direction normal to an anterior tangent 2508 through its corresponding anterior surface point 2506 and is a distance equal to the normal thickness ($t_c$) at that point from the corresponding anterior surface point 2506. The number of discrete anterior surface points 2506 may correspond to the number of radius positions used to generate the deformed anterior curve. The number of discrete posterior surface points 2510 define a deformed posterior curve 2504.

6) The deformation module 2318 of the anatomical anchor locator 2304 then fits a deformed posterior fitted curve (not shown in FIG. 25) to the deformed posterior curve 2504 by fitting to the following equation using non-linear least squares to numerically calculate a deformed posterior conic constant k and deformed posterior base radius of curvature Rp:

$$y(\theta) = -\frac{c\rho^2}{1 + \sqrt{1 - (1+k)c^2\rho^2}} + CCT + t \qquad (\text{Eq. 6})$$

where:
- θ is the rotational angle corresponding to the relevant meridian of the eye;
- y is sag (as shown in FIG. 25), the distance from the origin 2512 along the y axis;
- c is the curvature (the inverse of the deformed posterior base radius of curvature);
- k is the deformed conic constant; and
- ρ is the radius, the distance from the origin 2512 along the ρ axis;
- CCT is the central corneal thickness 2301; and
- t is the thickness of the window 801.

In the fitting process, various values for c and k are arbitrarily selected and values of y are determined, until the values for y from the origin along the ρ axis define a deformed posterior fitted curve that closely fits to the deformed posterior curve 2504. The values for c and k that produce the deformed posterior fitted curve define the deformed posterior base radius of curvature Rp 2311 and the deformed conic constant k 2313 for the patient.

Having now determined a deformed posterior base radius of curvature Rp 2311 and a deformed conic constant k 2313 for the patient being treated, based on the relevant patient data 2308 and optics data 2309, the initial coordinate set 2306 may be determined based on a coordinate system. For example, using a cylindrical coordinate system with the origin 2512 defined at the apex of the window 801 of the patient interface—a fixed location associated with optics of the surgical system that is invariant of patient anatomy—then the cylindrical coordinates (ρ, θ, y(θ)) of the location of the scleral spur 14 of the eye coupled to the window 801, and hence the initial location 2408 of the focus 2402 of FIG. 24 is obtained by inserting values for ρ, Rp, k, CCT, and t in the following equation to solve for y(θ):

$$y(\theta) = -\frac{c\rho^2}{1 + \sqrt{1 - (1+k)c^2\rho^2}} + CCT + t \quad \text{(Eq. 7)}$$

where:
- θ is the rotational angle corresponding to the relevant meridian of the eye;
- y is the distance from the origin 2512 along the azimuthal axis 705;
- ρ is the radial distance from the origin 2512 along the ρ axis and is set equal to one-half of W2W;
- c is the inverse of Rp, which is the deformed posterior base radius of curvature 2311;
- k is the deformed conic constant 2313; W2W is the white-to-white diameter 2303 along the relevant meridian of the eye;
- CCT is the central corneal thickness 2301; and
- t is the thickness of the window 801.

The first term in Eq. 7 represents the azimuthal distance, or "sag", of a conic posterior corneal surface as a function of the radial coordinate, ρ, and sweep angle, θ. As noted above, in the first term in Eq. 7, Rp is the base posterior radius of curvature and k is the deformed conic constant, each of which are calculated by the deformation module 2318 of FIG. 23. As the eye is non-rotationally symmetric, then Rp is a function of θ. For example, from the above definitions, if θ=90 (nasal for left eye and temporal for the right eye) then Rp=$Rp_{nt}$ as this would correspond to the nasal-temporal axis. Alternatively, if θ=180 (inferior location for both eyes) then Rp=$Rp_{si}$. With reference to FIG. 25, the radial coordinate, ρ, is 0 along the azimuthal axis 705 (through the center of the eye) and reaches its maximum value at the scleral spur 14 location, or half the white-to-white diameter (W2W).

Further regarding the base posterior radius of curvature Rp, the surface profile or "sag" of a conical section is mathematically described in Eq. 7, which has a radius of curvature Rp and a conic constant k. If the conical section was purely spherical then k=0 and the base radius of curvature=true radius of curvature. The base radius of curvature Rp is essentially the radius of curvature obtained when a spherical surface fit is applied to the conical surface. However, since the corneal surface is not purely spherical then the true surface deviates from this fitted spherical surface. The deformed conic constant k provides an additional descriptive variable and allows recovery of the true surface.

Returning to block 2202 of FIG. 22, and with additional reference to FIGS. 23 and 24, having determined the cylindrical coordinates (ρ, θ, y(θ)) corresponding to the initial coordinate set 2306, the laser focus 2402 is placed at an initial location 2408 in the volume of ocular tissue 2404. To this end, the treatment plan module 2310 is configured to output a control signal 2320 to control beam conditioners, scanners 500 of the integrated surgical system 1000 that causes the beam conditioners, scanners to position the focus 2402 based on the initial coordinate set 2306.

It is noted that the initial coordinate set 2306 is defined by a local coordinate system associated with the energy control module 2302. Within the local coordinate system, the initial coordinate set 2306 may be determined based on one coordinate system while the coordinate entries in the LUT 2314 are based on a different coordinate system. For example, in the above description, the initial coordinate set 2306 determined by the anatomical anchor locator 2304 is based on a cylindrical coordinate system, and the coordinate entries in the LUT 2314 are based on a Cartesian coordinate system. To account for this, the treatment plan module 2310 may be configured to transform the initial coordinate set 2306 received from the anatomical anchor locator 2304 to a coordinate system that matches the LUT of the energy control module 2302.

At block 2204 of FIG. 22, and with additional reference to FIGS. 23 and 24, having placed the focus 2402 at the initial location 2408, photodisruptive energy is applied by the laser 201 at the initial location in accordance with an energy parameter that is based on the initial location 2306 of the focus within the target volume of ocular tissue 2404. To this end, the energy control module 2302 is configured to output an energy control signal 2322 to the FS laser source 200 that informs the laser source of the initial energy parameter to be used when applying photodisruptive energy at the initial location 2408. In some embodiments, the energy control module 2302 includes a database or look up table (LUT) 2314 that maps coordinate locations to one or more energy parameters. The energy control module 2302 is configured to locate the LUT entry that matches the initial coordinate set 2306 and to locate the energy parameter mapped to that entry. The energy parameter found in the look up table corresponds to an energy level (p J) sufficient to disrupt the tissue at the location of the focus 2402. In other words, the energy level (p J) is sufficient to disrupt the tissue within a volume corresponding in size to the focus spot size 2406 at the location of the focus 2402.

At block 2206 of FIG. 22, and with additional reference to FIGS. 23 and 24, the focus 2402 of the laser 201 is moved to a subsequent location within the target volume of ocular tissue 2404. To this end, a subsequent coordinate set 2312 corresponding to the subsequent location of the focus 2402 within the target volume of ocular tissue 2404 may be derived based on the initial coordinate set 2306. For example, with reference to FIG. 20, the subsequent coordinate set 2312 may be a spot separation 2002 away from the initial coordinate set 2306 in one or both of the x or y direction. The subsequent coordinate set 2312 may be defined by a treatment pattern programmed into the treatment plan module 2310, and movement of the laser 201 to the subsequent location is enabled by control signals 2320 configured to control beam conditioners, scanners 500 of the integrated surgical system 1000 to position the laser focus 2402 based on the subsequent coordinate set 2312.

It is noted that the scanning of the laser during treatment may be based on a local coordinate system relative to the treatment pattern P1 through which the laser is being scanned. For example, with reference to FIGS. 19 and 20, the treatment pattern P1 may be defined by a Cartesian coordinate system relative to the scanner of the integrated surgical system 1000. In some cases the origin of the local coordinate system of the energy control module 2302 may be different from the origin of the local coordinate system of the scanner of the integrated surgical system 1000. In such cases, when deriving the subsequent coordinate set 2312 based on the initial coordinate set 2306, the treatment plan module 2310 may perform origin and/or coordinate translations in order to express the subsequent coordinate set 2312 in terms of the coordinate system of LUT 2314.

At block 2208 of FIG. 22, and with additional reference to FIGS. 23 and 24, after the focus 2402 is moved to the subsequent location corresponding to the subsequent coordinate set 2312, photodisruptive energy is applied by the laser 201 at the subsequent location in accordance with an energy parameter that is based on the subsequent location of the focus within the target volume of ocular tissue 2404. The energy parameter for the subsequent coordinate set 2312 may be determined from the look up table 2314 of the energy control module 2302.

In some embodiments the energy parameter is determined on a location-by-location basis. In other words, for each different coordinate set 2306, 2312 included in a treatment pattern, the look up table of the energy control module 2302 is used to determine the energy parameter for that location and provide dynamic adjustment of the energy of the laser as the focus 2402 is scanned through the treatment pattern within the target volume of ocular tissue 2404. With reference to FIGS. 19 and 20, Table 4 is an example look up table 2314 that provides a corresponding energy level for spot 1904 locations in an XY scan plane 1902 at a fixed depth z1 of a treatment pattern. As described below in the Look Up Table Generation section of this disclosure, the energy level assigned to a coordinate (x,y,z) is based on an estimated laser spot size at that coordinate location. Accordingly, for purposes of explanation estimated spot size information is included in the example lookup table 2314 shown in Table 4. The actual look up table 2314 resident in the control system 100 may or may not include this estimated spot size information. In Table 4 the number after x corresponds to the column position (e.g., 1-8, from left to right in FIG. 20), the number after y corresponds to row position (e.g., 1-5, from bottom to top in FIG. 20), and the number after z corresponds to the depth or layer position (e.g., 1-6, from front to back in FIG. 19).

TABLE 4

| Coordinates (x, y, z) | Estimated Laser Spot Size (μm) | Energy (μJ) |
|---|---|---|
| x1, y1, z1 | 5 | 0.6 |
| x2, y1, z1 | 5 | 0.6 |
| . | . | . |
| . | . | . |
| . | . | . |
| x7, y1, z1 | 5 | 0.6 |
| x8, y1, z1 | 5 | 0.6 |
| x1, y2, z1 | 5 | 0.6 |
| x2, y2, z1 | 5 | 0.6 |
| . | . | . |
| . | . | . |
| . | . | . |
| x7, y2, z1 | 5 | 0.6 |
| x8, y2, z1 | 5 | 0.6 |
| x1, y3, z1 | 10 | 2.4 |
| x2, y3, z1 | 10 | 2.4 |
| . | . | . |
| . | . | . |
| . | . | . |
| x7, y4, z1 | 10 | 2.4 |
| x8, y4, z1 | 10 | 2.4 |
| x1, y5, z1 | 15 | 5.3 |
| x2, y5, z1 | 15 | 5.3 |
| . | . | . |
| . | . | . |
| x7, y5, z1 | 15 | 5.3 |
| x8, y5, z1 | 15 | 5.3 |
| x1, y1, z2 | 5 | 0.6 |
| x2, y1, z2 | 5 | 0.6 |
| . | . | . |
| . | . | . |
| . | . | . |

In some embodiments the energy parameter corresponds to a measure of photodisruptive energy across a plurality of different locations of the focus 2402. For example, the measure of photodisruptive energy may correspond to a minimum energy level that ensures photodisruption at each of a plurality of different locations of the focus 2402 within the volume of ocular tissue 2404. In other words, the energy level delivered while treating a particular volume of ocular tissue 2404 is kept constant and at a level that assures photodisruption occurs at each location 2408, as specified by the coordinate sets 2306, 2312 included in a treatment pattern, through which the focus 4202 is scanned.

In some embodiments the energy parameter is based on the estimated spot size 2406 of the laser focus 2402 at each location 2408, as specified by the coordinate sets 2306, 2312 through which the focus 4202 is scanned, and is an energy level that maintains a constant fluence. For example, Table 5 shows laser energy as a function of estimated spot size 2406 to maintain a constant 1 $J/cm^2$ fluence.

TABLE 5

| Spot Diameter (μm) | Spot Surface Area ($cm^2$) | Energy (μJ) |
|---|---|---|
| 5 | $1.96 \times 10^{-07}$ | 0.6 |
| 10 | $7.85 \times 10^{-07}$ | 2.4 |
| 15 | $1.77 \times 10^{-06}$ | 5.3 |
| 20 | $3.14 \times 10^{-06}$ | 9.4 |

A larger fluence level can be selected to assure photodisruption always occurs i.e., Table 5 could be re-computed using 1.5 $J/cm^2$.

Returning to FIG. 22, and with additional reference to FIGS. 23 and 24, at block 2210, if the focus 2402 of the laser 201 has scanned through the target volume of ocular tissue 2404 the process proceeds to block 2212 where the laser treatment of the volume of ocular tissue ends. If the focus 2402 of the laser 201 has not scanned through the target volume of ocular tissue 2404 the process repeatedly cycles through blocks 2206 and 2208 until the focus of the laser has scanned through the target volume of ocular tissue. For example, with reference to FIGS. 19 and 24, the focus 2402 may be scanned in multiple directions relative to the target volume of ocular tissue 2404 through an XY treatment plane 1902, and then moved in the z direction and scanned through another XY treatment plane, to thereby photodisrupt one or more layers of tissue of the target volume of ocular tissue. This is repeated until the focus 2402 has scanned through the entirety of the treatment pattern P1 and thus through the target volume of ocular tissue 2404.

At block 2212 of FIG. 22, and with additional reference to FIGS. 23 and 24, if treatment of the volume of ocular tissue 2404 is complete, the entire method of FIG. 22 may then be repeated for one or more different alignments of the laser beam to treat different target volumes of ocular tissue. To this end, the turret of the surgical system 1000 may be rotated to align the laser beam 201 along a different meridian of the cornea for delivery in a different clock time direction. With reference to FIG. 21, in some embodiments the turret is configured to rotate in 3° increments, and there are ten increments 2130 between adjacent clock hours. For example, the turret may be rotated five increments to align the laser beam 201 along a subsequent meridian 2128. In this case, the patient's central corneal thickness (CCT) 2102, W2W diameter along the subsequent meridian 2128, and posterior cornea radius of curvature Rp along the subsequent meridian, which is derived from the patient's anterior cornea radius of curvature Ra along the same meridian, are the relevant patient data 2308 that is used at block 2202 of FIG. 22 to determine the initial coordinate set 2306 of FIG. 23 for the location of the anatomical anchor within the target volume of ocular tissue 2404 that is aligned with the different clock time direction. Note that the optics data 2309, which is fixed by the optical component, is the same regardless of the meridian. This process may be repeated numerous times to treat a number of different volumes of ocular tissue around the circumference of irido-corneal angle.

Having thus described a method of laser treatment based on a patient's biometric data and a look up table that maps laser focus locations to energy parameters, a description of a method and system for generating such a look up table follows.

Look Up Table Generation

With reference to FIG. 25, in accordance with embodiments disclosed herein a look up table is derived based on a clinical model that recognizes that, for a particular angle θ (i.e., the rotational angle position of the turret about the y axis 705 or "sweep angle"), each patient in a patient population has a unique location of an anatomical anchor, which location is determined by the patient's anatomy. In the example clinical model disclosed herein, the scleral spur is the anatomical anchor 14 as it serves as a clinically identifiable landmark, via either a gonioscope or OCT imaging. Furthermore, the scleral spur is associated with the trabecular meshwork 12 in the irido-corneal angle 13, which encompass the volumes of ocular tissue that are targeted for laser treatment in accordance with the treatment methods described herein.

The clinical model also recognizes that during treatment the optical pathway to a location of an anatomical anchor may be affected by optics of the system. For example, optical variables and mechanical variables of optics, e.g., lenses, windows, etc., can lead to optical aberrations. The clinical model disclosed herein accounts for these aberrations.

The clinical model also recognizes that each patient-unique location of the anatomical anchor 14 may be expressed relative to a patient-invariant location 2516. In the example clinical model disclosed herein, the anterior corneal apex is the patient-invariant location 2516. Regarding the patient-invariant location and with reference to FIG. 25, during a laser treatment procedure a concave surface 812 of a window 801 of the patient interface contacts the anterior surface 2502 of the cornea 3, and a convex surface 813 contacts a surface 711 of an exit lens 710 of the focusing objective head. The window 801 of the patient interface 800 is a fixed optic of the integrated surgical system 1000 and provides a fixed optic location, e.g., the apex 2512 of the window 801, determined by very tight mechanical tolerances. Therefore, the choice of the anterior cornea apex 2516 as a fixed, patient-invariant location is appropriate since the position of the anterior cornea apex relative to a fixed laser beam is very tightly controlled by the fixed window 801.

Still referring to FIG. 25, the clinical model further recognizes that, due to docking of the window 801 of the patient interface to the anterior surface 2502 of the cornea during a laser treatment procedure, the posterior surface and the anterior surface of the cornea respectively deform into a deformed posterior surface 2504, and a deformed anterior surface. Because the scleral spur, i.e., the anatomical anchor 14, is where the posterior surface 2504 of the cornea 3 ends, it follows that the scleral spur location also changes due to the docking of the window 801 to the anterior surface 2502. The clinical model disclosed herein accounts for this deformation.

Figure 26:
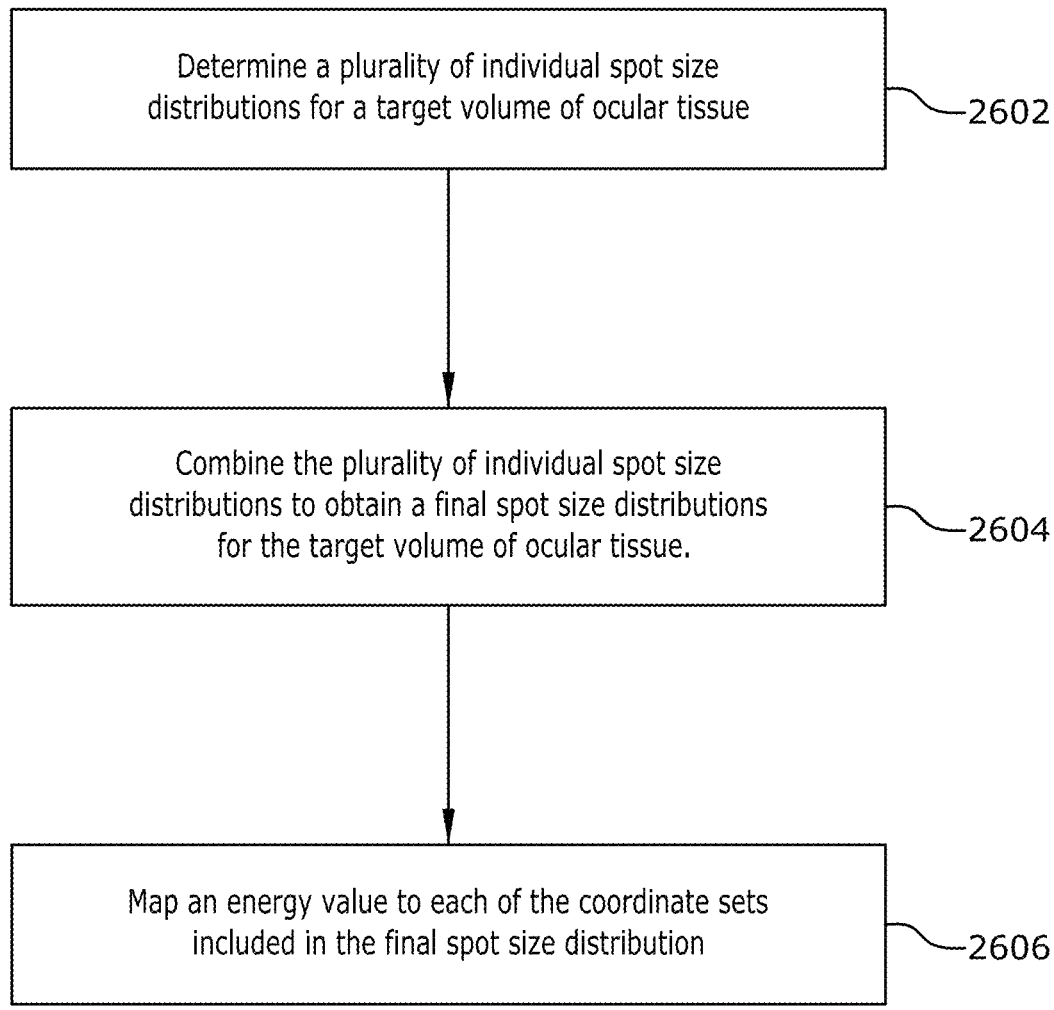
FIG. 26 is a flowchart of a method of generating a look-up table for use in determining an energy parameter for photodisrupting ocular tissue with a laser.

FIG. 26 is a flowchart of a method of generating a look-up table for use by a surgical system to determine an energy parameter for photodisrupting ocular tissue with a laser. The look up table maps or assigns one or more energy parameters to a number of coordinate sets. Each of these coordinate sets represents a location within a target volume of the ocular tissue at which a focus of the laser may be placed during treatment by the surgical system. After being generated, the look up table may be used as the look up table 2314 in the energy control module 2302 of the control system 100 in FIG. 23.

The method of FIG. 26, which is described in detail below, may be implemented by a look up table generator 2702 shown in FIG. 27. In some embodiments, the look up table generator 2702 includes a clinical model simulator 2710, an optics model simulator 2720, an anatomical anchor locator 2714, and a ray tracing module 2730 that operate together to generate an individual spot size distribution 2722 for each of a plurality of different sets of simulated patient data 2712 and simulated optics data 2713. Each individual spot size distribution 2722 may be defined by a collection of coordinate sets 2706 and a laser spot size 2732 for each coordinate set in the collection.

Figure 27:
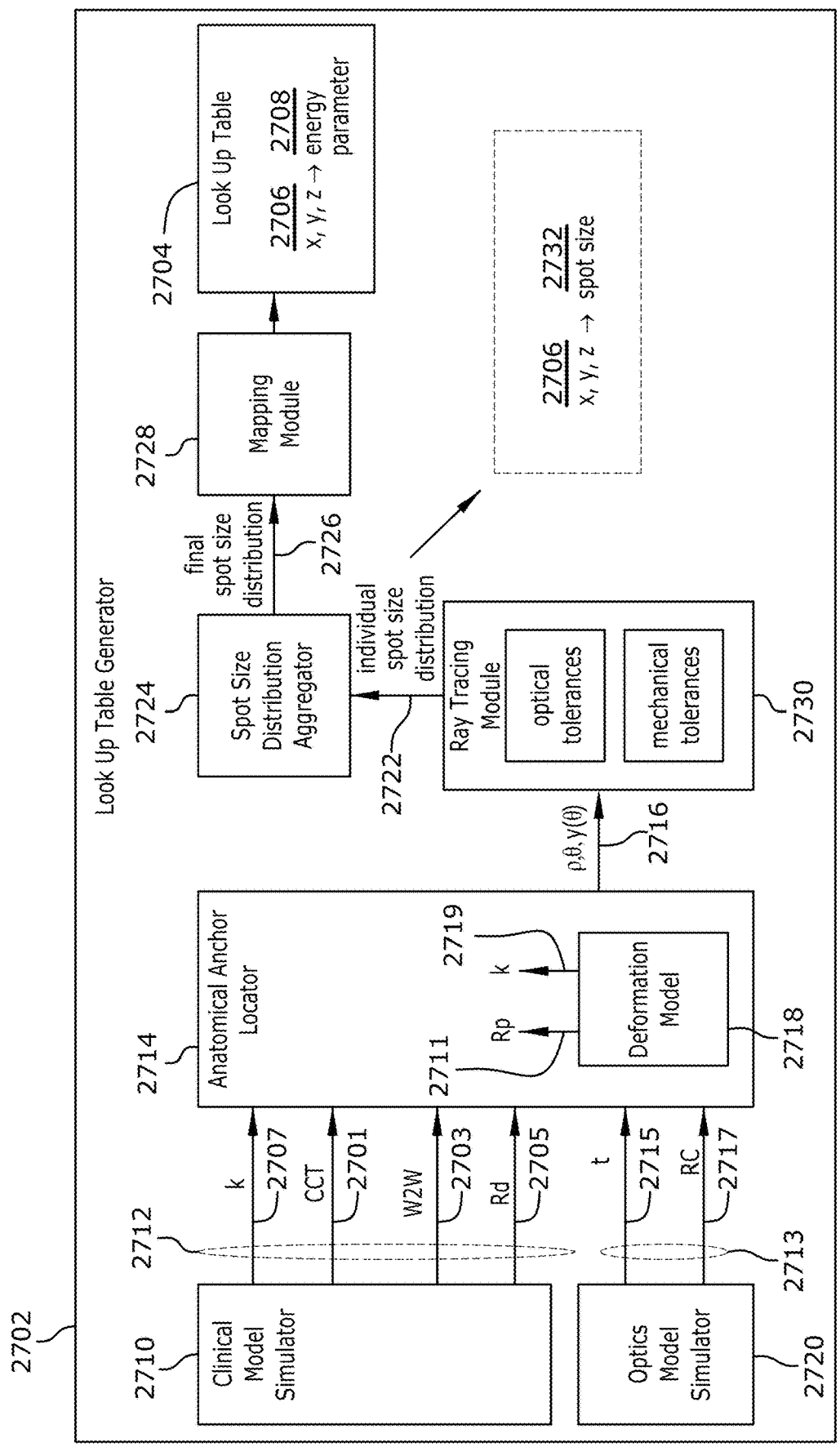
FIG. 27 is a block diagram of a look up table generator configured to generate a look up table based on simulated patient data, which may be included in the energy control module of FIG. 23.
Figure 28:
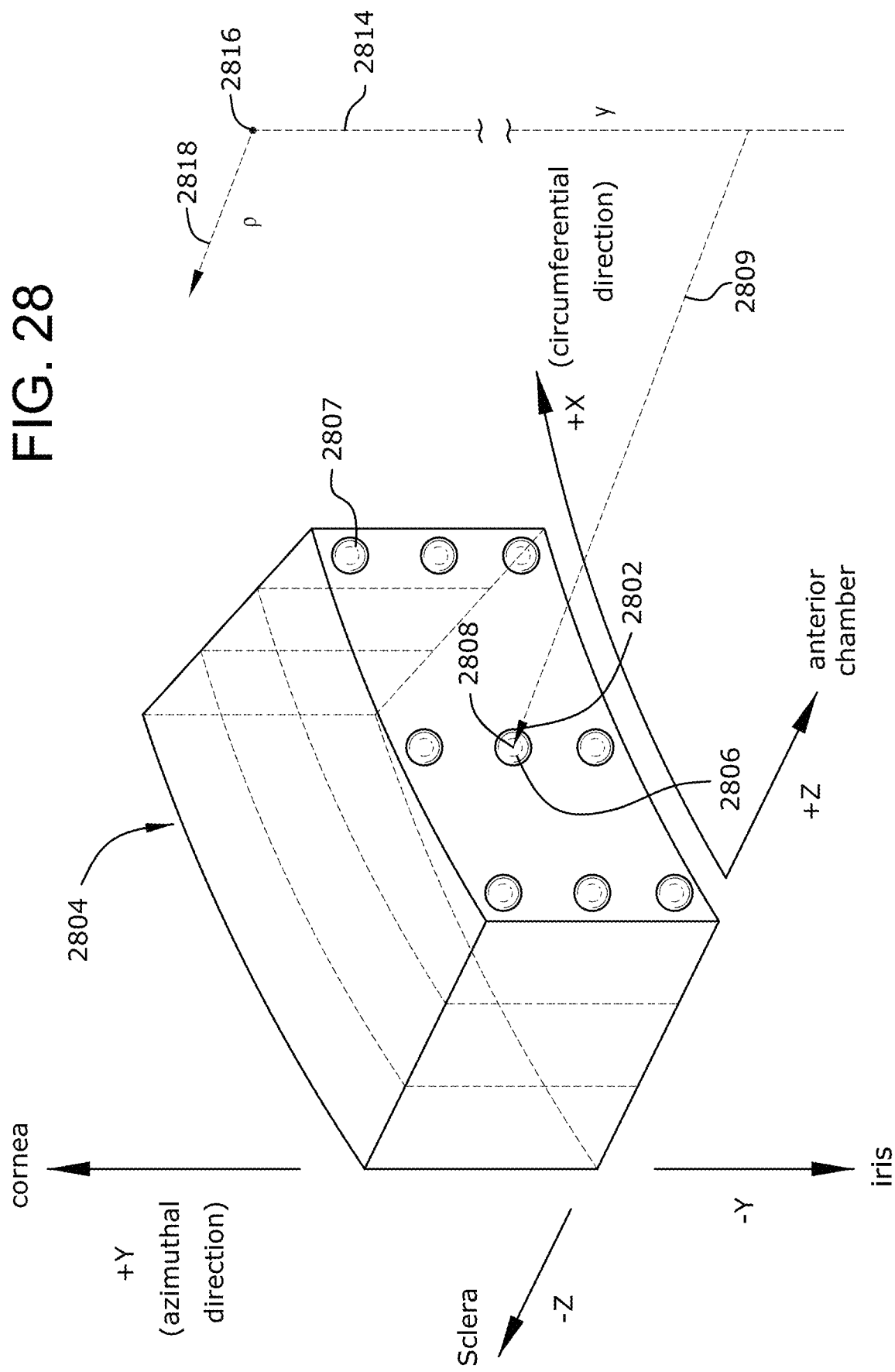
FIG. 28 is a schematic illustration of a modeled target volume of ocular tissue for which a look-up table is generated.

With reference to FIGS. 27 and 28, each coordinate set 2706 of an individual spot size distribution 2722 describes a location 2808 relative to an origin 2816. As described previously, the origin 2816 may correspond to the apex 2512 of a fixed optical component, e.g., window 801 (see FIG. 25). The location 2808 is within a modeled target volume of ocular tissue 2804. Accordingly, a laser focus 2802 positioned at the location 2808 is within the modeled target volume of ocular tissue 2804. The laser spot size 2732 associated with a coordinate set corresponds to an expected or estimated spot size 2806 for the laser focus 2802 at that location 2808. As previously noted, in a clinical setting the spot size of a laser focus may vary as a function of the location of the focus within a clinical target volume of ocular tissue. The expected or estimated spot sizes 2732 included in the individual spot size distributions 2722 account for this variation.

Continuing with FIG. 27, once a sufficient number of individual spot size distributions 2722 are created, a spot size distribution aggregator 2724 combines or aggregates the individual spot size distributions into a final spot size distribution 2726 that is defined by a collection of coordinate sets 2706 and a laser spot size 2732 for each coordinate set in the collection. Based on the final spot size distribution 2726 and energy parameter information, a mapping module 2728 produces a look up table 2704 that maps each of the coordinate sets 2706 to one or more energy parameters 2708.

Having thus described the general functions of the various modules of the look up table generator 2702, a detailed description of the method of FIG. 26 follows.

With reference to FIG. 26 and additional reference to FIGS. 27 and 28, at block 2602, a plurality of individual spot size distributions 2722 are determined for a modeled target volume of ocular tissue 2804. The modeled target volume of ocular tissue 2804 may correspond to, for example, a small portion, e.g., between 10 μm and 2000 μm, of tissue along or around the circumferential angle of the eye. Each of the plurality of individual spot size distributions 2722 is based on a different set of simulated patient data 2712 and includes an expected or estimated spot size 2732 of a laser focus 2802 at each of a plurality of locations 2808 within the modeled target volume of ocular tissue 2804. The individual spot size distributions 2722 may be further based on different sets of simulated optics data 2713.

The different sets of simulated patient data 2712 include anatomical measurements of the eye. These simulated anatomical measurements may include one or more of a central corneal thickness (CCT) 2701, a white-to-white (W2W) diameter 2703, and an anterior cornea radius of curvature Ra 2705. The different sets of simulated patient data 2712 also include an age-based conic constant k 2707.

The clinical model simulator 2710 is configured to generate a large number of different sets of simulated patient data 2712. In one configuration, each set of simulated patient data 2712 includes a simulated measure of CCT, W2W, and Ra. The simulated age-based conic constant k 2116 is based on Eq. 2 and the clinical model simulator 2710 may generate these conic constants by first generating a range of simulated ages and then deriving, for each simulated age, a simulated conic constant k 2707. Each set of stimulated patient data 2712 may be automatically generated using know simulation algorithms.

The optical model simulator 2720 is configured to generate a large number of different sets of simulated optics data 2713. The different sets of simulated optics data 2713 include parameters of optical components of a surgical system that couple to the eye during a treatment procedure. These simulated optics data 2713 may include, for example, one or more of a thickness t 2715 of a window 801 or a radius of curvature RC 2717 of the concave surface of the window. Each set of stimulated optics data 2713 may be automatically generated using know simulation algorithms.

The simulated optics data 2713 provided by the optics model stimulator 2720 is included in the modeling process to account for optical aberrations of one or more of the simulated optics of a laser surgical system, and an anatomy of the simulated patient, while simulating a propagation path of a laser beam. Optical aberrations of optics, e.g., the exit lens 710 of the focusing objective head, the window 801 of the patient interface, to be used during a procedure determine the spot size throughout the volume of ocular tissue. For a complex optical design, there are many optical variables and mechanical variables which can lead to optical aberrations. Optical tolerances may include but are not limited to surface radius of curvature, irregularity, glass thickness, Abbe number, and index of refraction, the flatness of reflective surfaces and the wedge of each lens (runout). Mechanical tolerances may include but are not limited to tilt and decenter of individual components such as lenses, mirrors and dichroics and tilt/decenter for sub-assemblies and assemblies. A ray tracing module 2730 of the look up table generator 2702, which is described later below further accounts for these optical aberrations as part of the simulation and ray tracing process.

A simulated patient's anatomy may also contribute to optical aberrations. For example, the steeper a patient's posterior surface of a cornea, the more the light bends and the more aberrations are produced. Or the smaller the eye, the higher up (closer to the global datum) the trabecular meshwork 12 is, which leads to more aberrations. More aberrations result in a larger spot size. As previously mentioned, a certain fluence is required to cause photodisruption and "cut" human tissue. This fluence is approximately 1 $J/cm^2$. Accordingly, if the spot size of a laser focus is larger due to optical aberrations, then to ensure the same fluence, the energy should be increased. The ray tracing module 2730 also accounts for these optical aberrations as part of the simulation and ray tracing process.

The focusing objective head of a surgical system, mounted on a motorized translation stage, moves to function as a "compensator" and ensures a tightly focused, near or fully diffraction-limited spot size at different depth planes. The optical design has been optimized through a large depth range, such that as the objective moves, the focus moves with it. The overall outcome is not a constant spot size with depth, but instead the spot size change is minimized through depth. As the laser focus targets different x, y and z locations, the amount and type of optical aberrations change. So incorporating a moving group of lenses provides an additional design "degree of freedom" to minimize these depth-dependent aberrations. Accordingly, movement of the objective to account for variations in the location of the trabecular meshwork 12 of the simulated patients is also accounted for by the ray tracing module 2730 in the simulation and ray tracing process (described later below).

In one example process of generating a look up table 2704, the clinical model simulator 2710 simulated 2500 patients by generating 2500 unique, different sets of simulated patient data 2712 for one modeled target volume of ocular tissue 2804 of the circumference of the eye using Monte Carlo distributions. As previously mentioned, the modeled target volume of ocular tissue 2804 may correspond to, for example, a small portion, e.g., between 10 μm and 2000 μm, of tissue along or around the circumferential angle of the eye. For the CCT 2701 distribution, a literature review was conducted to find published clinical study data. In each study, a mean and standard deviation value of CCT 2701 was reported. The results from the studies were combined to calculate an aggregate, mixture average and standard deviation for CCT 2701, which were used for Monte Carlo distribution purposes. This process was repeated for the distributions of the white-to-white diameters W2W 2703, and the natural anterior radii of curvature Ra 2705.

The optical model simulator 2720 generated 2500 unique, different sets of simulated optics data 2713 using Monte Carlo distributions.

Figure 1:
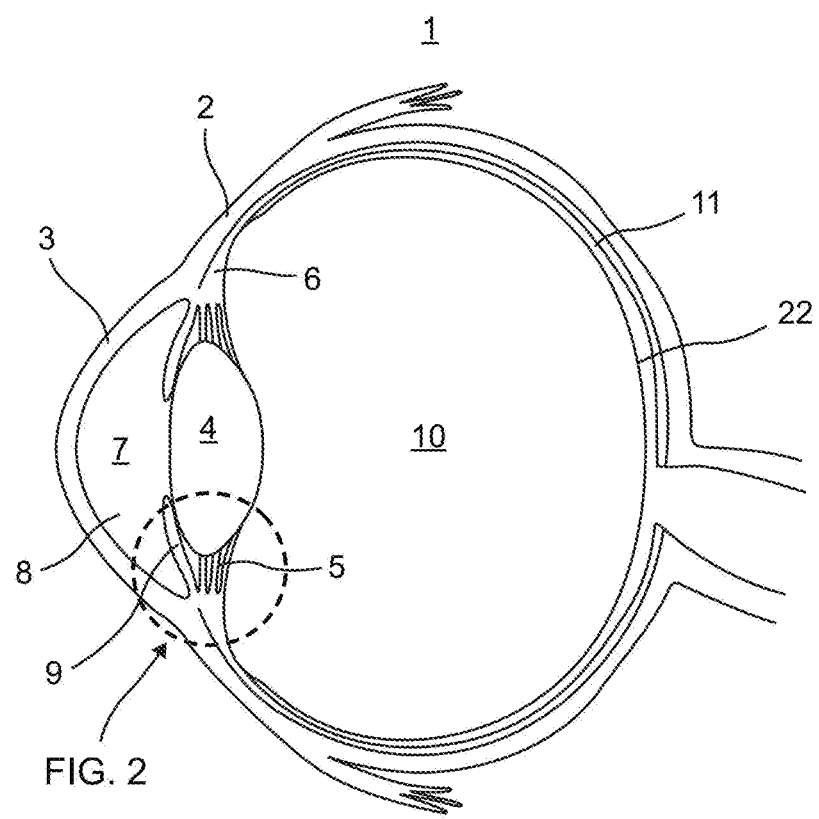
FIG. 1 is a sectional schematic illustration of a human eye and its interior anatomical structures.
Figure 3:
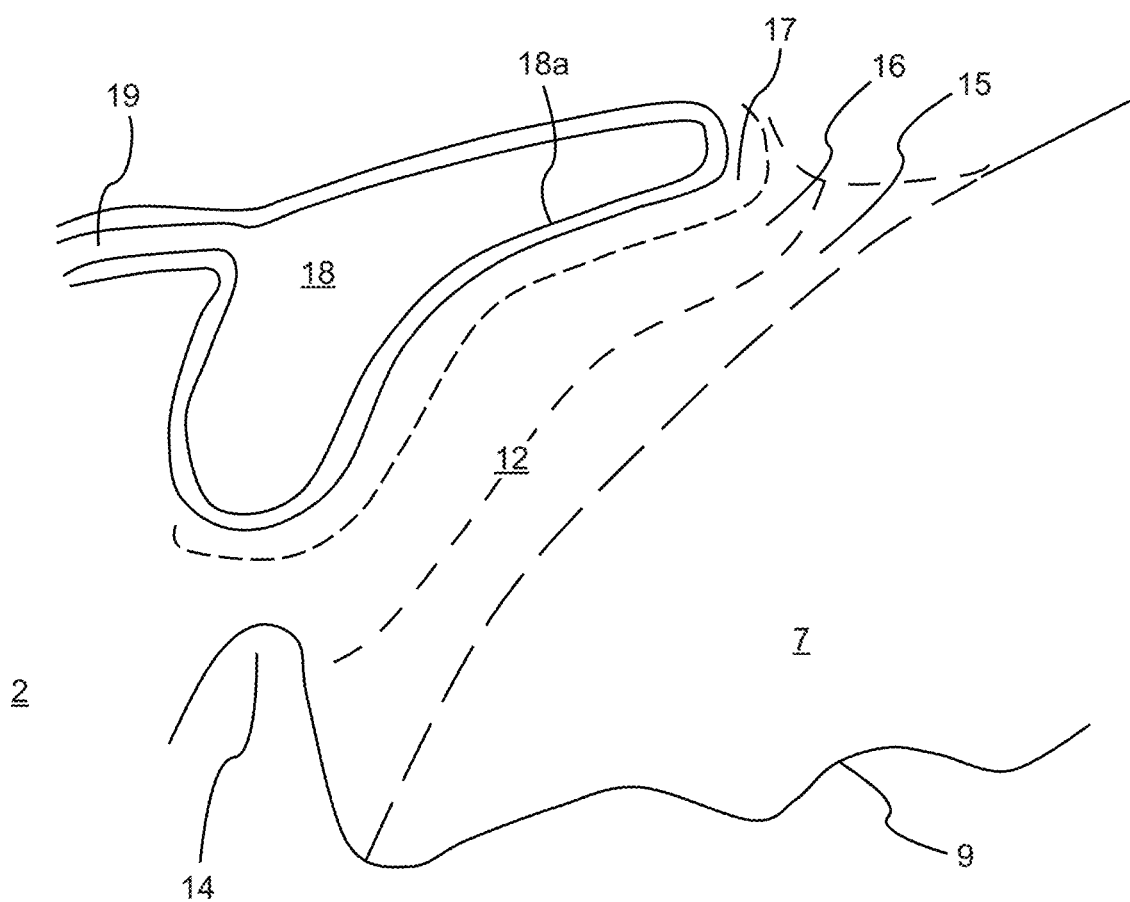
FIG. 3 is a sectional schematic illustration detailing anatomical structures in the irido-corneal angle of FIG. 2, including the trabecular meshwork, Schlemm's canal, and one or more collector channels branching from the Schlemm's canal.
Figure 4:
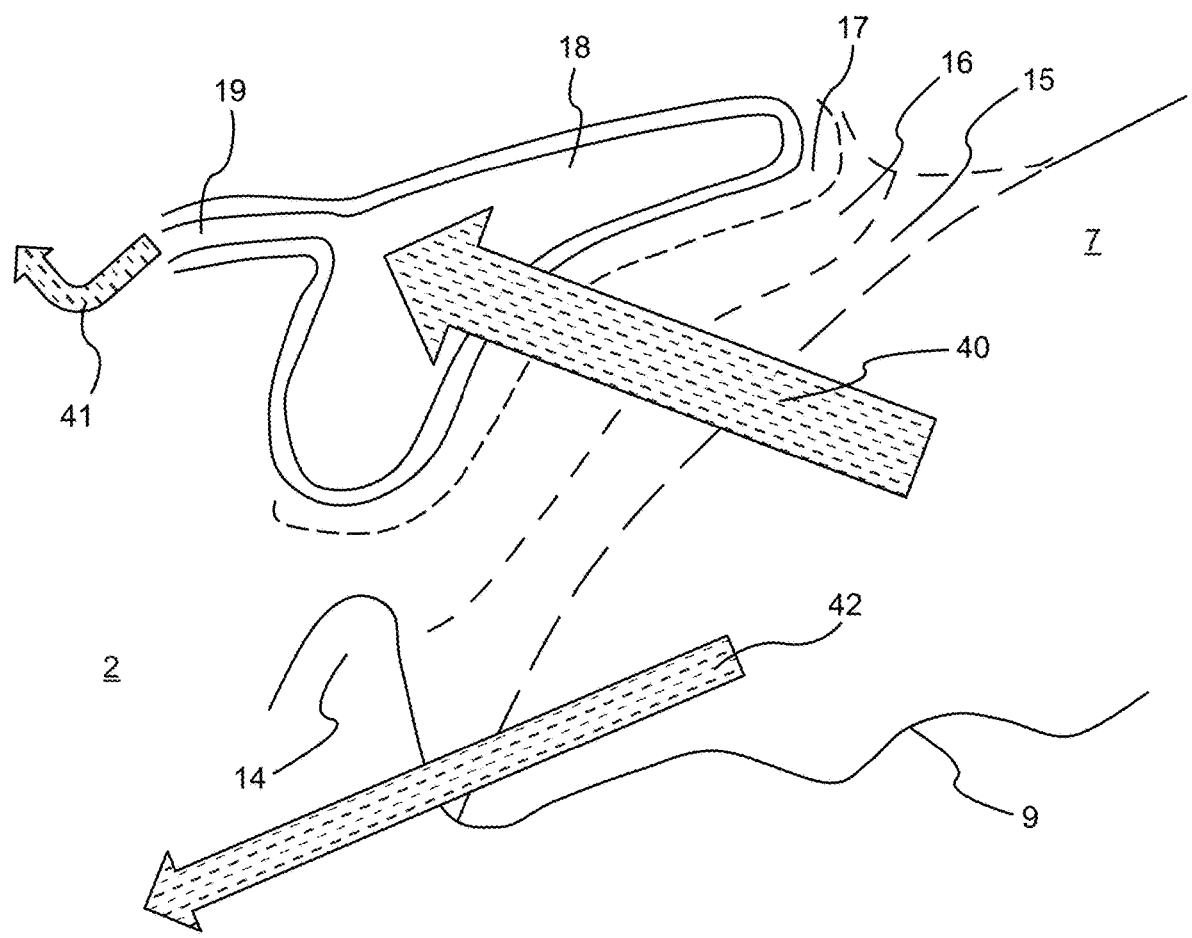
FIG. 4 is a sectional schematic illustration of various outflow pathways for aqueous humor through the trabecular meshwork, Schlemm's canal, and collector channels of FIG. 3.
Figure 5:
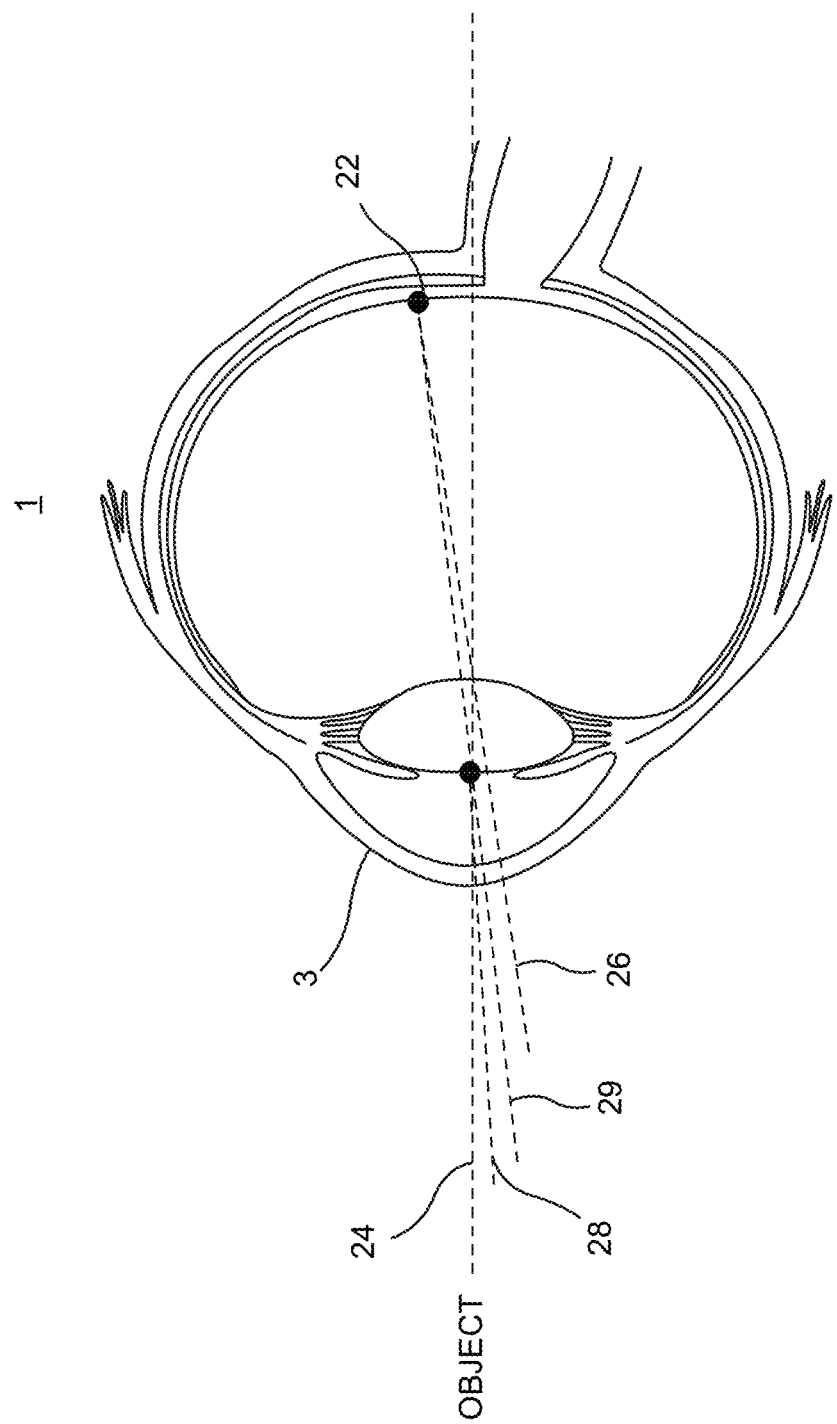
FIG. 5 is a sectional schematic illustration of a human eye showing various axes associated with the eye.
Figures 2, 29A:
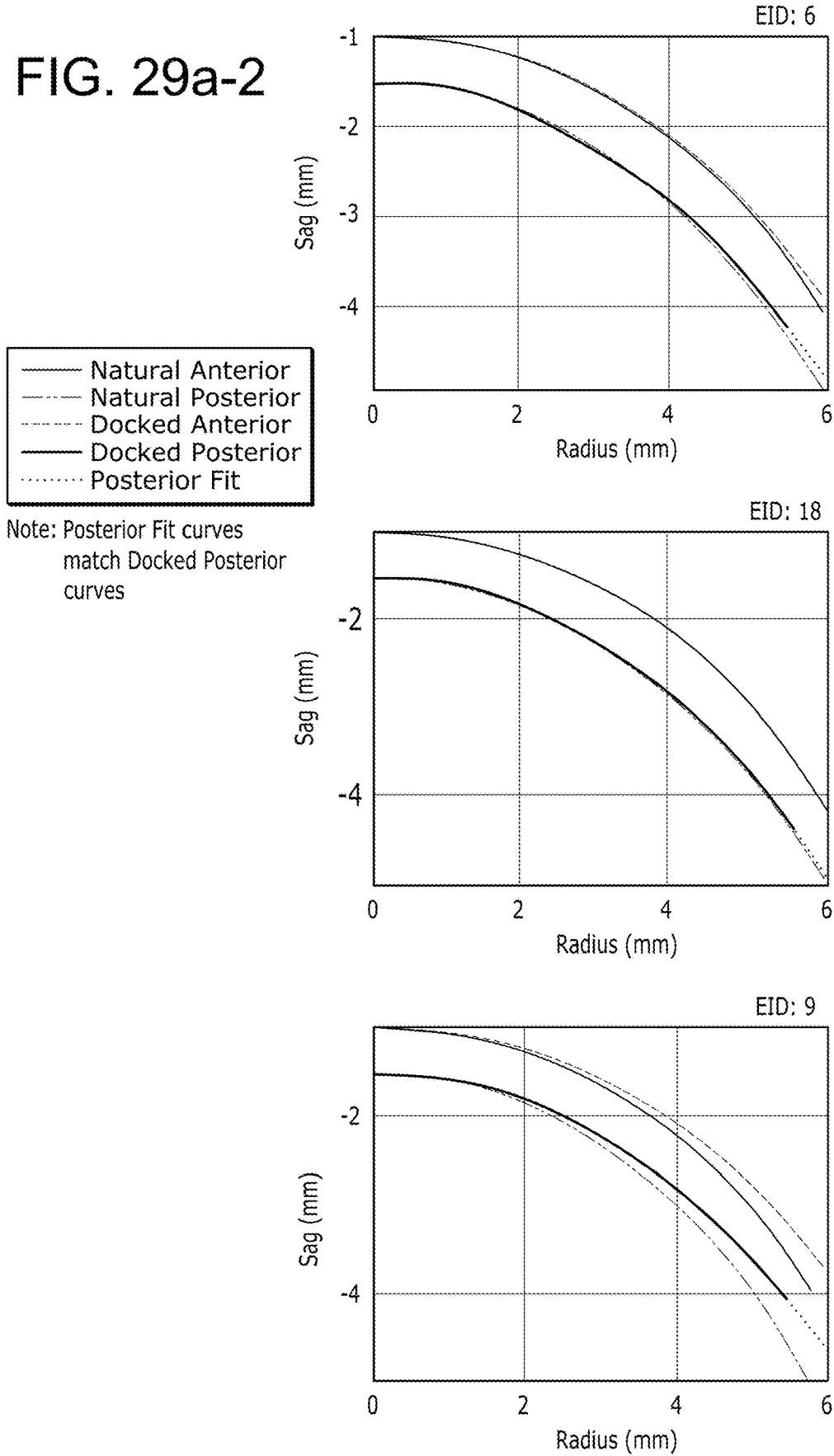

Having generated different sets of simulated patient data 2712 and simulated optics data 2713 (collectively referred to herein as simulated data) the anatomical anchor locator 2714 determines a location of the anatomical anchor 14 for each set of simulated data. To this end, and with reference to FIGS. 29a-1 through 29a-3, for each set of simulated data:

1) The anatomical anchor locator 2714 generates a natural anterior curve based on simulated patient data 2712, including the W2W, k (which may be derived using Eq. 2 and based on simulated age), and the anterior radius of curvature Ra. This is done using the following equation:

$$y = \frac{cr^2}{1+\sqrt{1-(1+k)c^2r^2}} + CCT + t \quad \text{(Eq. 9)}$$

where:
y is sag, the distance from the origin along the Sag (mm) axis (note that the origins in the graphs of FIGS. 29a-1 through 29a-3 are not shown and are at "0", above −1;
c is the curvature (the inverse of the simulated base anterior radius of curvature Ra 2705);
k is the simulated conic constant 2707;
r is the radius, the distance from the origin along the Radius (mm) axis;
CCT is the central corneal thickness 2701; and
t is the simulated thickness of the optical component, e.g., window 801.

The simulated c (the inverse of the simulated base anterior radius of curvature Ra) and the simulated conic constant k are substituted in Eq. 9, and a number of different radius positions from the origin out to one-half of the simulated W2W 2703 are individually substituted for r to obtain a corresponding number of values of y. In one example, the number of radius positions is 500. The values of y as a function of r define a curve corresponding to the natural anterior curve. Examples of natural anterior curves are illustrated in FIGS. 29a-1 through 29a-3.

2) The anatomical anchor locator 2714 then generates a natural posterior curve based on simulated patient data 2712, including the W2W, k, CCT, and the anterior radius of curvature Ra. This is done using the following equation:

$$y = \frac{cr^2}{1+\sqrt{1-(1+k)c^2r^2}} + CCT + t \quad \text{(Eq. 10)}$$

where:
y is sag, the distance from the origin along the Sag (mm) axis;
c is the curvature (the inverse of the simulated base posterior radius of curvature Rp, where Rp=Ra/1.22);
k is the simulated conic constant 2707;
r is the radius, the distance from the origin along the Radius (mm) axis; and
CCT is the simulated central corneal thickness 2701; and
t is the simulated thickness of the optical component, e.g., window 801.

The simulated c (the inverse of the simulated base posterior radius of curvature Rp), the simulated conic constant k, and the simulated CCT are substituted in Eq. 10, and a number of different radius positions from the origin out to one-half of the simulated W2W are individually substituted for r to obtain a corresponding number of values of y. The values of r substituted into the equation may corresponds to the same values of r substituted in Eq. 9 when generating the natural anterior curve. In one example, the number of radius positions is 500. The values of y as a function of r define a curve corresponding to the natural posterior curve. Examples of natural posterior curves are illustrated in FIGS. 29a-1 through 29a-3.

3) The anatomical anchor locator 2714 then generates a deformed anterior curve based on simulated patient data 2712, including the simulated k, and simulated optics data 2713, including the radius of curvature of a window 801 coupled to the anterior surface of the cornea of the simulated patient. This is done using the following equation:

$$y = \frac{cr^2}{1+\sqrt{1-(1+k)c^2r^2}} + CCT + t \quad \text{(Eq. 11)}$$

where:
y is sag, the distance from the origin along the Sag (mm) axis;
c is the curvature (the inverse of the simulated radius of curvature 2717 of the optical component);
k is the simulated conic constant 2707; and
r is the radius, the distance from the origin along the Radius (mm) axis.
CCT is the central corneal thickness 2701; and
t is the simulated thickness of the optical component, e.g., window 801.

The simulated c (the inverse of the simulated radius of curvature of the optical component), and the simulated conic constant k are substituted in Eq. 11, and a number of different radius positions from the origin out to one-half of the simulated W2W 2703 are individually substituted for r to obtain a corresponding number of values of y. The values of r substituted into the equation may corresponds to the same values of r substituted in Eq. 9 when generating the natural anterior curve. In one example, the number of radius positions is 500. The values of y as a function of r define a curve corresponding to the deformed anterior curve. Examples of natural posterior curves are illustrated in FIGS. 29a-1 through 29a-3.

4) The anatomical anchor locator 2714 then calculates the arc length of the natural anterior curve and the arc length of the natural posterior curve using known equations, wherein the arc length corresponds to the distance along the respective curve between the minimum radius (origin) and the maximum radius (W2W/2).

5) The anatomical anchor locator 2714 then determines a deformed posterior curve using the boundary conditions that the posterior corneal arc length is constant (does not change after deformation). In other words, the natural posterior arc length is equal to the deformed posterior arc length. With reference to FIGS. 29a-1 through 29a-3, half corneal arc lengths are shown, each corresponding to the distance along the arc from one end of the cornea 3 to point on the curve at the Sag axis.

With reference to FIG. 25, the deformation module 2718 of the anatomical anchor locator 2714 calculates a corresponding posterior surface point 2510 for each of a discrete number of anterior surface points 2506 along the deformed anterior surface 2502 arc length. Based on the previously derived natural anterior curve and posterior curves, the deformation module 2718 determines a normal thickness ($t_c$)

of the cornea 3 at various points along the length of the natural cornea. Because the thickness of the cornea 3 is not impacted by applanation of the window 801, the deformation module 2718 applies these known normal thicknesses to determine a corresponding posterior surface point 2510 for each of a number of anterior surface points. Each corresponding posterior surface point 2510 is in a direction normal to an anterior tangent 2508 through its corresponding anterior surface point 2506 and is a distance equal to the normal thickness ($t_c$) at that point from the corresponding anterior surface point 2506. The number of discrete anterior surface points 2506 may correspond to the number of radius positions used to generate the deformed anterior curve. The result is the deformed posterior curve. Examples of deformed posterior curves are illustrated in FIGS. 29*a*-1 through 29*a*-3.

6) The anatomical anchor locator 2714 then fits a deformed posterior fitted curve to the following equation using non-linear least squares to numerically calculate a deformed posterior conic constant k and deformed posterior base radius of curvature Rp:

$$y = \frac{cr^2}{1 + \sqrt{1 - (1+k)c^2 r^2}} + CCT + t \quad \text{(Eq. 12)}$$

where:
y is sag, the distance from the origin along the Sag (mm) axis;
c is the curvature (the inverse of the deformed base radius of curvature);
k is the deformed conic constant;
r is the radius, the distance from the origin along the Radius (mm) axis;
CCT is the central corneal thickness 2701; and
t is the simulated thickness of the optical component, e.g., window 801.

In the fitting process, various values for c and k are arbitrarily selected and values of y are determined, until the values for y from the origin along the Radius (mm) axis define a deformed posterior fitted curve that closely fits to the deformed posterior curve. The values for c and k that produce the deformed posterior fitted curve define the deformed posterior base radius of curvature Rp 2711 and a deformed conic constant k 2719 for the simulated patient.

Regarding the various simulated patients shown in FIGS. 29*a*-1 through 29*a*-3, differences in simulation cases are noted. For example, consider EID 12. Here the simulated patient's natural anterior curve is flatter than the patient's deformed curve due to applanation of the patient interface (e.g., window 801). When docking occurs the simulated patient's cornea is forced to the steeper patient interface shape. This causes the posterior surface to also "bend" down, as shown by the deformed posterior curve relative to the natural posterior curve. Therefore, for this simulated patient, the anatomical anchor location (which is at the end of the posterior fitted curve) is deeper into the trabecular meshwork (larger, more negative sag value) after deformation than in its natural state. Thus, the sag value corresponding to the end of the posterior fitted curve is greater (e.g., more negative) than the sag value corresponding to the end of the natural posterior curve. For the simulated patient of EID 9, the opposite is true and instead the anatomical anchor location (which is at the end of the posterior fitted curve) is shallower than its natural position. Thus, the sag value corresponding to the end of the posterior fitted curve is less (e.g., less negative) than the sag value corresponding to the end of the natural posterior curve.

Having now determined a deformed posterior base radius of curvature Rp 2711 and a deformed conic constant k 2719 for the simulated patient based on the simulated patient data 2712 and the simulated optics data 2713, the coordinate set 2716 of the location of an anatomical anchor 14 may be determined based on a coordinate system. For example, using a cylindrical coordinate system with the origin 2816 defined at the apex of the window 801 of the patient interface—a fixed location associated with optics of the surgical system that is invariant of patient anatomy—then the coordinates (ρ, θ, y) of the location 2808 of the scleral spur 14 of the simulated patient is obtained by inserting values for p, Rp, k, CCT, and t in the following equation to solve for y:

$$y = \frac{c\rho^2}{1 + \sqrt{1 - (1+k)c^2 \rho^2}} + CCT + t \quad \text{(Eq. 13)}$$

where:
y is the distance from the origin 2816 along the y axis 2814;
ρ is the radial distance from the origin 2816 along the ρ axis 2818 and is set equal to one-half of W2W;
c is the inverse of Rp, where Rp is the deformed posterior base radius of curvature 2711 of the simulated patient;
k is the deformed conic constant 2719;
W2W is the white-to-white diameter 2703;
CCT is the central corneal thickness 2701; and
t is the simulated thickness of the optical component, e.g., window 801.

Figure 29B:
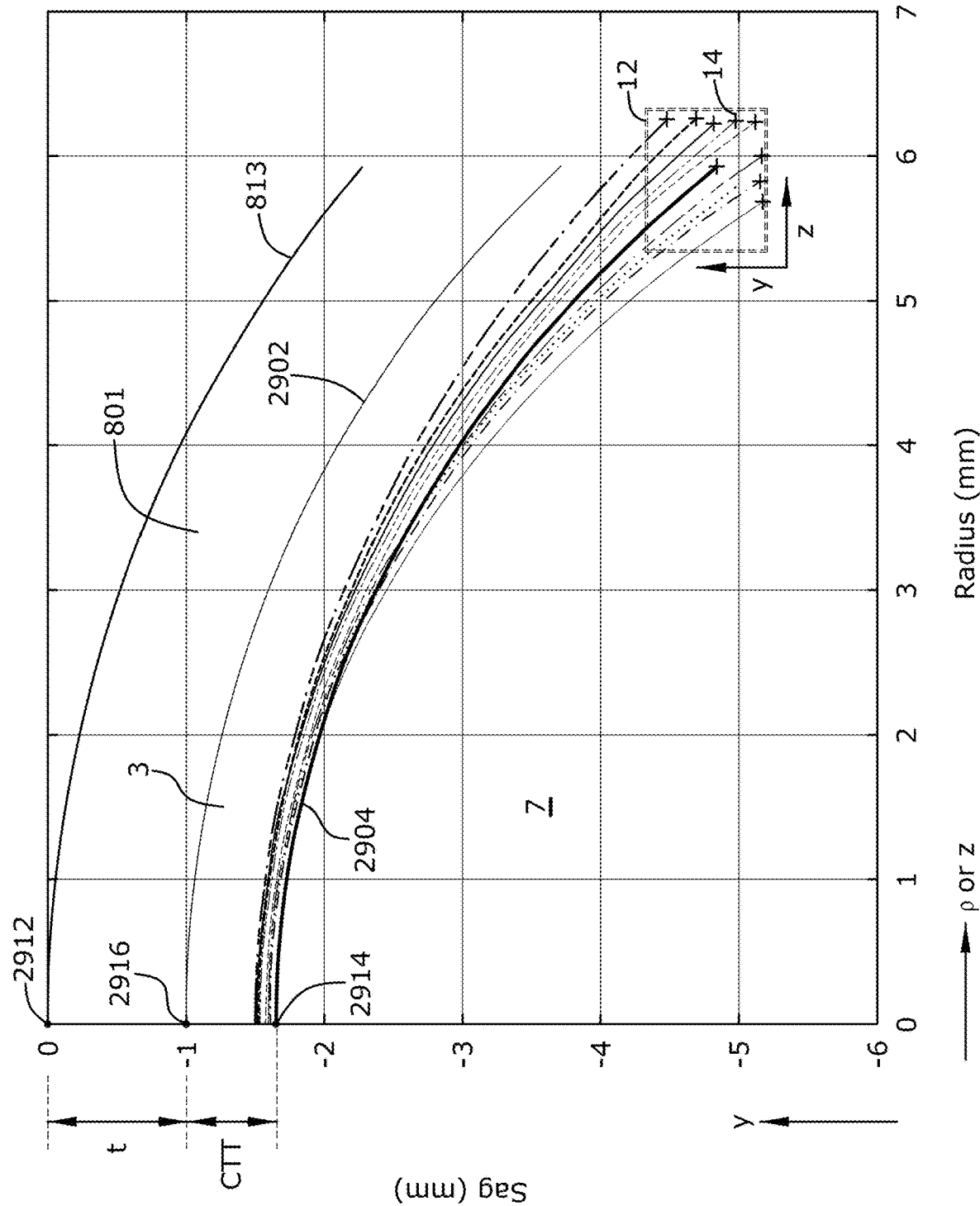
FIG. 29b is a graph illustrating various fitted deformed posterior corneal curves for various simulated patients, and locations of anatomical anchors corresponding to sclera spurs, as may be determined by the look up table generator.
Figure 30:
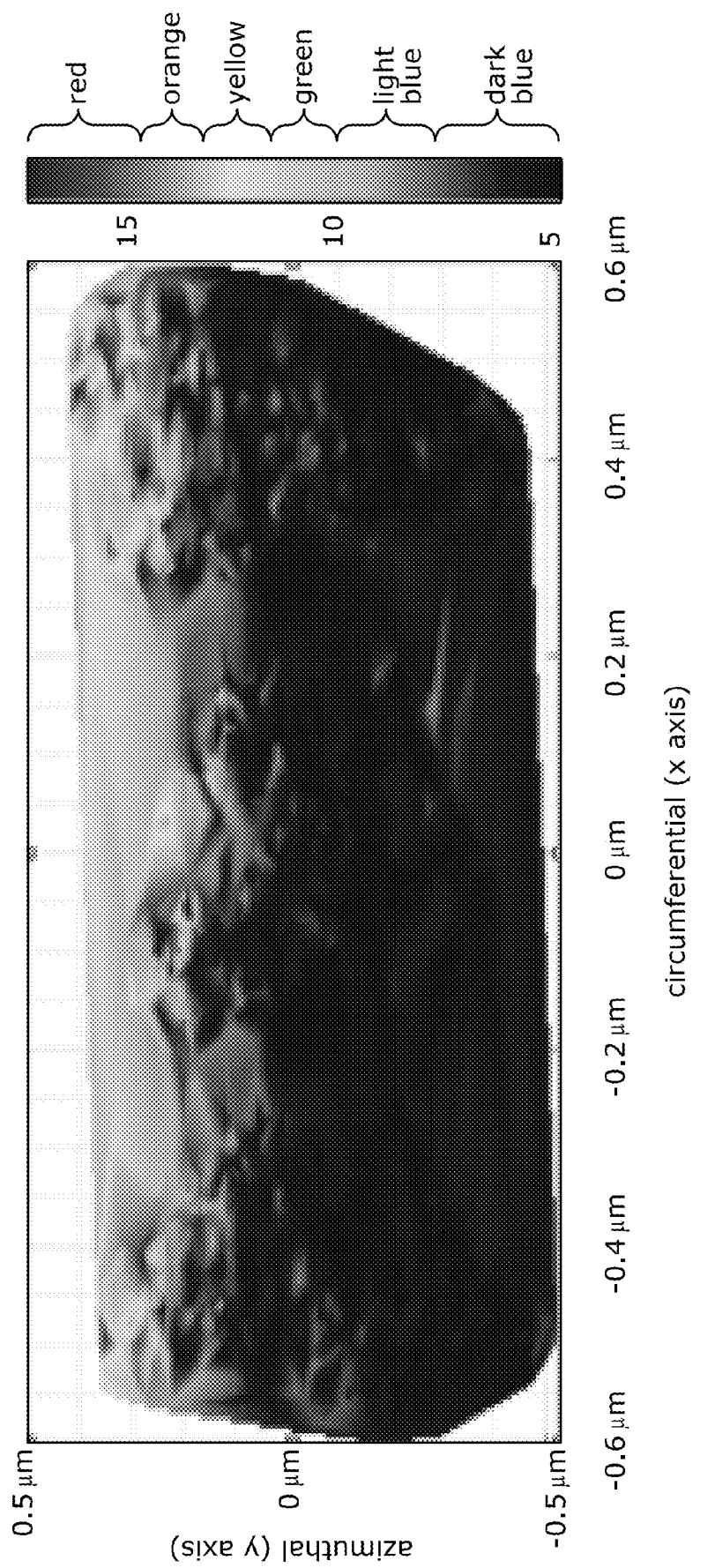
FIG. 30 is a graph illustrating a final spot size distribution of a laser focus as a function of focus location in a treatment layer, e.g., XY plane, of a target volume of ocular tissue.

With reference to FIG. 29*b*, and continuing with the 2500 anatomical model simulation described above, the deformed posterior curve 2904 of the cornea 3 of a number of simulated patient is represented by a separate curved line in a single graph. For clarity of illustration only ten curved line are shown. For each simulated patient, the location of the scleral spur 14 and therefore trabecular meshwork 12 is at the end of the curved line representing the deformed posterior surface 2904. For each simulated patient, the z-axis or p-axis span is equal to half the W2W diameter. The sag (y) is determined from Eq. 13 above for y(θ). The apex of the anterior surface of the window 801, is taken as the origin. Regarding Eq. 13, in the model each of t and CCT is considered to be a constant, and the last two terms in Eq. 13 represent a fixed offset which is the distance from a simulated origin 2912 to a simulated apex 2914 of the posterior surface 2904 of the cornea 3.

Continuing further with block 2602 of FIG. 26, and with additional reference to FIGS. 27 and 28, having determined the location of the anatomical anchor 14 for a set of simulated patient data, a ray tracing module 2730 determines an individual spot size distribution 2722 for each different set of simulated patient data. To this end, the ray tracing module 2730 simulates a propagation path 2809 of a laser beam through an anterior chamber 7 of an eye into the determined location of the anatomical anchor 14, and calculates a spot size 2806 of the focus of the laser beam at the location of the anatomical anchor and at other coordinate locations 2807 about the anatomical anchor, through which the focus may be scanned. The optics model simulator 2720 may simulate the propagation path of a laser beam and calculate spot sizes using geometric ray tracing capabilities of an engineering optical physics software, such as Zemax OpticStudio.

In the example based on 2500 sets of simulated data, for each of the 2500 simulations, the optics model simulator 2720 ran a ray trace to calculate the femtosecond spot size at twenty-seven different locations 2806, 2807 covering a representative channel in the trabecular meshwork sized 200 µm azimuthal×500 µm circumferential×400 µm depth. Different sized channels are possible. For example, the circumferential size may be increased to extend the spot size distribution further around the circumference of the eye. In any case, the entire volume of ocular tissue covered by the location of these 2500 channels is referred to herein as a surgical volume or surgical envelope. The representative surgical volume was anchored at the scleral spur x, y, and z location as determined by the anatomical anchor locator 2714. The spot size metric was taken to be the diameter encircling focused energy values of 10% to 90%. With reference to FIG. 28, these twenty-seven locations 2806, 2807 comprised three sets of nine locations each, where each set was evaluated at a different fixed depth z location. The depth planes or slices were spaced apart evenly throughout the volume (0, 200 and 400 µm relative to the starting position). Note for clarity of illustration, only one set of nine locations 2806, 2807 is shown in FIG. 28. Also, while the spot sizes at the nine location 2806, 2807 are shown as the same size, the actual spot sizes may vary, with some of them being larger or smaller than illustrated in FIG. 28.

Further describing the ray tracing process, rays are traced through the optical system and light-matter interaction (reflection, refraction) are calculated for each ray at each surface. In each case of refraction of reflection, the equations are known and the subsequent trajectory of the ray can be calculated using these known equations. In this way, each ray trajectory is sequentially traced through the optical system.

All of these rays strike the "image," which is the surface at the ray's terminate. In this case, the "image" is the surface of the trabecular meshwork.

These rays do not all converge on a single, infinitesimally small point and instead "spread out." The level of spread is due to two major factors. Firstly, the laws of physics (diffraction) which govern a finite, minimum spot size. Secondly, the tolerances and variations described above (optical, mechanical and anatomical) which will cause the spot size to further expand beyond the diffraction limit. The second component are known as introducing "aberrations" and the heterogenous eye anatomy is a key component of these aberrations. For example, because of the oblique angle at which a laser may enter the eye in the integrated surgical system 1000 disclosed herein, astigmatism is the primary anatomy-induced aberration. To a secondary degree, another aberration known as "coma" differs across the patient population.

The spatial distribution of where these rays fall on the image, e.g., the surface of the trabecular meshwork, can be mathematically calculated in different ways to calculate a spot size. The ray tracing module 2730 uses the D1090 value, which is a well-established metric for measuring and calculating laser spot sizes. The spot size physically represents the area within which a defined amount of energy resides. The larger the spot size, the more spread out the energy is, and therefore the more input energy is required to achieve the photodisruption threshold for tissue. Furthermore, the shape of the spot is also important and the spot size calculation captures this also. The difference in eye anatomy will cause the ray to trace differently through the eye, will introduce different aberrations, and will affect the spot size.

Regarding the D1090 spot size calculation method, this method is equivalent to a "knife-edge width" measurement where the "width of the beam is defined as the distance between the points of the measured curve that are 10% and 90% of the maximum value. Prior to advanced software and CCD cameras, the knife edge method was the standard laboratory technique. It corresponds to measuring the total beam energy and then traversing a knife-edge so that it encroaches on the beam and subsequently reduces the power recorded on a detector. The knife blade is moved at fixed increments until the detector records zero power. A computational equivalent of this knife edge technique may be used to calculate spot size. While not a standard measurement, it is ISO recommended and one that is used by companies that make beam measurement technology. See for example, White Paper—Apples to Apples: Which Camera Technologies Work Best for Beam Profiling Applications, Part 2: Baseline Methods and Mode Effects, by G. E. Slobodzian (https://www.ophiropt.com/laser—measurement/knowledge-center/article/8065?r=blog).

Returning to FIG. 26, and with additional reference to FIG. 27, at block 2604, the individual spot size distributions 2722 resulting from the number of simulations and generated by the ray tracing module 2730 are aggregated or combined to obtain a final spot size distribution 2726. For example, the spot sizes across different individual spot size distributions 2722 that are in spatially overlapping locations within a simulated target volume of ocular tissue may be combined using known interpolation techniques, such as gridded interpolation. The combined spot size distribution includes a final expected or estimated spot size of the laser focus at the plurality of locations of the focus within a simulated target volume of ocular tissue.

For a single patient, as per FIG. 28, there are a 9 simulated spots at three different depth planes, for a total of 27 spots per patient. Each one of these spots has a spatial co-ordinate (x, y, z). For n patients, there would then be 27n spots. Mathematically, this data could be described in a matrix (table) with 27n rows and 4 columns. Each row represents a spot with the first column as a spot size D1090 value, and the second, third and fourth columns are the corresponding x, y, and z co-ordinate value for that spot size, respectively. Rows 1-27 would be for the first patient, 28-54 for the second patient, 55-81 for the third patient, etc. until row 27n.

The total ocular surgical envelope represents a volume that is bounded by the minimum and maximum values of x, y, and z. The surgical volume can be discretized in all three dimensions with equal spacing such that it is a 3D "mesh" or a "grid", somewhat like a crystal lattice. For example, with equal spacing of 0.01 in all three dimensions, if the minimum and maximum values of x are −1 to 1, y are −2 to 2, and z are −3 to 3, then there would be 200 grid points in x, 400 in y and 600 in z, for a total of 200×400×600 points (minus the number of corners, 8, where there is overlap between the gridded points). Grid interpolation is a numerical method of using the data (the 27n×4 matrix described above) to interpolate a spot size to each of the x, y and z locations of the grid. For example, for a particular grid location of x', y', and z', the algorithm is configured to find the nearest six (x, y, z) locations in the simulated spot size matrix and estimate the spot size at (x', y', z') by using mathematical interpolation. Interpolation is essentially an "estimation"—finding new data values based on measured (in case simulated) data. Six is just an example number. This gridded interpolation may be done in MATLAB.

Figure 31:
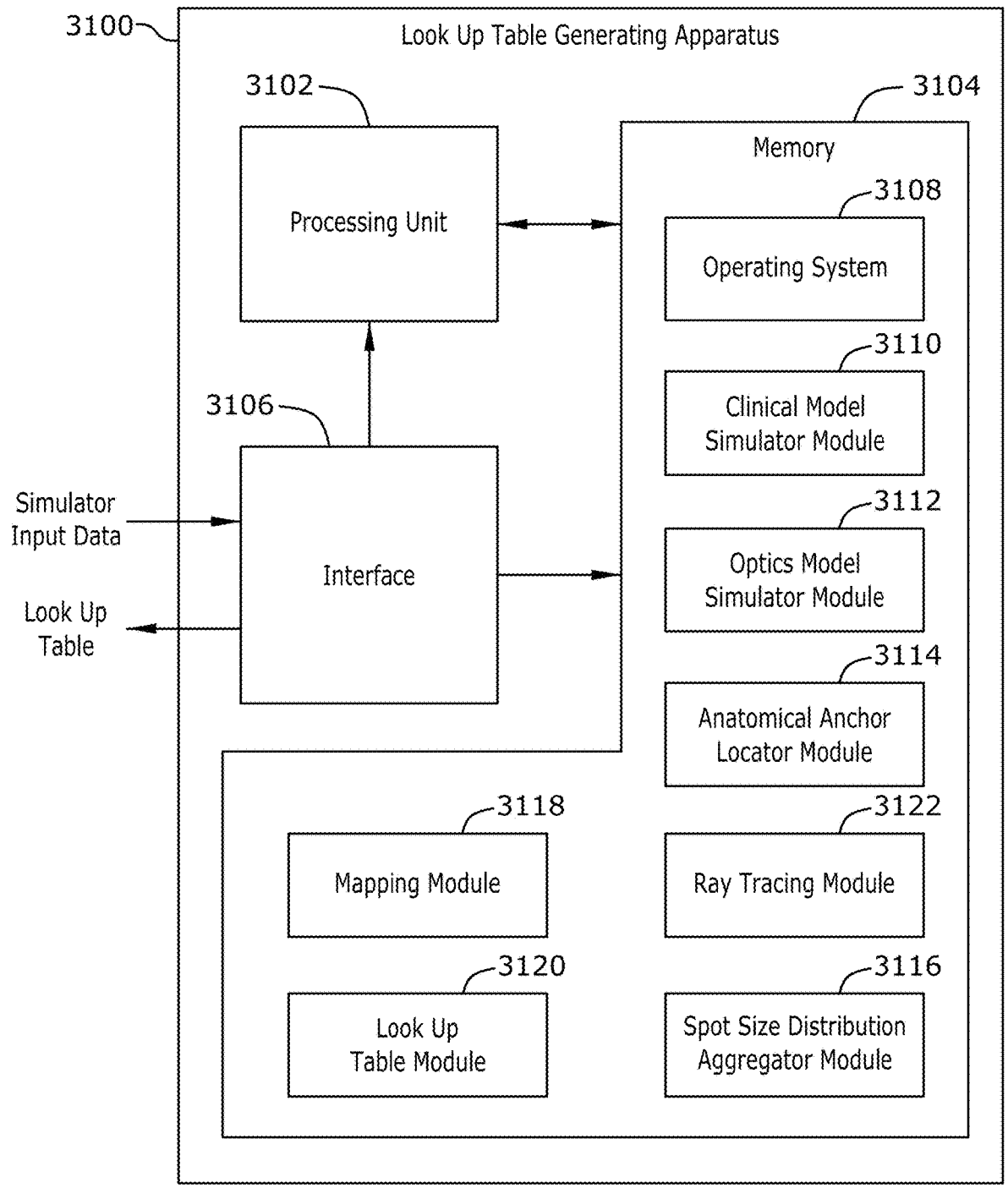
FIG. 31 is a schematic diagram of the look up table generator of FIG. 27.

Continuing with the example based on 2500 simulations and 2500 corresponding individual spot size distributions 2722, the complete Monte Carlo analysis, e.g., the collective results of the ray tracing across all 2500 simulated patient, furnished 67500 (2500 simulations with 27 spots each) discrete spot size values, within a full surgical envelope sized 200 µm azimuthal×500 µm circumferential×400 µm depth. With reference to FIG. 31, an example slice of a final spot size distribution 2726 at a particular depth z in the surgical volume resulting from the above described Monte Carlo analysis is shown. The horizontal axis is the circumferential extent in microns of the envelope and the vertical axis in microns is the azimuthal extent. The modeled spot is shown from 5 µm (blue) to about 20 µm (red). The blue areas indicate the places in the surgical volume where the projected spot size is about 5 µm whereas the red areas indicate places where the spot size is as great as 15 µm. In principle, blue areas need less laser energy to treat tissue, while red areas need more laser energy. Larger spot sizes correspond to higher energy levels. The final spot size distribution 2704 may be represented in the form of a look up table.

At block 2606 of FIG. 26, having obtained a final spot size distribution for the target volume of ocular tissue, an energy value is assigned or mapped to the plurality of locations of the laser focus within the target volume of ocular tissue based on the final expected spot size at that location. Available energy parameter information, such as shown in Table 6 below, may be used to assign an energy value to the plurality of locations of the focus. For example, a location have a spot size in the range of 5.00 to 9.99 µm would be assigned an energy level of 0.6 µJ.

TABLE 6

| Spot Diameter (µm) | Assigned Energy (µJ) |
| --- | --- |
| 5.00 to 9.99 | 0.6 |
| 10.00 to 14.99 | 2.4 |
| 15.00 to 19.99 | 5.3 |
| 20.00 to 24.99 | 9.4 |

While the generated look up table 2704 for the modeled target volume of ocular tissue 2804 is only for a portion of the circumference of the irido-corneal angle, the same look up table 2704 may be applied to all locations around the entire circumference of the irido-corneal angle. In other words, the forgoing process of generating the look up table does not have to be repeated for different rotational locations around the circumference of the irido-corneal angle. Alternatively, the entire method of FIG. 26 may be repeated for one or more additional target volumes within ocular tissue of the irido-corneal angle. For example, with reference to FIG. 28, the process may be repeated for a number of adjacent additional modeled target volumes 2804 around a portion of the circumference of the irido-corneal angle. The portion of the circumference may be characterized in degrees, e.g., 90°, 180°, 270°, 360°, etc., around the entire circumference of the irido-corneal angle.

FIG. 31 is a schematic block diagram of an apparatus 3100 corresponding to the look up table generator 2702 of FIG. 27. The apparatus 3100 is configured to execute instructions related to the look up table generation processes described above with reference to FIGS. 26-30. The apparatus 3100 may be embodied in any number of processor-driven devices, including, but not limited to, a server computer, a personal computer, one or more networked computing devices, a microcontroller, and/or any other processor-based device and/or combination of devices.

The apparatus 3100 may include one or more processing units 3102 configured to access and execute computer-executable instructions stored in at least one memory 3104. The processing unit 3102 may be implemented as appropriate in hardware, software, firmware, or combinations thereof. A hardware implementation may be a general purpose processor, a digital signal processor (DSP), an application specific integrated circuit (ASIC), a microprocessor, a microcontroller, a field programmable gate array (FPGA), a System-on-a-Chip (SOC), or any other programmable logic component, discrete gate or transistor logic, discrete hardware components, or any combination thereof, or any other suitable component designed to perform the functions described herein. Software or firmware implementations of the processing unit 3102 may include computer-executable or machine-executable instructions written in any suitable programming language to perform the various functions described herein.

The memory 3104 may include, but is not limited to, random access memory (RAM), flash RAM, magnetic media storage, optical media storage, and so forth. The memory 3104 may include volatile memory configured to store information when supplied with power and/or non-volatile memory configured to store information even when not supplied with power. The memory 3104 may store various program modules, application programs, and so forth that may include computer-executable instructions that upon execution by the processing unit 3102 may cause various operations to be performed. The memory 3104 may further store a variety of data manipulated and/or generated during execution of computer-executable instructions by the processing unit 3102.

The apparatus 3100 may further include one or more interfaces 3106 that facilitate communication between the apparatus and one or more other apparatuses. For example, the interface 3106 may be configured to receive patient data to be used by a clinical model simulator. The interface 3106 is also configured to transmit generated look up tables to the control system 100 of FIG. 23. Communication may be implemented using any suitable communications standard. For example, a LAN interface may implement protocols and/or algorithms that comply with various communication standards of the Institute of Electrical and Electronics Engineers (IEEE), such as IEEE 802.11.

The memory 3104 may store various program modules, application programs, and so forth that may include computer-executable instructions that upon execution by the processing unit 3102 may cause various operations to be performed. For example, the memory 3104 may include an operating system module (O/S) 3108 that may be configured to manage hardware resources such as the interface 3106 and provide various services to operations executing on the apparatus 3100.

The memory 3104 stores operation modules such as a clinical model simulator module 3110, an optics model simulator module 3112, an anatomical anchor locator module 3114, ray tracing module 3122, a spot size distribution module 3116, a mapping module 3118, and a look up table module 3120. These modules may be implemented as appropriate in software or firmware that include computer-executable or machine-executable instructions that when executed by the processing unit 3102 cause various operations to be performed, such as the operations described above with reference to FIGS. 26-30. Alternatively, the modules may be implemented as appropriate in hardware. A hardware implementation may be a general purpose processor, a DSP, an ASIC, a FPGA or other programmable logic component, discrete gate or transistor logic, discrete hardware components, or any combination thereof, or any other suitable component designed to perform the functions described herein.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A system for photodisrupting a target volume of ocular tissue with a laser, the target volume of ocular tissue associated with an eye of a patient, the system comprising:
   a first optical subsystem including one or more optical components configured to be coupled to the eye;
   a second optical subsystem including a laser source configured to output a laser beam, and a plurality of components optically coupled between the laser source and the first optical subsystem; and
   a control system coupled to the first optical subsystem and the second optical subsystem and configured to:
      derive an initial coordinate set based on a function that is based on data of the patient including a central corneal thickness (CCT), a white-to-white (W2W) diameter at a meridian of a cornea of the eye, and an anterior cornea radius of curvature Ra at the meridian of the cornea of the eye, the initial coordinate set corresponding to an initial location within a target volume of ocular tissue;
      determine an energy parameter from a database that maps a plurality of coordinate sets of locations within the target volume of ocular tissue, including the initial coordinate set, to energy parameters;
      control the laser source to output a laser beam, and the plurality of components to place a focus of the laser beam at the initial location within the target volume of ocular tissue; and
      control the second optical subsystem to apply photodisruptive energy by the laser beam at the initial location in accordance with the energy parameter.

2. The system of claim 1, wherein the initial location of the focus corresponds to a location of an anatomical anchor of the eye.

3. The system of claim 2, wherein the anatomical anchor is at or near a transition point between a cornea and a sclera of the eye.

4. The system of claim 1, wherein:
   the focus is characterized by a spot size that varies as a function of the location of the focus within the target volume of ocular tissue, and
   the database maps coordinate sets to energy parameters.

5. The system of claim 1, wherein the control system derives an initial coordinate set by being further configured to:
   determine a deformed posterior conic constant k and a deformed posterior base radius of curvature Rp; and
   apply the deformed posterior conic constant k and the deformed posterior base radius of curvature Rp to the function.

6. The system of claim 1, wherein the control system is further configured to:
   control the plurality of components to move the focus to a subsequent location within the target volume of ocular tissue, wherein the subsequent location is characterized by a subsequent coordinate set that is based on the initial coordinate set;
   determine an energy parameter from the database that maps a plurality of coordinate sets of locations within the target volume of ocular tissue, including the subsequent coordinate set, to energy parameters; and
   control the second optical subsystem to apply photodisruptive energy by the laser beam at the subsequent location in accordance with the energy parameter.

7. The system of claim 1, wherein the control system is further configured to:
   control the plurality of components to scan the focus to each of a plurality of subsequent locations within the target volume of ocular tissue wherein each of the plurality of subsequent locations is characterized by a corresponding subsequent coordinate set that is based on the initial coordinate set;
   for each subsequent location and its corresponding subsequent coordinate set:
      determine an energy parameter from the database that maps a plurality of coordinate sets of locations within the target volume of ocular tissue, including the corresponding subsequent coordinate set, to energy parameters; and
      control the second optical subsystem to apply photodisruptive energy by the laser beam while the focus is at the subsequent location in accordance with the energy parameter.

8. A system for photodisrupting a target volume of ocular tissue with a laser, the target volume of ocular tissue associated with an eye of a patient, the system comprising:
   a first optical subsystem including one or more optical components configured to be coupled to the eye;
   a second optical subsystem including a laser source configured to output a laser beam, and a plurality of components optically coupled between the laser source and the first optical subsystem; and
   a control system coupled to the first optical subsystem and the second optical subsystem and configured to:
      derive an initial coordinate set based on data of the patient, the initial coordinate set corresponding to an initial location within a target volume of ocular tissue;
      determine an energy parameter from a database that maps a plurality of coordinate sets of locations within the target volume of ocular tissue, including the initial coordinate set, to energy parameters;

control the laser source to output a laser beam and the plurality of components to place a focus of the laser beam at the initial location within the target volume of ocular tissue; and control the second optical subsystem to apply photo-disruptive energy by the laser beam at the initial location in accordance with the energy parameter, wherein the control system derives an initial coordinate set corresponding to the initial location of the focus within the target volume of ocular tissue by being further configured to:

determine a deformed posterior conic constant k and a deformed posterior base radius of curvature Rp; and apply the deformed posterior conic constant k and the deformed posterior base radius of curvature Rp to a function that is based on:
  a central corneal thickness (CCT),
  a white-to-white (W2W) diameter at a meridian of a cornea of the eye, and
  an anterior cornea radius of curvature Ra at the meridian of the cornea of the eye.

9. The system of claim 8, wherein the function is:

$$y(\theta) = -\frac{c\rho^2}{1 + \sqrt{1 - (1+k)c^2\rho^2}} + CCT + t$$

where:
  θ is a rotational angle of a turret corresponding to the meridian of the eye,
  y is a distance from an origin along an azimuthal axis,
  ρ is a radial distance from the origin along a radial axis and is equal to one-half of W2W,
  c is an inverse of Rp, and
  t is a thickness of an optical component coupled to an anterior surface of a cornea of the eye.

10. The system of claim 9, wherein the control system is configured to determine the deformed posterior base radius of curvature Rp and the deformed posterior conic constant k by being configured to:
  generate a deformed anterior curve based on a natural conic constant k, the W2W, and a radius of curvature of the optical component;
  generate a deformed posterior curve based on the deformed anterior curve; and
  fit a deformed posterior fitted curve to the deformed posterior curve based on an equation having as variables the deformed posterior base radius of curvature Rp and the deformed conic constant k.

11. The system of claim 10, wherein the control system generates a deformed posterior curve based on the deformed anterior curve by being configured to:
  determine a plurality of points of the deformed posterior curve relative to a corresponding plurality of points of the deformed anterior curve based on a corresponding plurality of thicknesses of the cornea normal to each of the plurality of points of the deformed anterior curve; and
  define the deformed posterior curve from the plurality of points of the deformed posterior curve.

* * * * *